(12) United States Patent
Schmitt et al.

(10) Patent No.: US 9,457,312 B2
(45) Date of Patent: Oct. 4, 2016

(54) SEQUESTRATION AND RELEASE OF CARBON DIOXIDE

(71) Applicant: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

(72) Inventors: Wolfgang Schmitt, Bray (IE); Annemarie O'Toole, Delgany (IE)

(73) Assignee: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE)

(*) Notice: Subject to any disclaimer, the term of this patent is extended or adjusted under 35 U.S.C. 154(b) by 0 days.

(21) Appl. No.: 14/358,776

(22) PCT Filed: Nov. 15, 2012

(86) PCT No.: PCT/IE2012/000051
§ 371 (c)(1),
(2) Date: May 16, 2014

(87) PCT Pub. No.: WO2013/072906
PCT Pub. Date: May 23, 2013

(65) Prior Publication Data
US 2014/0371478 A1   Dec. 18, 2014

Related U.S. Application Data

(60) Provisional application No. 61/560,342, filed on Nov. 16, 2011.

(30) Foreign Application Priority Data

Nov. 16, 2011 (IE) .................................... 2011/0503

(51) Int. Cl.
*C07F 1/08* (2006.01)
*C07F 5/00* (2006.01)
(Continued)

(52) U.S. Cl.
CPC ........ *B01D 53/1475* (2013.01); *B01D 53/1425* (2013.01); *B01D 53/1493* (2013.01);
(Continued)

(58) Field of Classification Search
CPC ..... B01D 53/1475; C07C 1/04; C07F 13/00; C07F 5/06; C07F 15/02; C07F 5/00; C07F 11/00; C07F 1/08; C07F 15/025; C07F 13/005; C07F 5/069; B01J 20/223
USPC .............. 556/40; 585/733; 423/226, 228, 26
See application file for complete search history.

(56) References Cited

PUBLICATIONS

Schmitt et al., Journal of Inorganic Biochemistry, vol. 91, No. 1, pp. 173-189 (2002).*
(Continued)

*Primary Examiner* — Porfirio Nazario Gonzalez
(74) *Attorney, Agent, or Firm* — Bookoff McAndrews, PLLC

(57) ABSTRACT

A method for reversible capture and release of carbon dioxide comprises the steps of providing a solution of a defined tetranuclear complex or mixture thereof, in which adsorption sites are provided by coordinated solvent molecules such as water molecules. The solution is exposed to the atmosphere or to a gas stream containing carbon dioxide to sequester carbon dioxide, and the pH of the resultant reaction mixture is adjusted to facilitate the release of carbon dioxide. The solution which is used to sequester carbon dioxide is a solution of a polynuclear transition metal compound having the formula: (I) and the tetranuclear transition metal compound that has sequestered carbon dioxide is of the formula: (II).

26 Claims, 10 Drawing Sheets

Complex 1

(51) Int. Cl.

| | |
|---|---|
| C07F 11/00 | (2006.01) |
| C07F 13/00 | (2006.01) |
| C07F 15/02 | (2006.01) |
| B01D 53/14 | (2006.01) |
| C07C 1/04 | (2006.01) |
| C07F 5/06 | (2006.01) |
| B01J 20/22 | (2006.01) |

(52) U.S. Cl.
CPC ............... *B01J20/223* (2013.01); *C07C 1/04* (2013.01); *C07F 1/08* (2013.01); *C07F 5/00* (2013.01); *C07F 5/003* (2013.01); *C07F 5/06* (2013.01); *C07F 5/069* (2013.01); *C07F 11/00* (2013.01); *C07F 11/005* (2013.01); *C07F 13/00* (2013.01); *C07F 13/005* (2013.01); *C07F 15/02* (2013.01); *C07F 15/025* (2013.01); *B01D 2252/00* (2013.01); *B01D 2255/2073* (2013.01); *B01D 2255/2092* (2013.01); *B01D 2255/20738* (2013.01); *B01D 2255/20753* (2013.01); *B01D 2255/20761* (2013.01); *B01D 2255/20784* (2013.01); *B01D 2255/20792* (2013.01); *B01D 2255/705* (2013.01); *B01D 2257/504* (2013.01); *B01D 2258/0283* (2013.01); *Y02C 10/04* (2013.01); *Y02C 10/06* (2013.01); *Y02C 10/08* (2013.01); *Y02C 20/20* (2013.01); *Y02P 20/152* (2015.11)

(56) References Cited

PUBLICATIONS

Anderson, J. et al., "A Novel Tridentate Coordination Mode for the Carbonatonickel System Exhibited in an Unusual Hexanuclear Nickel(II) $\mu_3$-Carbonato-Bridged Complex," *Dalton Trans.*, pp. 9153-9156 (2009).

Bacaksiz, E. et al., "The Effects of Zinc Nitrate, Zinc Acetate and Zinc Chloride Precursors on Investigation of Structural and Optical Properties of ZnO Thin Films," *J. Alloys and Compounds*, vol. 466, pp. 447-450. (2008).

Bunimovichin Y.L. et al., "Electrochemically Programmed, Spatially Selective Biofunctionalization of Silicon Wires," *Langmuir*, vol. 20, pp. 10630-10638 (2004).

Breck, D.W., "Aperture Sizes in Dehydrated Zeolites", in *Zeolite Molecular Sieves*; Krieger: Malabar, FL, p. 65 (1984).

Cheng, C.F. et al.,"Optimal Parameters for the Synthesis of the Mesoporous Molecular Sieve [Si]-MCM-41," *J. Chem. Soc., Faraday Trans.*, vol. 93, No. 1, pp. 193-197 (1997).

Corma A. et al., "ITQ-15: The First Ultralarge Pore Zeolite With a Bi-Directional Pore System Formed by Intersecting 14- and 12-Ring Channels, and its Catalytic Implications," *Chem. Commun.*, pp. 1356-1357 (2004).

Damen, K. et al., "A Comparison of Electricity and Hydrogen Production Systems with $CO_2$ Capture and Storage. Part A: Review and Selection of Promising Conversion and Capture Technologies," *Progress in Energy and Combustion Science*, vol. 32, pp. 215-246 (2006).

Férey, G. et al., "A Chromium Terephthalate-Based Solid with Unusually Large Pore Volumes and Surface Area", *Science*, vol. 309, pp. 2040-2042 (2005).

Fondo, M. et al., "Insights Into the Absorption of Carbon Dioxide by Zinc Substrates: Isolation and Reactivity of Di- and Tetranuclear Zinc Complexes," *Dalton Trans.*, No. 14, pp. 2135-2141 (2004).

Furukawa, H. et. al., "Independent Verification of the Saturation Hydrogen Uptake in MOF-177 and Establishment of a Benchmark for Hydrogen Adsorption in Metal-Organic Frameworks," *J. Mater. Chem.*, vol. 17, pp. 3197-3204 (2007).

Furukawa, H. et. al., "Ultrahigh Porosity in Metal Organic Frameworks," *Science*, vol. 329, pp. 424-428 (2010).

Grün, M. et al., "The Synthesis of Micrometer-and Submicrometer-Size Spheres of Ordered Mesoporous Oxide MCM-41," vol. 9, No. 3, pp. 254-257 (1997).

Isono et al., "Weak Acid-Strong Base Type Charge-Mosaic Membrane. I. Carboxylic Acid-Quaternary Amine System," *J. Membrane Science*, vol. 43, pp. 205-216 (1989).

Koh, K. et. al., "A Porous Coordination Copolymer with over 5000 $m^2$/g BET Surface Area," *J. Am. Chem. Soc.*, vol. 131, pp. 4184-4185 (2009).

Lackner, K. et al., "Capturing Carbon Dioxide from Air" (presentation), May 14-17, 2001, First National Conference on Carbon Sequestration, Washington, DC, USA (15 pages).

Llewellyn, P.L. et al., "High Uptakes of $CO_2$ and $CH_4$ in Mesoporous Metal-Organic Frameworks MIL-100 and MIL-101", *Langmuir*, vol. 24, pp. 7245-7250 (2008).

Mishra, A. K. et al., "Convenient Route for Synthesis of Bifunctional Chelating Agent: 1-(p-Aminobenzyl) ethylenediaminetetramethylphosphonic acid- Folate Conjugate (Am-Bz-EDTMP-Folate)," *Chem. Lett.*, vol. 34, No. 8, pp. 1098-1099 (2005).

Meunier, S. et al., "New Nitrilotriacetic Acid and Ethylenediaminetetraacetic Acid Nitro Derivatives for the Synthesis of Bifunctional and Trifunctional Chelating Agents," *Synthetic Communications*, vol. 35, pp. 2415-2425 (2005).

Moser, P. et al., "Enabling Post Combustion Capture Optimization—The Pilot Plan Project at Niederaussem," *Energy Procedia*, vol. 1, pp. 807-814 (2009).

O'Toole, A. et al. "Fixation, Storage and Activation of $CO_2$ using Iminodiacetic Acid-Based Coordination Complexes" (poster), Jun. 23, 2010, EPA National Research Conference, Croke Park, Dublin, Ireland (2 pages).

O'Toole, A. et al., "Fixation, Storage and Activation of $CO_2$ using Iminodiacetic Acid-Based Coordination Compounds" (presentation), May 17, 2011, Photochemistry and Photochemical Techniques Conference, University College Dublin, Ireland (2 pages).

O'Toole, A. et al., "Fixation, Storage and Activation of $CO_2$ using Iminodiacetic Acid-Based Coordination Compounds" (presentation), May 25, 2011, Solar Fuels: Light Capture and Electron Flow (Europe-US Strategic Meeting), Prague, Czech Republic (28 pages).

O'Toole, A. et al., "Fixation, Storage and Activation of $CO_2$ using Iminodiacetic Acid-Based Coordination Compounds" (poster), Sep. 5-7, 2011, Faraday Discussion 155, University of Edinburgh, Scotland (1 page).

O'Toole, A. et al., "Fixation, Storage and Activation of $CO_2$ using Iminodiacetic Acid-Based Coordination Compounds" (poster), Dec. 1, 2010, Solar Fuels/Photochemistry Conference, School of Chemistry, Trinity College Dublin, Ireland (2 pages).

Paillaud, J. et al., "Extra-Large-Pore Zeolites with Two-Dimensional Channels Formed by 14 and 12 Rings," *Science*, vol. 304, pp. 990-992 (2004).

Salis, A. et al., "Physical and Chemical Adsorption of Mucor Javanicus Lipase on SBA-15 Mesoporous Silica. Synthesis, Structural Characterization, and Activity Performance," *Langmuir*, vol. 21, pp. 5511-5516 (2005).

Schmitt, W. et al., "Biomimetic Hydrolytic Activation by Fe(III) and Aggregates: Structures, Reactivity and Properties of Novel Oxo-Bridged Iron Complexes," *J. Inorg. Biochem.*, vol. 91, No. 1, pp. 173-189 (2002).

Schmitt, W. et al., "Synthesis, Structures and Properties of Hydrolytric Al(III) Aggregates and Fe(III) Analogues Formed With Iminodiacetate-Based Chelating Ligands", *Coordination Chemistry Reviews*, vol. 228, pp. 115-126 (2002).

Schmitt, W. et al., "Untersuchung von Hydrolysereaktionen zum Aufbau von Eisen(III)-Oxo-Aggregaten". ("Investigation of the Hydrolytic Build-Up of Iron (III)-Oxo-Aggregates"), *Zeitschrift Für Anorganische and Allgemeine Chemie*, vol. 628, No. 11, pp. 2443-2457 (2002).

Siegenthaler, U. et al., "Stable Carbon Cycle-Climate Relationship During the Late Pleistocene". *Science*, vol. 310, pp. 1313-1317 (2005).

(56) References Cited

OTHER PUBLICATIONS

Singh, P. et al., "Solubility of $CO_2$ in Aqueous Solution of Newly Developed Absorbents," *Energy Procedia*, vol. 1, p. 1257-1264 (2009).

Strohmaier, K. et al., "Structure of the First Silicate Molecular Sieve With 18-Ring Pore Openings, ECR-34", *J. Am. Chem. Soc.*, vol. 125, pp. 16035-16039 (2003).

Stolaroff, J. et al., "Carbon Dioxide Capture from Atmospheric Air Using Sodium Hydroxide Spray," *Environ. Sci. Technol.*, vol. 42, No. 8, pp. 2728-2735 (2008).

Suda, T. et al., "Facile Determination of Dissolved Species in $CO_2$-Amine-$H_2O$ System by NMR Spectroscopy", *Chem. Lett.*, No. 9, pp. 777-778 (1996).

Varkey, S. P. et al., "Zeolite-Encapsulated Manganese (III)Salen Complexes", *Journal of Molecular Catalysis A: Chemical*, vol. 135, pp. 295-306 (1998).

Warshawsky, et al., Bifunctional Chelating Agents, Part 3: † 4,5-Bis[di(carboxymethyl) amino]-N-(aminoalkyl) valeramide, an EDTA with an Amine Functionality and Amide-Type Linker Arm, *J. Chem. Soc., Perkins Trans.*, vol. 1, pp. 1781-1786 (1989).

Warshawsky, A. et al., "Ring Cleavage of N-Acyl- and N-(Arylsulfonyl)histamines with Di-tert-butyl Dicarbonate. A One-Pot Synthesis of 4-Acylamino- and 4-Arylsulfonylamino-1,2-diaminobutanes," *Synthesis*, pp. 825-829 (1989).

Wight, A.P. et al., "Design and Preparation of Organic-Inorganic Hybrid Catalysts", *Chem. Rev.*, vol. 102, pp. 3589-3614 (2002).

Xiao, L. et al., "A Method for the Synthesis of 2-Oxazolidinones and 2-Imidazolidinones from Five-Membered Cyclic Carbonates and β-Aminoalcohols or 1,2-Diamines," *Green Chem.*, vol. 9, pp. 369-372 (2007).

Yiu, H. et al., "Enzyme Immobilisation Using SBA-15 Mesoporous Molecular Sieves with Functionalised Surfaces," *J. Molecular Catalysis B: Enzymatic*, vol. 15, pp. 81-92 (2001).

Zeman, F. et al., "Capturing Carbon Dioxide Directly from the Atmosphere," *World Resource Rev.*, vol. 16, No. 2, pp. 157-172 (2004).

Zhao, D. et al., "Triblock Copolymer Synthesis of Mesoporous Silica with Periodic 50 to 300 Angstrom Pores," *Science*, vol. 279, pp. 548-552 (1998).

* cited by examiner

Complex 2

SEQUESTRATION AND RELEASE OF CARBON DIOXIDE

This application is a national stage filing under 35 U.S.C. §371 of International Application No. PCT/IE2012/000051, filed on Nov. 15, 2012, incorporated by reference herein in its entirety, which published in the English language and claims the benefit of priority U.S. Provisional Application No. 61/560,342 filed on Nov. 16, 2011, and to Irish Application No. 2011/0503 filed on Nov. 16, 2011.

INTRODUCTION $CO_2$ is a greenhouse gas and the role of increasing atmospheric $CO_2$ concentrations on global warming is well established. Widespread combustion of fossil fuels has upset this balance and led to the emission of $6 \times 10^9$ tons of carbon per year as $CO_2$. Industrial activity has raised levels of $CO_2$ in the atmosphere from 280 ppmV in pre-industrial times to the present excess of 385 ppmV. $CO_2$ has high infrared absorbance and long atmospheric lifetime which explain the significant role that $CO_2$ has on global warming effects.

The benchmark concentration for stabilisation of $CO_2$ emissions is 550 ppmV. A four fold decrease in $CO_2$ emissions is required in the coming decades in order to successfully stabilise the $CO_2$ concentrations by the year 2100. It is predicted that fossil fuels will remain the dominant global source of energy for the next 25 years. It is known that modest reductions in $CO_2$ emissions will only delay the growth of $CO_2$ levels in the atmosphere (a reduction of 20% of emissions will buy 15 years). The intergovernmental panel on climate change (IPCC) estimates that the economic potential of carbon capture and sequester (CCS) technologies could be between 10% and 55% of the total carbon mitigation effort until the year 2100. Therefore it is of fundamental importance that environmentally friendly, efficient, and economically viable green technologies are readily available for implementation in CCS technologies.

There is very limited availability of green technologies for the capture and sequestration of $CO_2$. Current technologies are expensive, require steps to remove $NO_x$ and $SO_x$ impurities from the gas stream prior to $CO_2$ capture, are inefficient and energy intensive. There is a need for an environmentally friendly green technology that does not require the removal of impurities in the gas stream, can remove atmospheric levels of $CO_2$, operates at ambient conditions and ambient $CO_2$ concentration levels, and offers improved $CO_2$ capturing efficiencies.

Post combustion chemical absorption systems are commonly used in industry. These post combustion CCS technologies use $CO_2$ scrubbers to remove $CO_2$ from their flue gasses. Typical scrubber technologies utilise amines, such as monoethanolamine, to absorb $CO_2$. In this process the flue gas is cooled to remove impurities such as $NO_x$ and $SO_x$. This removal step is essential prior to $CO_2$ capture as these components form heat stable salts in the presence of amines. In an absorption column, $CO_2$ reacts chemically with the amine. The $CO_2$-rich absorbent is pumped to a desorber, where $CO_2$ is released by increasing the temperature up to 120° C. The regenerated absorbent is recycled to the absorber and $CO_2$ is dried and compressed for transport conditions (typically between 100 and 150 bar). This process requires high energy inputs—4.2 MJ/Kg $CO_2$.

Alternative options to capture $CO_2$ from flue gasses are adsorption, low temperature distillation, and membrane technology. Other scrubber technologies utilise calcium oxide ($CO_2$ reacts with calcium oxide to produce limestone this process is referred to as carbonate looping), serpentinite, algae based carbon sinks, molecular sieves, polymer membrane gas separators and activated carbon systems. These processes operate under high pressures and are energy intensive.

Research is currently underway into pressure swing adsorption (PSA) processes to capture CO) in large quantities from coal-fired power plants. PSA processes rely on the fact that under pressure, gases tend to be attracted to solid surfaces, or "adsorbed". The higher the pressure, the more gas is adsorbed; when the pressure is reduced, the gas is released, or desorbed. However the energy requirements of conventional pressure (and temperature) swing physical adsorption, in which $CO_2$ binds to a solid surface (e.g. zeolites), are prohibitively large.

The PSA processes mentioned in 2 above are the current technologies used to separate carbon dioxide from biogases to increase the methane ($CH_4$) content and also to minimise the $CO_2$ content in gas mixtures required for many industrial processes.

K. Damen et al., Progress in Energy and Combustion Science 32 (2006) 215-246

STATEMENTS OF INVENTION

According to the invention there is provided method for reversible capture and release of carbon dioxide comprising the steps of:

providing a solution of a tetranuclear complex or mixture thereof, in which absorption sites are provided by coordinated solvent molecules such as water molecules;

exposing the solution to the atmosphere or to a gas stream containing carbon dioxide to sequester carbon dioxide; and adjusting the pH of the resultant reaction mixture to facilitate the release of carbon dioxide, wherein the solution which is used to sequester carbon dioxide is a solution of a polynuclear transition metal compound having the formula:

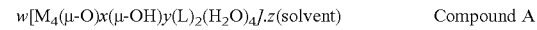   Compound A wherein the tetranuclear transition metal compound that has sequestered carbon dioxide is of the formula:

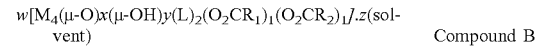   Compound B and wherein the polynuclear transition metal compound that is formed as a result of the pH induced release of carbon dioxide from Compound B is of the formula:

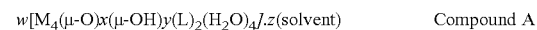   Compound A wherein w is any ion or mixture of ions in appropriate stoichiometries for compounds A or B to be electronically neutral, M is selected from one or more of Fe, Al and Ga or one or more of Mn, Ru, Zn, Cr, Co, Ni, In, Cu and V, x and y are numerical values the sum of which equals to 2, L is any suitable aminocarboxylic acid ligand that stabilises the tetranuclear complexes, $R_1$ and $R_2$=any sidegroup or combination of two sidegroups from the following list: an oxygen atom, an OH group, a hydrazine or hydrazinium moiety, an ammonia or ammonium moiety or any primary, secondary or tertiary aliphatic or aromatic amine or ammonium moiety and their derivatives including diamine, triamine or alcohol amine or corresponding ammonium moieties, $O_2CR_1$ or $O_2CR_2$=any carbamate or carbamic acid moiety.

z may be 0 or any positive number, and solvent is any suitable solvent.

The $O_2CR_1$ and $O_2CR_2$ moieties include carbamates in their anionic form and neutral carbamic acid moieties (zwitterionic form).

In one case the pH of the solution containing the tetranuclear transition metal complex or a mixture of transition metal complexes (Compound A) is adjusted from a pH of between 14 and 7.9 to a pH of less than 7.8 by addition of appropriate aliquots of acidic media.

In one case the release of carbon dioxide occurs when compound B is dissolved in aqueous media at a pH of less than 7.8.

The pH of the solution containing the tetranuclear transition metal complex or a mixture of transition metal complexes (Compound A) is adjusted from a pH of about 8.5 to a pH of about 4.

In some instances the tetranuclear transition metal complex or the mixture of transition metal complexes undergo a series of substitution reactions, protonation and deprotonation reactions and intermolecular rearrangements that results in the formation of the polynuclear transition metal complex or a mixture of transition metal complexes that have the ability to capture and release carbon dioxide.

In some embodiments M is Fe. In some embodiments M is Al. In some embodiments M is Cu. In some embodiments M is Ga. In some embodiments M is Mn. In some embodiments M is Cr. In one embodiment M is selected from one or more of Cu, Mn, and Cr.

In one embodiment M is selected from one or more of Fe, Al, Cu, Ga, Mn, and Cr.

In one embodiment L is

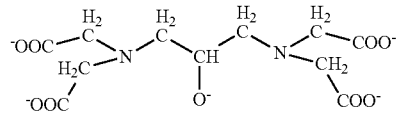

(hpdta) or a derivative thereof.

The solvent may be a polar solvent which may, for example, be selected from $H_2O$, methanol, ethanol, propanol, isopropanol, DMF (dimethylformamide), DMA (dimethyl acetamide), DEF (diethylformamide), DEA (diethylacetamide), DMSO (dimethyl sulfoxide), acetonitrile and mixtures thereof.

In some embodiments the complex is selected from:

w[$Fe^{III}_4$(μ-O)(μ-OH)(hpdta)$_2$(CO$_3$)$_2$].x sol (1), w[Fe$_4$(μ-O)(μ-OH)(hpdta)$_2$(O$_2$CNHC$_3$H$_6$NH$_3$)$_2$].x sol (2), w[Fe$_4$(μ-O)(μ-OH)(hpdta)$_2$(O$_2$CNHNH$_3$)$_2$].x sol (3), w[Fe$_4$(μ-O)(μ-OH)(hpdta)$_2$(O$_2$CNHC$_4$H$_8$NH$_3$)$_2$].x sol (4), w[Fe$_4$(μ-O)(μ-OH)(hpdta)$_2$(O$_2$CNHC$_6$H$_{12}$NH$_3$)$_2$].x sol (5), w[Fe$_4$(μ-O)(μ-OH)(hpdta)$_2$(O$_2$CNHC$_7$H$_{14}$NH$_3$)$_2$].x sol (6), w[Fe$_4$(μ-O)(μ-OH)(hpdta)$_2$(O$_2$CNHC$_2$H$_4$NC$_4$H$_8$NH$_2$)$_2$].xsol (7), w[Fe$_4$(μ-O)(μ-OH)(hpdta)$_2$(O$_2$CNHC$_3$H$_7$)$_2$].xsol (8), w[Fe$_4$(μ-O)(μ-OH)(hpdta)$_2$(O$_2$CNHCH$_2$CH$_2$HNCH$_2$CH$_2$NH$_3$)$_2$].xsol (9), w[Fe$_4$(μ-O)(μ-OH)(hpdta)$_2$(O$_2$CNHCH$_2$CH$_2$OH)$_2$].xsol (10), and w[Fe$_4$(μ-O)(μ-OH)(hpdta)$_2$(O$_2$CNHC$_2$H$_4$NH$_3$)$_2$].x sol (11).

In some embodiments the complex is selected from:

w[$Al^{III}_4$(μ-O)(μ-OH)(hpdta)$_2$(CO$_3$)$_2$].sol (12), w[Al$_4$(μ-O)(μ-OH)(hpdta)$_2$(O$_2$CNHC$_2$H$_4$NH$_3$)$_2$].x sol (13), w[Al$_4$(μ-O)(μ-OH)(hpdta)$_2$(O$_2$CNHNH$_3$)$_2$].x sol (14), w[Al$_4$(μ-O)(μ-OH)(hpdta)$_2$(O$_2$CNHC$_4$H$_8$NH$_3$)$_2$].x sol (15), w[Al$_4$(μ-O)(μ-OH)(hpdta)$_2$(O$_2$CNHC$_6$H$_{12}$NH$_3$)$_2$].x sol (16), w[Al$_4$(μ-O)(μ-OH)(hpdta)$_2$(O$_2$CNHC$_7$H$_{14}$NH$_3$)$_2$].x sol (17), w[Al$_4$(μ-O)(μ-OH)(hpdta)$_2$(O$_2$CNHC$_2$H$_4$NC$_4$H$_8$NH$_2$)$_2$].xsol (18), w[Al$_4$(μ-O)(μ-OH)(hpdta)$_2$(O$_2$CNHC$_3$H$_7$)$_2$].xsol (19), w[Al$_4$(μ-O)(μ-OH)(hpdta)$_2$(O$_2$CNHCH$_2$CH$_2$HNCH$_2$CH$_2$NH$_3$)$_2$].xsol (20), and w[Al$_4$(μ-O)(μ-OH)(hpdta)$_2$(O$_2$CNHCH$_2$CH$_2$OH)$_2$].xsol (21).

In some embodiments the complex is selected from:

w[$Cu^{III}_4$(μ-O)(μ-OH)(hpdta)$_2$(CO$_3$)$_2$].sol (22), w[Cu$_4$(μ-O)(μ-OH)(hpdta)$_2$(O$_2$CNHC$_2$H$_4$NH$_3$)$_2$].x sol (23), w[Cu$_4$(μ-O)(μ-OH)(hpdta)$_2$(O$_2$CNHC$_2$H$_4$NH$_3$)$_2$].x sol (24), w[Cu$_4$(μ-O)(μ-OH)(hpdta)$_2$(O$_2$CNHNH$_3$)$_2$].x sol (25), w[Cu$_4$(μ-O)(μ-OH)(hpdta)$_2$(O$_2$CNHC$_4$H$_8$NH$_3$)$_2$].x sol (26), w[Cu$_4$(μ-O)(μ-OH)(hpdta)$_2$(O$_2$CNHC$_6$H$_{12}$NH$_3$)$_2$].x sol (27), w[Cu$_4$(μ-O)(μ-OH)(hpdta)$_2$(O$_2$CNHC$_7$H$_{14}$NH$_3$)$_2$].x sol (28), w[Cu$_4$(μ-O)(μ-OH)(hpdta)$_2$(O$_2$CNHC$_2$H$_4$NC$_4$H$_8$NH$_2$)$_2$].xsol (29), w[Cu$_4$(μ-O)(μ-OH)(hpdta)$_2$(O$_2$CNHC$_3$H$_7$)$_2$].xsol (30), w[Cu$_4$(μ-O)(μ-OH)(hpdta)$_2$(O$_2$CNHCH$_2$CH$_2$HNCH$_2$CH$_2$NH$_3$)$_2$].xsol (31), and w[Cu$_4$(μ-O)(μ-OH)(hpdta)$_2$(O$_2$CNHCH$_2$CH$_2$OH)$_2$].xsol (32).

In some embodiments the complex is selected from:

w[$Ga^{III}_4$(μ-O)(μ-OH)(hpdta)$_2$(CO$_3$)$_2$].sol (33), w[Ga$_4$(μ-O)(μ-OH)(hpdta)$_2$(O$_2$CNHC$_2$H$_4$NH$_3$)$_2$].x sol (34), w[Ga$_4$(μ-O)(μ-OH)(hpdta)$_2$(O$_2$CNHC$_2$H$_4$NH$_3$)$_2$].x sol (35), w[Ga$_4$(μ-O)(μ-OH)(hpdta)$_2$(O$_2$CNHNH$_3$)$_2$].x sol (36), w[Ga$_4$(μ-O)(μ-OH)(hpdta)$_2$(O$_2$CNHC$_4$H$_8$NH$_3$)$_2$].x sol (37), w[Ga$_4$(μ-O)(μ-OH)(hpdta)$_2$(O$_2$CNHC$_6$H$_{12}$NH$_3$)$_2$].x sol (38), w[Ga$_4$(μ-O)(μ-OH)(hpdta)$_2$(O$_2$CNHC$_7$H$_{14}$NH$_3$)$_2$].x sol (39), w[Ga$_4$(μ-O)(μ-OH)(hpdta)$_2$(O$_2$CNHC$_2$H$_4$NC$_4$H$_8$NH$_2$)$_2$].xsol (40), w[Ga$_4$(μ-O)(μ-OH)(hpdta)$_2$(O$_2$CNHC$_3$H$_7$)$_2$].xsol (41), w[Ga$_4$(μ-O)(μ-OH)(hpdta)$_2$(O$_2$CNHCH$_2$CH$_2$HNCH$_2$CH$_2$NH$_3$)$_2$].xsol (42), and w[Ga$_4$(μ-O)(μ-OH)(hpdta)$_2$(O$_2$CNHCH$_2$CH$_2$OH)$_2$].xsol (43).

In some embodiments the complex is selected from:

w[Mn$_4$(μ-O)(μ-OH)(hpdta)$_2$(CO$_3$)$_2$].sol (44), w[Mn$_4$(μ-O)(μ-OH)(hpdta)$_2$(O$_2$CNHC$_2$H$_4$NH$_3$)$_2$].x sol (45), w[Mn$_4$(μ-O)(μ-OH)(hpdta)$_2$(O$_2$CNHC$_2$H$_4$NH$_3$)$_2$].x sol (46),
w[Mn$_4$(μ-O)(μ-OH)(hpdta)$_2$(O$_2$CNHNH$_3$)$_2$].x sol (47),
w[Mn$_4$(μ-O)(μ-OH)(hpdta)$_2$(O$_2$CNHC$_4$H$_8$NH$_3$)$_2$].x sol (48),
w[Mn$_4$(μ-O)(μ-OH)(hpdta)$_2$(O$_2$CNHC$_6$H$_{12}$NH$_3$)$_2$].x sol (49),
w[Mn$_4$(μ-O)(μ-OH)(hpdta)$_2$(O$_2$CNHC$_7$H$_{14}$NH$_3$)$_2$].x sol (50),
w[Mn$_4$(μ-O)(μ-OH)(hpdta)$_2$(O$_2$CNHC$_2$H$_4$NC$_4$H$_8$NH$_2$)$_2$].xsol (51),
w[Mn$_4$(μ-O)(μ-OH)(hpdta)$_2$(O$_2$CNHC$_3$H$_7$)$_2$].xsol (52),
w[Mn$_4$(μ-O)(μ-OH)(hpdta)$_2$(O$_2$CNHCH$_2$CH$_2$HNCH$_2$CH$_2$NH$_3$)$_2$].xsol (53), and
w[Mn$_4$(μ-O)(μ-OH)(hpdta)$_2$(O$_2$CNHCH$_2$CH$_2$OH)$_2$].xsol (54).

In some embodiments the complex is selected from:
w[Cr$_4$(μ-O)(μ-OH)(hpdta)$_2$(CO$_3$)$_2$].sol (55),
w[Cr$_4$(μ-O)(μ-OH)(hpdta)$_2$(O$_2$CNHC$_2$H$_4$NH$_3$)$_2$].x sol (56),
w[Cr$_4$(μ-O)(μ-OH)(hpdta)$_2$(O$_2$CNHC$_2$H$_4$NH$_3$)$_2$].x sol (57),
w[Cr$_4$(μ-O)(μ-OH)(hpdta)$_2$(O$_2$CNHNH$_3$)$_2$].x sol (58),
w[Cr$_4$(μ-O)(μ-OH)(hpdta)$_2$(O$_2$CNHC$_4$H$_8$NH$_3$)$_2$].x sol (59),
w[Cr$_4$(μ-O)(μ-OH)(hpdta)$_2$(O$_2$CNHC$_6$H$_{12}$NH$_3$)$_2$].x sol (60),
w[Cr$_4$(μ-O)(μ-OH)(hpdta)$_2$(O$_2$CNHC$_7$H$_{14}$NH$_3$)$_2$].x sol (61),
w[Cr$_4$(μ-O)(μ-OH)(hpdta)$_2$(O$_2$CNHC$_2$H$_4$NC$_4$H$_8$NH$_2$)$_2$].xsol (62),
w[Cr$_4$(μ-O)(μ-OH)(hpdta)$_2$(O$_2$CNHC$_3$H$_7$)$_2$].xsol (63), and
w[Cr$_4$(μ-O)(μ-OH)(hpdta)$_2$(O$_2$CNHCH$_2$CH$_2$HNCH$_2$CH$_2$NH$_3$)$_2$].xsol (64).

The complex may be isolated as compound A or compound B or assemble readily in solutions from their metal salts and organic ligands at appropriate pH.

The polynuclear transition metal complex or mixture of transition metal complexes may be either generated in situ from the assembly of their corresponding ligand and metal salts in solution at appropriate pH values, or, isolated as a solid that is dissolved in a polar solvent at appropriate pH values.

In some embodiments the compounds A or B or any mixtures thereof, are immobilised.

The compounds A or B or any mixtures thereof may, for example, be immobilised on a solid support.

In some cases one or more molecules of compound A or compound B, or any mixture thereof, are immobilised onto a solid support and the solid support is alternated between two or more pH environments for reversible sequestration and release of carbon dioxide.

The solid support may be introduced to an environment with a pH value between pH 7.9 and pH 14 and is exposed to carbon dioxide for sequestration of carbon dioxide.

For example, the solid support may be introduced to an environment having a pH of less than pH 7.8 which results in the release of carbon dioxide and regeneration of compound A.

The solid support may be re-introduced into an environment having a pH of between pH 7.9 and pH 14 and exposed to carbon dioxide for sequestration of carbon dioxide.

The pH environment may be a solution, gaseous, or solid phase.

In some embodiments hpdta ligands or derivatives thereof are used for immobilisation of the complex.

The hpdta derivative may be of the formula:

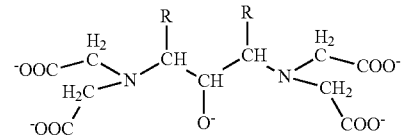

wherein functionalisations of R include one or two combinations of the following whereby one of the R groups is a H atom and the second R group can be 1-alkene and 1-alkyne side chains or alkyl chains with terminal carboxylic acid, nitrile, aldehyde, amine or nitro functions.

In some cases the immobilisation comprises the fixation or crafting of the complex on a solid support.

In some cases the support is selected from a membrane, a silicate, an alumosilicate, a metal-organic framework, a metal, a metalloid and carbon, fixation may be achieved through covalent bonding, coordination bonds and/or electrostatic interactions between the solid support and a complex.

For example, the solid support may comprise any solid form of compound A or B, or any mixture thereof, including polymerised derivatives of the compounds or structural derivatives that result from protonation and deprotonation reactions and intermolecular rearrangements of compound A and B giving rise to metal complexes that have the ability to capture and release carbon dioxide.

The invention also provides a compound selected from:
w[Fe$^{III}_4$(μ-O)(μ-OH)(hpdta)$_2$(CO$_3$)$_2$].x sol (1),
w[Fe$_4$(μ-O)(μ-OH)(hpdta)$_2$(O$_2$CNHC$_3$H$_6$NH$_3$)$_2$].x sol (2),
w[Fe$_4$(μ-O)(μ-OH)(hpdta)$_2$(O$_2$CNHNH$_3$)$_2$].x sol (3),
w[Fe$_4$(μ-O)(μ-OH)(hpdta)$_2$(O$_2$CNHC$_4$H$_8$NH$_3$)$_2$].x sol (4),
w[Fe$_4$(μ-O)(μ-OH)(hpdta)$_2$(O$_2$CNHC$_6$H$_{12}$NH$_3$)$_2$].x sol (5),
w[Fe$_4$(μ-O)(μ-OH)(hpdta)$_2$(O$_2$CNHCH$_{14}$NH$_3$)$_2$].x sol (6),
w[Fe$_4$(μ-O)(μ-OH)(hpdta)$_2$(O$_2$CNHC$_2$H$_4$NC$_4$H$_8$NH$_2$)$_2$].xsol (7),
w[Fe$_4$(μ-O)(μ-OH)(hpdta)$_2$(O$_2$CNHC$_3$H$_7$)$_2$].xsol (8),
w[Fe$_4$(μ-O)(μ-OH)(hpdta)$_2$(O$_2$CNHCH$_2$CH$_2$HNCH$_2$CH$_2$NH$_3$)$_2$].xsol (9),
w[Fe$_4$(μ-O)(μ-OH)(hpdta)$_2$(O$_2$CNHCH$_2$CH$_2$OH)$_2$].xsol (10), and
w[Fe$_4$(μ-O)(μ-OH)(hpdta)$_2$(O$_2$CNHC$_2$H$_4$NH$_3$)$_2$].x sol (11).

The invention also provides a compound selected from:
w[Al$^{III}_4$(μ-O)(μ-OH)(hpdta)$_2$(CO$_3$)$_2$].sol (12),
w[Al$_4$(μ-O)(μ-OH)(hpdta)$_2$(O$_2$CNHC$_2$H$_4$NH$_3$)$_2$].x sol (13),
w[Al$_4$(μ-O)(μ-OH)(hpdta)$_2$(O$_2$CNHNH$_3$)$_2$].x sol (14),
w[Al$_4$(μ-O)(μ-OH)(hpdta)$_2$(O$_2$CNHC$_4$H$_8$NH$_3$)$_2$].x sol (15),
w[Al$_4$(μ-O)(μ-OH)(hpdta)$_2$(O$_2$CNHC$_6$H$_{12}$NH$_3$)$_2$].x sol (16),
w[Al$_4$(μ-O)(μ-OH)(hpdta)$_2$(O$_2$CNHC$_7$H$_{14}$NH$_3$)$_2$].x sol (17),
w[Al$_4$(μ-O)(μ-OH)(hpdta)$_2$(O$_2$CNHC$_2$H$_4$NC$_4$H$_8$NH$_2$)$_2$].x sol (18),
w[Al$_4$(μ-O)(μ-OH)(hpdta)$_2$(O$_2$CNHC$_3$H$_7$)$_2$].xsol (19),
w[Al$_4$(μ-O)(μ-OH)(hpdta)$_2$(O$_2$CNHCH$_2$CH$_2$HNCH$_2$CH$_2$NH$_3$)$_2$].xsol (20), and w[Al$_4$(μ-O)(μ-OH)(hpdta)$_2$(O$_2$CNHCH$_2$CH$_2$OH)$_2$].xsol (21).

The invention also provides a compound selected from:
w[Cu$^{III}_4$(μ-O)(μ-OH)(hpdta)$_2$(CO$_3$)$_2$].sol (22),
w[Cu$_4$(μ-O)(μ-OH)(hpdta)$_2$(O$_2$CNHC$_2$H$_4$NH$_3$)$_2$].x sol (23),
w[Cu$_4$(μ-O)(μ-OH)(hpdta)$_2$(O$_2$CNHC$_2$H$_4$NH$_3$)$_2$].x sol (24),
w[Cu$_4$(μ-O)(μ-OH)(hpdta)$_2$(O$_2$CNHNH$_3$)$_2$].x sol (25),
w[Cu$_4$(μ-O)(μ-OH)(hpdta)$_2$(O$_2$CNHC$_4$H$_8$NH$_3$)$_2$].x sol (26),
w[Cu$_4$(μ-O)(μ-OH)(hpdta)$_2$(O$_2$CNHC$_6$H$_{12}$NH$_3$)$_2$].x sol (27),
w[Cu$_4$(μ-O)(μ-OH)(hpdta)$_2$(O$_2$CNHC$_7$H$_{14}$NH$_3$)$_2$].x sol (28),
w[Cu$_4$(μ-O)(μ-OH)(hpdta)$_2$(O$_2$CNHC$_2$H$_4$NC$_4$H$_8$NH$_2$)$_2$].x sol (29),
w[Cu$_4$(μ-O)(μ-OH)(hpdta)$_2$(O$_2$CNHC$_3$H$_7$)$_2$].xsol (30),
w[Cu$_4$(μ-O)(μ-OH)(hpdta)$_2$(O$_2$CNHCH$_2$CH$_2$HNCH$_2$CH$_2$NH$_3$)$_2$].x sol (31), and
w[Cu$_4$(μ-O)(μ-OH)(hpdta)$_2$(O$_2$CNHCH$_2$CH$_2$OH)$_2$].xsol (32).

The invention also provides a compound selected from:
w[Ga$^{III}_4$(μ-O)(μ-OH)(hpdta)$_2$(CO$_3$)$_2$].sol (33),
w[Ga$_4$(μ-O)(μ-OH)(hpdta)$_2$(O$_2$CNHC$_2$H$_4$NH$_3$)$_2$].x sol (34),
w[Ga$_4$(μ-O)(μ-OH)(hpdta)$_2$(O$_2$CNHC$_2$H$_4$NH$_3$)$_2$].x sol (35),
w[Ga$_4$(μ-O)(μ-OH)(hpdta)$_2$(O$_2$CNHNH$_3$)$_2$].x sol (36),
w[Ga$_4$(μ-O)(μ-OH)(hpdta)$_2$(O$_2$CNHC$_4$H$_8$NH$_3$)$_2$].x sol (37),
w[Ga$_4$(μ-O)(μ-OH)(hpdta)$_2$(O$_2$CNHC$_6$H$_{12}$NH$_3$)$_2$].x sol (38),
w[Ga$_4$(μ-O)(μ-OH)(hpdta)$_2$(O$_2$CNHC$_7$H$_{14}$NH$_3$)$_2$].x sol (39),
w[Ga$_4$(μ-O)(μ-OH)(hpdta)$_2$(O$_2$CNHC$_2$H$_4$NC$_4$H$_8$NH$_2$)$_2$].xsol (40),
w[Ga$_4$(μ-O)(μ-OH)(hpdta)$_2$(O$_2$CNHC$_3$H$_7$)$_2$].xsol (41),
w[Ga$_4$(μ-O)(μ-OH)(hpdta)$_2$(O$_2$CNHCH$_2$CH$_2$HNCH$_2$CH$_2$NH$_3$)$_2$].sol (42), and
w[Ga$_4$(μ-O)(μ-OH)(hpdta)$_2$(O$_2$CNHCH$_2$CH$_2$OH)$_2$].x sol (43).

The invention also provides a compound selected from:
w[Mn$_4$(μ-O)(μ-OH)(hpdta)$_2$(CO$_3$)$_2$].sol (44),
w[Mn$_4$(μ-O)(μ-OH)(hpdta)$_2$(O$_2$CNHC$_2$H$_4$NH$_3$)$_2$].x sol (45),
w[Mn$_4$(μ-O)(μ-OH)(hpdta)$_2$(O$_2$CNHC$_2$H$_4$NH$_3$)$_2$].x sol (46),
w[Mn$_4$(μ-O)(μ-OH)(hpdta)$_2$(O$_2$CNHNH$_3$)$_2$].x sol (47),
w[Mn$_4$(μ-O)(μ-OH)(hpdta)$_2$(O$_2$CNHC$_4$H$_8$NH$_3$)$_2$].x sol (48),
w[Mn$_4$(μ-O)(μ-OH)(hpdta)$_2$(O$_2$CNHC$_6$H$_2$NH$_3$)$_2$].x sol (49),
w[Mn$_4$(μ-O)(μ-OH)(hpdta)$_2$(O$_2$CNHC$_7$H$_{14}$NH$_3$)$_2$].x sol (50),
w[Mn$_4$(μ-O)(μ-OH)(hpdta)$_2$(O$_2$CNHC$_2$H$_4$NC$_4$H$_8$NH$_2$)$_2$].xsol (51),
w[Mn$_4$(μ-O)(μ-OH)(hpdta)$_2$(O$_2$CNHC$_3$H$_7$)$_2$].xsol (52),
w[Mn$_4$(μ-O)(μ-OH)(hpdta)$_2$(O$_2$CNHCH$_2$CH$_2$HNCH$_2$CH$_2$NH$_3$)$_2$].xsol (53), and
w[Mn$_4$(μ-O)(μ-OH)(hpdta)$_2$(O$_2$CNHCH$_2$CH$_2$OH)$_2$].xsol (54).

The invention also provides a compound selected from:
w[Cr$_4$(μ-O)(μ-OH)(hpdta)$_2$(CO$_3$)$_2$].sol (55),
w[Cr$_4$(μ-O)(μ-OH)(hpdta)$_2$(O$_2$CNHC$_2$H$_4$NH$_3$)$_2$].x sol (56),
w[Cr$_4$(μ-O)(μ-OH)(hpdta)$_2$(O$_2$CNHC$_2$H$_4$NH$_3$)$_2$].x sol (57),
w[Cr$_4$(μ-O)(μ-OH)(hpdta)$_2$(O$_2$CNHNH$_3$)$_2$].x sol (58),
w[Cr$_4$(μ-O)(μ-OH)(hpdta)$_2$(O$_2$CNHC$_4$H$_8$NH$_3$)$_2$].x sol (59),
w[Cr$_4$(μ-O)(μ-OH)(hpdta)$_2$(O$_2$CNHC$_6$H$_{12}$NH$_3$)$_2$].x sol (60),
w[Cr$_4$(μ-O)(μ-OH)(hpdta)$_2$(O$_2$CNHC$_7$H$_{14}$NH$_3$)$_2$].x sol (61),
w[Cr$_4$(μ-O)(μ-OH)(hpdta)$_2$(O$_2$CNHC$_2$H$_4$NC$_4$H$_8$NH$_2$)$_2$].xsol (62),
w[Cr$_4$(μ-O)(μ-OH)(hpdta)$_2$(O$_2$CNHC$_3$H$_7$)$_2$].xsol (63), and
w[Cr$_4$(μ-O)(μ-OH)(hpdta)$_2$(O$_2$CNHCH$_2$CH$_2$HNCH$_2$CH$_2$NH$_3$)$_2$].xsol (64).

Further, the invention provides the use of any complex as defined herein for absorption of carbon dioxide.

In addition, the invention provides the use of any complex as defined herein for reversible absorption and release of carbon dioxide.

Further, the invention provides the use of any complex as defined herein as catalysts in the electrochemical and/or photochemical activation of CO$_2$ and optional subsequent transformation into useful chemicals such as fuels.

The invention also a solid support comprising a complex as defined herein. The complex may be fixed or crafted to the support. The fixation or crafting of the complex on the solid support may, for example, be achieved through covalent bonding, coordination bonds and/or electrostatic interactions between a solid support and the complex.

In some cases the support is selected from membranes, silicates, alumosilicates, metal-organic frameworks, metals and metalloids, carbons and the like.

According to one aspect the invention provides a method for reversible absorption and release of carbon dioxide using a class of tetranuclear transition metal complexes or a mixture of transition metal complexes.

In one embodiment the invention provides a method for reversible absorption and release of carbon dioxide using a tetranuclear complex or mixture thereof where absorption sites are provided by coordinated solvent molecules such as water molecules.

In one embodiment the tetranuclear transition metal complex has one of the formulae:

$$w[M_4(\mu\text{-O})x(\mu\text{-OH})y(L)_2(H_2O)_4].z(\text{solvent}) \quad \text{Compound A}$$

$$w[M_4(\mu\text{-O})x(\mu\text{-OH})y(L)_2(O_2CR_1)_1(O_2CR_2)_1].z(\text{solvent}) \quad \text{Compound B}$$

wherein
w is any ion or mixture of ions in appropriate stoichiometries for compounds A or B to be electronically neutral,
M is a divalent or trivalent metal ion or any combination of two or more divalent and trivalent metal ions,
x and y are numerical values the sum of which equals to 2,
L is any suitable aminocarboxylic acid ligand that stabilises the tetranuclear complexes
R$_1$ and R$_2$=any sidegroup or combination of two sidegroups from the following list:
an oxygen atom, OH group, hydrazine, ammonia or any primary, secondary or tertiary aliphatic or aromatic amines and their derivatives including diamines, triamines or alcohol amines (such as ethanol amine)
z may be 0 or any positive number.
solvent is any suitable polar solvent.

In one case L is

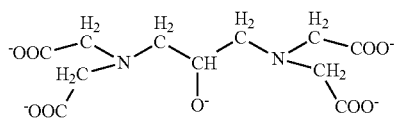

or a derivative thereof.

In one case M is selected from one or more of Fe, Al and Ga.

In another case M is selected from one or more of Mn, Ru, Eu, Zn, Zr, Cr, Co, Ni, Cu and V.

In one embodiment the solvent is selected from $H_2O$, methanol, ethanol, propanol, isopropanol. DMF, DMA, DMSO, acetonitrile and mixtures thereof.

The complex may be selected from and one or more of:
[$Fe_4(\mu$-O)($\mu$-OH)(hpdta)$_2$($O_2CNHC_4H_8NH_3$)$_2$]$^-$,
[$Fe_4(\mu$-O)($\mu$-OH)(hpdta)$_2$($O_2CNHC_2H_4NH_3$)$_2$]$^-$,
[$Fe_4(\mu$-O)($\mu$-OH)(hpdta)$_2$($O_2CNHC_3H_6NH_3$)$_2$]$^-$,
[$Fe_4(\mu$-O)($\mu$-OH)(hpdta)$_2$($O_2CNHC_5H_{10}NH_3$)$_2$]$^-$
[$Fe_4(\mu$-O)($\mu$-OH)(hpdta)$_2$($O_2CNHC_6H_{12}NH_3$)$_2$]$^-$,
[$Fe^{III}_4(\mu$-O)($\mu$-OH)(hpdta)$_2$($CO_3$)$_2$]$^{5-}$,
[$Al_4(\mu$-O)($\mu$-OH)(hpdta)$_2$($O_2CNHC_4H_8NH_3$)$_2$]$^-$,
[$Al_4(\mu$-O)($\mu$-OH)(hpdta)$_2$($O_2CNHC_2H_4NH_3$)$_2$]$^-$,
[$Al_4(\mu$-O)($\mu$-OH)(hpdta)$_2$($O_2CNHC_3H_6NH_3$)$_2$]$^-$,
[$Al_4$ ($\mu$-O)($\mu$-OH)(hpdta)$_2$($O_2CNHC_5H_{10}NH_3$)$_2$]$^-$
[$Ga_4(\mu$-O)($\mu$-OH)(hpdta)$_2$($O_2CNHC_6H_{12}NH_3$)$_2$]$^-$,
[$Ga_4(\mu$-O)($\mu$-OH)(hpdta)$_2$($CO_3$)$_2$]$^{5-}$,
[$Ga_4(\mu$-O)($\mu$-OH)(hpdta)$_2$($O_2CNHC_4H_8NH_3$)$_2$]$^-$,
[$Ga_4(\mu$-O)($\mu$-OH)(hpdta)$_2$($O_2CNHC_2H_4NH_3$)$_2$]$^-$,
[$Ga_4(\mu$-O)($\mu$-OH)(hpdta)$_2$($O_2CNHC_3H_6NH_3$)$_2$]$^-$,
[$Ga_4(\mu$-O)($\mu$-OH)(hpdta)$_2$($O_2CNHC_5H_{10}NH_3$)$_2$]$^-$, In one case the complexes are isolated as compound A or compound B or assemble readily in solutions from their metal salts and organic ligands at appropriate pH.

The uptake and release of carbon dioxide may be accomplished through change of pH and/or pressure and/or temperature of the environment of the complex of compound A or compound B.

In one case under alkaline conditions, the complex compound A captures $CO_2$ to form the complex compound B. In one embodiment the capturing occurs when the compound is dissolved in solution. In another embodiment the capture occurs when the compound is immobilised. The compound may be immobilised on a solid support.

In one case the complex of compound B is introduced into an acidic environment and undergoes a series of acid induced hydrolytic reactions, which results in the release of $CO_2$ and regeneration of the complex of compound B.

The $CO_2$ may be present in complex gas mixtures. The absorption and desorption process may be selective for $CO_2$.

The method may utilise hpdta ligands or derivatives thereof as a ligand which facilitates the immobilisation or stabilisation of the complex. The hpdta derivative may be of the formula:

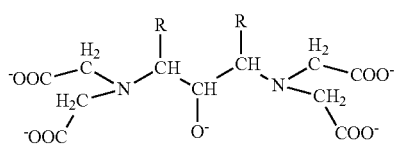

wherein functionalisations of R include one or two combinations of the following whereby one of the R groups is a H atom and the second R group can be 1-alkene and 1-alkyne side chains or alkyl chains with terminal carboxylic acid, the acid moieties may comprise acetic acid moieties and higher organic acid homologues.

The method may comprise the fixation or crafting of the complexes on a solid support. The support may be selected from a membrane, a silicate, an alumosilicate, a metal-organic, a framework, a metal, a metalloid and carbon. Fixation may be achieved through covalent bonding, coordination bonds and/or electrostatic interactions between the solid support and a complex. The covalent bonding may be achieved using copolymerisation. In one case the solid support is transferred between environments that facilitate uptake and release of $CO_2$.

The invention also provides a compound selected from:
{$Na(H_2O)_4$}$_5$[$Fe^{III}_4(\mu$-O)($\mu$-OH)(hpdta)$_2$($CO_3$)$_2$].sol,
($NH_2C_3H_6NH_3$)[$Fe_4(\mu$-O)($\mu$-OH)(hpdta)$_2$ ($O_2CNHC_3H_6NH_3$)$_2$].x sol,
($NH_2NH_3$)[$Fe_4(\mu$-O)($\mu$-OH)(hpdta)$_2$($O_2CNHNH_3$)$_2$].x sol,
($NH_2C_4H_8NH_3$)[$Fe_4(\mu$-O)($\mu$-OH)(hpdta)$_2$ ($O_2CNHC_4H_8NH_3$)$_2$].x sol,
($NH_2C_6H_{12}NH_3$)[$Fe_4(\mu$-O)($\mu$-OH)(hpdta)$_2$ ($O_2CNHC_6H_{12}NH_3$)$_2$].x sol,
($NH_2C_7H_{14}NH_3$)[$Fe_4(\mu$-O)($\mu$-OH)(hpdta)$_2$ ($O_2CNHC_7H_{14}NH_3$)$_2$].x sol,
($NHC_2H_4NC_4H_8NH_3$)[$Fe_4(\mu$-O)($\mu$-OH)(hpdta)$_2$ ($O_2CNHC_2H_4NC_4H_8NH_2$)$_2$].xsol,
w[$Fe_4(\mu$-O)($\mu$-OH)(hpdta)$_2$($O_2CNHC_3H_7$)$_2$].xsol,
w[$Fe_4(\mu$-O)($\mu$-OH)(hpdta)$_2$ ($O_2CNHCH_2CH_2HNCH_2CH_2NH_3$)$_2$].xsol,
w[$Fe_4(\mu$-O)($\mu$-OH)(hpdta)$_2$($O_2CNHCH_2CH_2OH$)$_2$].xsol.

The invention also provides a compound selected from:
w[$Al^{III}_4(\mu$-O)($\mu$-OH)(hpdta)$_2$($CO_3$)$_2$].sol,
w[$Al_4(\mu$-O)($\mu$-OH)(hpdta)$_2$($O_2CNHC_2H_4NH_3$)$_2$].x sol,
w[$Al_4(\mu$-O)($\mu$-OH)(hpdta)$_2$($O_2CNHNH_3$)$_2$].x sol,
w[$Al_4(\mu$-O)($\mu$-OH)(hpdta)$_2$($O_2CNHC_4H_8NH_3$)$_2$].x sol,
w[$Al_4(\mu$-O)($\mu$-OH)(hpdta)$_2$($O_2CNHC_6H_{12}NH_3$)$_2$].x sol,
w[$Al_4(\mu$-O)($\mu$-OH)(hpdta)$_2$($O_2CNHC_7H_{14}NH_3$)$_2$].x sol,
w[$Al_4(\mu$-O)($\mu$-OH)(hpdta)$_2$($O_2CNHC_2H_4NC_4H_8NH_2$)$_2$]. xsol,
w[$Al_4(\mu$-O)($\mu$-OH)(hpdta)$_2$($O_2CNHC_3H_7$)$_2$].xsol,
w[$Al_4(\mu$-O)($\mu$-OH)(hpdta)$_2$ ($O_2CNHCH_2CH_2HNCH_2CH_2NH_3$)$_2$].xsol,
w[$Al_4(\mu$-O)($\mu$-OH)(hpdta)$_2$($O_2CNHCH_2CH_2OH$)$_2$].xsol.

The invention further provides a compound selected from:
w[$Cu^{III}_4(\mu$-O)($\mu$-OH)(hpdta)$_2$($CO_3$)$_2$].sol,
w[$Cu_4(\mu$-O)($\mu$-OH)(hpdta)$_2$($O_2CNHC_2H_4NH_3$)$_2$].x sol,
w[$Cu_4(\mu$-O)($\mu$-OH)(hpdta)$_2$($O_2CNHCH_4NH_3$)$_2$].x sol,
w[$Cu_4(\mu$-O)($\mu$-OH)(hpdta)$_2$($O_2CNHNH_3$)$_2$].x sol,
w[$Cu_4(\mu$-O)($\mu$-OH)(hpdta)$_2$($O_2CNHC_4H_8NH_3$)$_2$].x sol,
w[$Cu_4(\mu$-O)($\mu$-OH)(hpdta)$_2$($O_2CNHC_6H_{12}NH_3$)$_2$].x sol,
w[$Cu_4(\mu$-O)($\mu$-OH)(hpdta)$_2$($O_2CNHC_7H_{14}NH_3$)$_2$].x sol,
w[$Cu_4(\mu$-O)($\mu$-OH)(hpdta)$_2$($O_2CNHC_2H_4NC_4H_8NH_2$)$_2$]. xsol,
w[$Cu_4(\mu$-O)($\mu$-OH)(hpdta)$_2$($O_2CNHC_3H_7$)$_2$].xsol,
w[$Cu_4(\mu$-O)($\mu$-OH)(hpdta)$_2$ ($O_2CNHCH_2CH_2HNCH_2CH_2NH_3$)$_2$].xsol,
w[$Cu_4(\mu$-O)($\mu$-OH)(hpdta)$_2$($O_2CNHCH_2CH_2OH$)$_2$].xsol.

In one aspect the invention provides a compound selected from:
w[$Ga^{III}_4(\mu$-O)($\mu$-OH)(hpdta)$_2$($CO_3$)$_2$].sol,
w[$Ga_4(\mu$-O)($\mu$-OH)(hpdta)$_2$($O_2CNHC_2H_4NH_3$)$_2$].x sol,
w[$Ga_4(\mu$-O)($\mu$-OH)(hpdta)$_2$($O_2CNHC_2H_4NH_3$)$_2$].x sol,
w[$Ga_4(\mu$-O)($\mu$-OH)(hpdta)$_2$($O_2CNHNH_3$)$_2$].x sol, w[Ga$_4$(μ-O)(μ-OH)(hpdta)$_2$(O$_2$CNHC$_4$H$_8$NH$_3$)$_2$].x sol,
w[Ga$_4$(μ-O)(μ-OH)(hpdta)$_2$(O$_2$CNHC$_6$H$_{12}$NH$_3$)$_2$].x sol,
w[Ga$_4$(μ-O)(μ-OH)(hpdta)$_2$(O$_2$CNHC$_7$H$_{14}$NH$_3$)$_2$].x.sol,
w[Ga$_4$(μ-O)(μ-OH)(hpdta)$_2$(O$_2$CNHC$_2$H$_4$NC$_4$H$_8$NH$_2$)$_2$].xsol,
w[Ga$_4$(μ-O)(μ-OH)(hpdta)$_2$(O$_2$CNHC$_3$H$_7$)$_2$].xsol,
w[Ga$_4$(μ-Q)(μ-OH)(hpdta)$_2$(O$_2$CNHCH$_2$CH$_2$HNCH$_2$CH$_2$NH$_3$)$_2$].xsol,
w[Ga$_4$(μ-O)(μ-OH)(hpdta)$_2$(O$_2$CNHCH$_2$CH$_2$OH$_2$].xsol.

In another aspect the invention provides a compound selected from:
w[Mn$_4$(μ-O)(μ-OH)(hpdta)$_2$(CO$_3$)$_2$].sol,
w[Mn$_4$(μ-O)(μ-OH)(hpdta)$_2$(O$_2$CNHC$_2$H$_4$NH$_3$)$_2$].x sol,
w[Mn$_4$(μ-O)(μ-OH)(hpdta)$_2$(O$_2$CNHC$_2$H$_4$NH$_3$)$_2$].x sol,
w[Mn$_4$(μ-O)(μ-OH)(hpdta)$_2$(O$_2$CNHNH$_3$)$_2$].x sol,
w[Mn$_4$(μ-O)(μ-OH)(hpdta)$_2$(O$_2$CNHC$_4$H$_8$NH$_3$)$_2$].x sol,
w[Mn$_4$(μ-O)(μ-OH)(hpdta)$_2$(O$_2$CNHC$_6$H$_{12}$NH$_3$)$_2$].x sol,
w[Mn$_4$(μ-O)(μ-OH)(hpdta)$_2$(O$_2$CNHC$_7$H$_{14}$NH$_3$)$_2$].x sol,
w[Mn$_4$(μ-O)(μ-OH)(hpdta)$_2$(O$_2$CNHC$_2$H$_4$NC$_4$H$_8$NH$_2$)$_2$].xsol,
w[Mn$_4$(μ-O)(μ-OH)(hpdta)$_2$(O$_2$CNHC$_3$H$_7$)$_2$].xsol,
w[Mn$_4$(μ-O)(μ-OH)(hpdta)$_2$(O$_2$CNHCH$_2$CH$_2$HNCH$_2$CH$_2$NH$_3$)$_2$].xsol,
w[Mn$_4$(μ-O)(μ-OH)(hpdta)$_2$(O$_2$CNHCH$_2$CH$_2$OH)$_2$].xsol.

In a further aspect the invention provides a compound selected from:
w[Cr$_4$(μ-O)(μ-OH)(hpdta)$_2$(CO$_3$)$_2$].sol,
w[Cr$_4$(μ-O)(μ-OH)(hpdta)$_2$(O$_2$CNHC$_2$H$_4$NH$_3$)$_2$].x sol,
w[Cr$_4$(μ-O)(μ-OH)(hpdta)$_2$(O$_2$CNHC$_2$H$_4$NH$_3$)$_2$].x sol,
w[Cr$_4$(μ-O)(μ-OH)(hpdta)$_2$(O$_2$CNHNH$_3$)$_2$].x sol,
w[Cr$_4$(μ-O)(μ-OH)(hpdta)$_2$(O$_2$CNHC$_4$H$_8$NH$_3$)$_2$].x sol,
w[Cr$_4$(μ-O)(μ-OH)(hpdta)$_2$(O$_2$CNHC$_6$H$_{12}$NH$_3$)$_2$].x sol,
w[Cr$_4$(μ-O)(μ-OH)(hpdta)$_2$(O$_2$CNHC$_7$H$_{14}$NH$_3$)$_2$].x sol,
w[Cr$_4$(μ-O)(μ-OH)(hpdta)$_2$(O$_2$CNHC$_2$H$_4$NC$_4$H$_8$NH$_2$)$_2$].x sol,
w[Cr$_4$(μ-O)(μ-OH)(hpdta)$_2$(O$_2$CNHC$_3$H$_7$)$_2$].x sol,
w[Cr$_4$(μ-O)(μ-OH)(hpdta)$_2$(O$_2$CNHCH$_2$CH$_2$HNCH$_2$CH$_2$NH$_3$)$_2$].x sol.
w[Co$_4$(μ-O)(μ-OH)(hpdta)$_2$(O$_2$CNHC$_2$H$_4$NH$_3$)$_2$].x sol.

The invention also provides the following species:
[Fe$_4$(μ-O)(μ-OH)(hpdta)$_2$(H$_2$O)$_4$]$^-$,
[Fe$_4$(μ-O)(μ-OH)(hpdta)$_2$(O$_2$CNHC$_2$H$_4$NH$_3$)$_2$]$^-$,
[Al$_4$(μ-O)(μ-OH)(hpdta)$_2$(O$_2$CNHC$_3$H$_6$NH$_3$)$_2$]$^-$,
[Ga$_4$ (μ-O)(μ-OH)(hpdta)$_2$ (O$_2$CNHC$_4$H$_8$NH$_2$)$_2$]$^-$
[Fe$^{III}_4$(μ-O)(μ-OH)(hpdta)$_2$(CO$_3$)$_2$]$^{5-}$.

In another aspect the invention provides the use of any of the above compounds and active species for absorption of carbon dioxide.

In a further aspect the invention provides the use of any of the above compounds for reversible absorption and release of carbon dioxide.

The complexes may be fixed or crafted to the support. The fixation or crafting of the complexes on a solid support may be achieved through covalent bonding, coordination bonds and/or electrostatic interactions between a solid support and the complex. The support may be selected from membranes, silicates, alumosilicates, metal-organic, frameworks, metals and metalloids, carbons and the like.

In one aspect the invention provides a method for reversible absorption and release of carbon dioxide using tetranuclear transition metal complexes.

The following compounds may be used to promote the reversible capture and release of carbon dioxide.

w[M$_4$(μ-O)x(μ-OH)y(L)$_2$(H$_2$O)$_4$]·z(solvent)    Compound A w[M$_4$(μ-O)x(μ-OH)y(L)$_2$(O$_2$CR$_1$)$_1$(O$_2$CR$_2$)$_1$]·z(solvent)    Compound B w=any ion or mixture of ions (e.g. ammonium ions and derivatives, alkali or alkali earth metal ions) in appropriate stoichiometries for compounds A or B to be electronically neutral.

M=is a divalent or trivalent metal ion or any combination of two or more divalent and trivalent metal ions.

x and y are numerical values the sum of which equals to 2

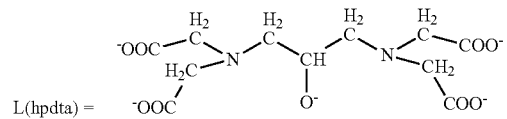

L(hpdta) =

R$_1$ and R$_2$=any sidegroup or combination of two sidegroups from the following list:
an oxygen atom, OH group, hydrazine, ammonia, alkyl chains, or any primary, secondary or tertiary aliphatic or aromatic amines and their derivatives including diamines, triamines or alcohol amines (e.g. ethanol amine).

z=any value; solvent=all common polar solvents (including H$_2$O, methanol, ethanol, acetonitrile and etc.) or mixture of these.

The invention applies to complexes that can be isolated as compound A or compound B above or assemble readily in solutions from their metal salts and organic ligands at appropriate pH.

M=Fe, Al, Mn, Cu, Zn have the following advantages
high affinity towards carbon dioxide
earth abundant
inexpensive
non toxic
Lewis acidity
can work in aqueous systems M=Ga, Ru, have the following advantages
high affinity towards carbon dioxide
non toxic
Lewis acidity
can work in aqueous systems M=Cr, Co, Ni appear to have a moderate affinity towards CO$_2$.

M=V, Mo, W have been investigated for the purpose of CO$_2$ entrapment, however it appears that the oxidation state +III at the pHs required for CO$_2$ entrapment for these metals in this coordination environment is not particularly stable.

M=Ag, Eu, Tb, Au Pt, Pd are not currently preferred because their coordination behaviour is not suitable to form appropriate complexes.

M=Re, Rh are not currently preferred because of their high cost.

In the invention the uptake and release of carbon dioxide is accomplished through change of pH of the environment of the complexes of compound A and B. Additionally temperature and pressure changes aid the uptake and release of carbon dioxide.

Under alkaline conditions, the complex in compound A captures CO$_2$ highly efficiently to form the complex in compound B. The capturing process can occurs when the compounds are dissolved in solution or when they are generated in situ from their corresponding starting materials or when the complexes are immobilised on solid supports. When the complex of compound B is introduced into an acidic environment, it undergoes a series of acid induced hydrolytic reactions, which results in the release of $CO_2$ and regeneration of the complexes of compound A. The process can be cycled and subsequent re-introduction of compound A into an alkaline environment results in the entrapment of $CO_2$ and reformation of compound B. For this absorption and desorption process $CO_2$ can be supplied in complex gas mixtures. The absorption and desorption process is selective for $CO_2$. The $CO_2$ may be provided in complex gas mixtures and the absorption process occurs selectively. The described method also allows the capture of atmospheric $CO_2$.

The method utilises the hpdta ligand and derivatives which facilitate the immobilisation of complexes of compound A and B, for example onto solid supports. An example of a derivative of the ligand is shown below. Exemplary functionalisations of R include, but are not limited to, one or two combinations of the following whereby one of the R groups is a H atom and the second R group can be 1-alkene and 1-alkyne side chains or alkyl chains with terminal carboxylic acid, nitrile, aldehyde, amine or nitro functions. Similar functionalisations may also be introduced at the methylene groups of the acid moieties of the organic ligands. These acid moieties are not only restricted to acetic acid moieties but also include higher organic acid homologues.

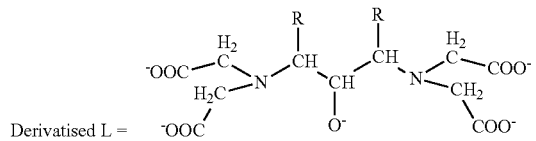

The ligand hpdta offers the following advantages:
commercially available
relatively inexpensive,
the ligand is potentially heptadentate which allows for the coordination of two metal centres per hpdta molecule (aids the capturing efficiency),
it coordinates with $M^{II}/M^{III}$ ions to form a symmetrical tetranuclear complex (it is easier to capture and release $CO_2$ when both compound A and compound B are symmetrical—the $CO_2$ trapping sites are easily accessible)
the $CO_2$ molecules are trapped as auxiliary ligands which allows for the compound to retain topographical integrity upon acid induced release of $CO_2$. (If the $CO_2$ molecules were trapped as a bridging ligand between two metal ions then it would be difficult to retain a topological integrity and would be extremely difficult to predict and demonstrate the reversible capabilities of the compound)
the pKa is relatively low, as compared to other ligands, which allows for the adjustment of the pH to pH 2 without protonation of the ligand (upon protonation of the ligand the compound would disintegrate as the ligands coordination sites would be occupied by protons and therefore would be no longer available to stabilise the M ions. If the $pK_a$ was a higher value then it may not be possible to reversibly capture and release the $CO_2$ as the ligands would precipitate and the complex would be unstable at the pH at which the $CO_2$ is released and compound A is formed.

Bases/amines are advantageous because they are commercially available, inexpensive and are readily utilised within industry. They facilitate the uptake of $CO_2$ from gas mixtures or the environment. During the absorption process $CO_2$ reacts to give carbamates, hydrogen carbonate, carbonate or related species.

In another aspect the invention provides the fixation or crafting of the above-mentioned complexes of compounds A and B on solid supports including membranes, silicates, alumosilicates, metal-organic, frameworks, metals and metalloids, carbons and the like.

Fixation is achieved through covalent bonds (co-polymerisation methods), coordination bonds or electrostatic interactions between solid support and complexes. This allows us to implement the invention into green technology devices and systems whereby solid supports are transferred between two distinct environments that facilitate uptake and release of $CO_2$ (e.g. two vessels with different pH conditions). An example of one possible device illustrated in FIG. 6 and will be described in more detail below.

BRIEF DESCRIPTION OF THE DRAWINGS

The invention will be more clearly understood from the following description thereof, given by way of example only, with reference to the accompanying drawings, in which.

DETAILED DESCRIPTION

Figure 1:
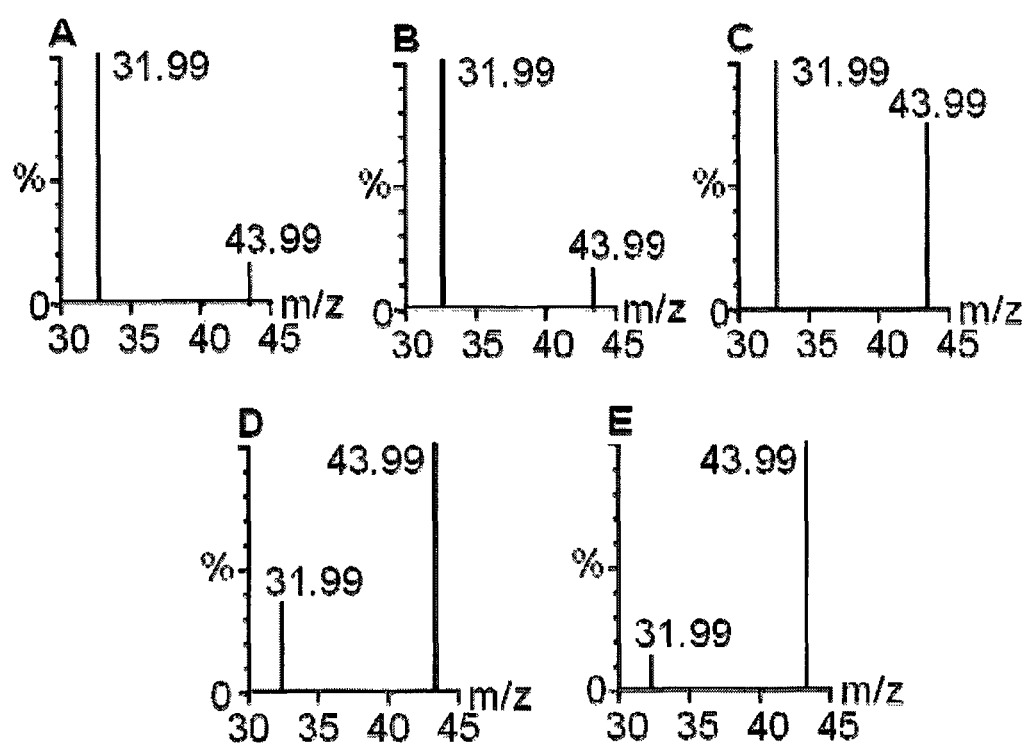
FIG. 1 is the Gas chromatography Mass spectra (GC-MS) recorded for headspace of GC-MS vial containing (enH) [$Fe_4(\mu\text{-}O)(\mu\text{-}OH)(hpdta)_2(O_2CNHC_4H_8NH_3)_2$]$\cdot 6.5H_2O$ dissolved at pH 9.4. pH 7, pH 5.4, pH 4 and pH 2.2.

The invention will be more clearly understood from the following examples.

Method for the Capturing of $CO_2$ Using Tetranuclear Metal Complexes

Organic ligands that stabilise tetranuclear metal complexes in which coordination sites that are occupied by solvent molecules provide binding sites for carbonates, hydrogen carbonates, carboxylates and carbamates. The aminocarboxylic acid hpdta ligand was chosen because it is commercially available. The method may also apply to structurally related ligands that use N-containing groups (e.g. pyridines, benzimidazoles, tetrazoles and etc.), phosphates, phosphonates, aldehydes or nitriles instead of the carboxylic acid functions. The central alcohol function of the ligands bridges between the metal centres and may be replaced by other functionalities that facilitate this mode (methoxides, carboxylic acid function and etc.).

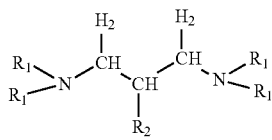

$R_1$: acetate moieties or other alkyl moiety containing N-containing functionalities (e.g. pyridines, benzimidazoles, tetrazoles and etc.), phosphates, phosphonates, aldehydes or nitriles.

$R_2$: hydroxyl, methoxide, carboxylic acid function or other bridging group.

The $Fe_4(\mu\text{-}O)(1\text{-}OH)(hpdta)_2(H_2O)_4]^-$ species contained within a material (e.g. in $(NH_4)[Fe_4(\mu\text{-}O)(\mu\text{-}OH)(hpdta)_2(H_2O)_4].2.5H_2O$ and $[\{Fe^{III}_4(\mu\text{-}O)\text{-}(\mu\text{-}OH)(hpdta)_2(H_2O)_4\}_2Fe^{II}(H_2O)_4].21H_2O)$ or in a solution is regarded as an important complex for the capture of $CO_2$.

Synthesis of $(NH_4)[Fe(\mu\text{-}O)(\mu\text{-}OH)(hpdta)_2(H_2O)_4]$ 12.5$H_2O$ 0.081 g (0.25 mmol) $H_5$hpdta was dissolved in 1 ml distilled water by addition of 1.3 ml ammonia solution (2 M). The ligand was then added to a solution of 1.25 ml of iron(III)nitrate nonahydrate (0.4 M). Addition of 1 ml dimethylacetamide as cosolvent and slow evaporation of the solvent led to the formation of orange red crystals of 3 after 5 days. Yield: 0.064 g [43% based on $Fe(NO_3)_3.9H_2O$]. Elemental analysis, calculated for $C_{22}H_{58}Fe_4N_5O_{33.5}$ which corresponds to the crystallographically determined formulation with the loss of three water molecules: C, 22.94%; H, 5.07%; N, 6.08%. found: C, 22.86%; H, 5.04%; N, 6.14%. IR (KBr) (cm21): 3423 (s, br), 3198 (sh), 1637 (vs), 1384 (vs), 919 (m), 742 (m), 606 (m).

Synthesis of $[\{Fe^{III}_4(\mu\text{-}O)\text{-}(\mu\text{-}OH)(hpdta)_2(H_2O)_4\}_2Fe^{II}(H_2O)_4].21H_2O$ 0.081 g (0.25 mmol) $H_5$hpdta was dissolved in 5 ml distilled water by addition of 0.5 ml ammonia solution (2 M). 5 ml of an aqueous $FeCl_3.6H_2O$ solution (0.1 M) was added to the stirring ligand. Slow evaporation of the solvent led to the formation of orange crystals. The reaction product was filtered, washed with ether and dried at room temperature. The yield was 0.046 g. Elemental analysis, calculated for $C_{44}H_{120}Fe_9N_8O_{73}$ which corresponds to the crystallographically determined formulation with the loss of three water molecules: C, 21.73%; H, 4.97%; N, 4.61%. found: C, 21.63%; H, 5.03%; N, 4.71%. IR (KBr): 3403 (s, br), 3198 (sh), 1637 (vs), 1384 (vs), 919 (m), 742 (m), 606 (m).

The reported iron compound that is the result of the fixation of $CO_2$ is $(enH)[Fe_4(\mu\text{-}O)(\mu\text{-}OH)(hpdta)_2(O_2CNHC_2H_4NH_3)_2].6.5H_2O$.

Synthesis of $(enH)[Fe_4(\mu\text{-}O)(\mu\text{-}OH)(hpdta)_2(O_2CNHC_2H_4NH_3)_2].6.5H_2O$ 0.081 g (0.25 mmol) $H_5$hpdta and 0.202 g (0.5 mmol) $Fe(NO_3)_3.9H_2O$ were dissolved in 5 ml distilled water by dropwise addition of ethylenediamine up to pH 10.1. Addition of 5 ml dimethylacetamide led to the formation of green crystals within 8 days. Yield: 0.042 g [26% based on $Fe(NO_3)_3.9H_2O$]. Elemental analysis, calculated for $C_{30}H_{63}Fe_4N_{10}O_{30.5}$: C, 28.26%; H, 4.98%; N, 10.98%. found: C, 28.53%; H, 4.91%; N, 10.71%. IR (KBr) (cm): 3418 (s, br), 2958 (s), 2925 (s), 1645 (vs), 1568 (s), 1511 (s), 1441 (m), 1378 (vs), 1339 (s), 1256 (m), 1163 (m), 1098 (m), 1049 (m), 1002 (m), 972 (w), 934 (s), 913 (s), 867 (w), 795 (w), 737 (m), 669 (m).

It has been reported that $(H_3O)[Al_4(\mu\text{-}O)(\mu\text{-}OH)(hpdta)_2(O_2CNHC_3H_6NH_3)_2].13H_2O.2DMA$ and $(pipH)[Ga_4(\mu\text{-}O)(\mu\text{-}OH)(hpdta)_2(O_2CNHC_4H_8NH_2)_2].14H_2O$ are the result of the fixation of $CO_2$ Synthesis of $(H_3O)[Al_4(\mu\text{-}O)(\mu\text{-}OH)(hpdta)_2(O_2CNHC_3H_6NH_3)_2].13H_2O.2DMA$ 0.081 g (0.25 mmol) $H_5$hpdta and 0.188 g (0.5 mmol) $Al(NO_3)_3.9H_2O$ were dissolved in 6 ml distilled water by slow addition of 1,3-diaminopropane (ca. 0.1 ml) to a pH value of 8.6. Addition of 5 ml dimethylacetamide led to the formation of colourless plates within 2 days. Yield: 0.136 g [76% based on $Al(NO_3)_3.9H_2O$]. Elemental analysis, calculated for $C_{38}H_{86}Al_4N_{10}O_{36}$ (corresponds to the crystallographically determined formulation with the loss of four water molecules): C, 33.39%; H, 6.34%; N, 10.25%. found: C, 33.42%; H, 6.48%; N, 10.30%. IR (KBr) (cm): 3427 (s, br), 1652 (vs), 1589 (s), 1531 (ms), 1385 (vs), 926 (m), 840 (m).

Synthesis of $(pipH)[Ga_4(\mu\text{-}O)(\mu\text{-}OH)(hpdta)_2(O_2CNHC_4H_8NH_2)_2].14H_2O$ 0.081 g (0.25 mmol) of $H_5$hpdta was dissolved in a mixture of 1.5 ml water and 1 ml of an aqueous piperazine solution (1 M). The resulting solution was added with stirring to a solution of 0.400 g (1 mmol) gallium nitrate octahydrate dissolved in 2.5 ml water. The pH was adjusted to 9.0 by dropwise addition of an aqueous piperazine solution (1 M). Addition of 5 ml dimethylacetamide followed by slow evaporation of the solvent gave small amount of colourless crystals of 10 after approximately 1 month and a cloudy, gelatinous substance. Yield: 0.02 g (10% based on $H_5$hpdta). Elemental analysis: calculated for $C_{36}H_{80}Ga_4N_{10}O_{35}$, which corresponds to the crystallographically determined formulation with the loss of three water molecules from the structure: C, 28.98%. H, 5.40%; N, 9.39%. found: C, 29.21%; H, 5.54%; N, 9.51%. IR (KBr) (cm): 3444 (vs, br), 2926 (m), 1642 (s), 1535 (m), 1384 (s), 1298 (m), 1259 (m), 1055 (w), 1032 (w), 1000 (w), 941 (w), 914 (w), 876 (vw), 745 (w), 641 (w).

The isolation of $Na_6[Fe^{III}_4(\mu\text{-}O)(\mu\text{-}OH)(hpdta)_2(CO_3)_2]\cdot 20H_2O$ has been previously reported but it was synthesised by the addition of carbonate or hydrogen carbonate. In previous reports it has not been demonstrated that this compound forms upon fixation of $CO_2$.

Synthesis of $Na_6[Fe^{III}_4(\mu\text{-}O)(\mu\text{-}OH)(hpdta)_2(CO_3)_2]\cdot 20H_2O$ This complex was prepared by the reaction of $H_5$hpdta with an aqueous slurry of Fe(OH), followed by the addition of $NaHCO_3$. 5.4 g (20 mmol) of $FeCl_3\cdot 6H_2O$ in 100 mL of $H_2O$ with a solution of 2.4 g (60 mmol) of NaOH in 15 mL of $H_2O$, isolated by centrifugation, and freed of chloride by stirring with $H_2O$ and recentrifuging (4 times). A slurry of the purified Fe(OH), in 100 mL of $H_2O$ was reacted with 3.22 g (10 mmol) of 2 for 1 h at 70° C. Solid $NaHCO_3$, (1.68 g, 20 mmol) was added slowly (effervescence) to the resulting yellow solution; the pH increased from 1.5 to 8.0 and the colour changed to brown-green. After the solution was stirred for 12 h. the pH increased to 8.5. The solution was filtered through a fine frit and reduced in volume to 50 mL by rotaevaporation. Small, brown-green, tablet-shaped crystals deposited over a 3-day period from a mixture of 15 mL of the above concentrate and 50 mL of methoxyethanol that was placed in a dessicator containing $CaCl_2$. The crystals were collected by filtration and dried briefly by blotting (yield 40%). The crystals crack upon exposure to air for more than a few minutes or to water-miscible organic solvents, but they are stable for at least several hours under mineral oil. Careful microscopic examination of the product established that a single crystalline phase was obtained.

Examples of Compounds that Capture $CO_2$: Synthesis of New Analogues of Compound B (Either as Solids or Generated In Situ).
General Synthesis:

0.081 g (0.25 mmol) hydroxypropane-1,3-diamine-N,N,N',N'-tetraacetic acid ($H_5$hpdta) was dissolved in 5 ml of deionised water by addition of 0.5 ml base. x g (0.5 mmol) $M^{III}/Mn^{II}$ salt was added to the reaction mixture followed by 0.25 ml base to adjust the pH to 8.5.

If a $M^{II}$ ion was used as a starting material, the final reaction mixture was purged with air for 30 minutes to ensure complete oxidation of $M^{II}$ ion to $M^{III}$.

If it was necessary to obtain single crystals or powders for solid state characterisation of the compounds dimethylacetamide (DMA) was added to the solution and solid material formed within 2-5 days.

Mixed metal compounds can also be formed using this general procedure by addition of a mixture of M ion sources. However, the sum of the individual ion concentrations must equal 0.5 mmol. For example in the synthesis of an analogue of compound B which has 2 $Al^{III}$ and 2 $Fe^{III}$ ions in its tetra nuclear core 0.25 mmol $Al^{III}$ salt and 0.25 mmol of $Fe^{III}$ salt would be added to the reaction mixture.

The syntheses of specific examples of Fe, Al, Cu, Ga, Mn, analogues of compound B are described below. These compounds form upon adsorption of atmospheric $CO_2$.
Fe Analogaes:

Example 1 w[$F^{III}_4(\mu\text{-}O)(\mu\text{-}OH)(hpdta)_2(CO_3)_2$].sol (1)

0.081 g (0.25 mmol) $H_5$hpdta was dissolved in 5 ml of deionised water by addition of 0.5 ml sodium hydroxide solution (2M). 0.202 g (0.5 mmol) $Fe(NO_3)_3\cdot 9H_2O$ was added to the reaction mixture followed by 0.25 ml sodium hydroxide solution (0.1M) to adjust the pH to 8.5. Co-evaporation with 2.5 ml dimethylacetamide led to the formation of green crystals of 1 after 4 days. The compound was dried for 24 hours at 120° C. Yield=75% Chemical analysis. for $\{Na(H_2O)_4\}_5[Fe^{III}_4(\mu\text{-}O)(\mu\text{-}OH)(hpdta)_2(CO_3)_2]\cdot 12H_2O$ Calculated: C %, 22.12; H %, 3.2; N %, 4.29; Fe %, 17.32; Na %, 7.37. Found: C %, 21.49; H %, 2.66; N %, 3.94; Fe %, 16.41; Na %, 7.3. FTIR (cm$^{-1}$) $v_{max}$: 3372.39 (s, br), 2958 (s), 2925 (s), 1606.81 (vs), 1477.02 (br, m), 1325.17 (s), 1165.21 (m), 1055.10 (m), 1003.57 (m), 915.96 (s), 853.09 (w).

Example 2 w[$Fe_4(\mu\text{-}O)(\mu\text{-}OH)(hpdta)_2(O_2CNHC_3H_6NH_3)_2$].x sol (2)

0.081 g (0.25 mmol) $H_5$hpdta was dissolved in 5 ml of deionised water by addition of 1,4-diaminopropane. 0.202 g (0.5 mmol) $Fe(NO_3)_3\cdot 9H_2O$ was added to the reaction mixture followed by 0.25 ml 1,4-diaminopropane to adjust the pH to 8.5. Co-evaporation with 2.5 ml dimethylacetamide led to the formation of a green powder of 2. The compound was dried for 24 hours at 120° C. Yield=35 mg. FTIR (cm$^{-1}$) $v_{max}$: 3327 (s, br), 2934 (s), 2890 (s), 1622 (s), 1567 (s), 1510 (s), 1366 (s), 1240 (s), 1219 (s), 999 (s), 911(s), 863 (s), 652 (m).

Example 3 w[$Fe_4(\mu\text{-}O)(\mu\text{-}OH)(hpdta)_2(O_2CNHNH_3)_2$].x sol (3)

0.081 g (0.25 mmol) $H_5$hpdta was dissolved in 5 ml of deionised water by addition of hydrazine. 0.202 g (0.5 mmol) $Fe(NO_3)_3\cdot 9H_2O$ was added to the reaction mixture followed by 0.25 ml hydrazine to adjust the pH to 8.5. Co-evaporation with 2.5 ml dimethylacetamide led to the formation of small green crystals of 3. The crystals formed after 3 days but were unsuitable for single x-ray characterisation. The compound was dried for 24 hours at 120° C. Yield=35 mg. $(NH_2NH_3)[Fe_4(\mu\text{-}O)(\mu\text{-}OH)(hpdta)_2(O_2CNHNH_3)_2]$.x sol; FTIR (cm$^{-1}$) $v_{max}$: 3327 (s, br), 2934 (s), 2890 (s), 1622 (s), 1567 (s), 1510 (s), 1366 (s), 1240 (s), 1219 (s), 999 (s), 911(s), 863 (s), 652 (m).

Example 4 w[$Fe_4(\mu\text{-}O)(\mu\text{-}OH)(hpdta)_2(O_2CNHC_4H_8NH_3)_2$].x sol (4)

0.081 g (0.25 mmol) $H_5$hpdta was dissolved in 5 ml of deionised water by addition of 1,4-diaminobutane. 0.202 g (0.5 mmol) Fe(NO$_3$)$_3$.9H$_2$O was added to the reaction mixture followed by 0.25 ml 4-diaminobutane to adjust the pH to 8.5. Co-evaporation with 2.5 ml dimethylacetamide led to the formation of small green crystals of 4. The crystals formed after 3 days but were unsuitable for single x-ray characterisation. The compound was dried for 24 hours at 120° C. Yield=35 mg. (NH$_2$C$_4$H$_8$NH$_3$)[Fe$_4$(μ-O)(μ-OH)(hpdta)$_2$(O$_2$CNHC$_4$H$_8$NH$_3$)$_2$].xsol; FTIR (cm$^{-1}$) ν$_{max}$: 3327 (s, br), 2934 (s), 2890 (s), 1622 (s), 1567 (s), 1510 (s), 1366 (s), 1240 (s), 1219 (s), 999 (s), 911(s), 863 (s), 652 (m).

Example 5 w[Fe$_4$(μ-O)(μ-OH)(hpdta)$_2$(O$_2$CNHC$_6$H$_{12}$NH$_3$)$_2$].x sol (5)

0.081 g (0.25 mmol) H$_5$hpdta was dissolved in 5 ml of deionised water by addition of hexamethylenediamine. 0.202 g (0.5 mmol) Fe(NO$_3$)$_3$.9H$_2$O was added to the reaction mixture followed by 0.25 ml hexamethylenediamine to adjust the pH to 8.5. Co-evaporation with 2.5 ml dimethylacetamide led to the formation of small green crystals of 5. The crystals formed after 3 days but were unsuitable for single x-ray characterisation. Yield=63 mg. (NH$_2$C$_6$H$_{12}$NH$_3$)[Fe$_4$(μ-O)(μ-OH)(hpdta)$_2$ (O$_2$CNHC$_6$H$_{12}$NH$_3$)$_2$].x sol; FTIR (cm$^{-1}$) ν$_{max}$: 3325 (s, br), 2931 (s), 2919 (s), 1616 (vs), 1537 (s), 1500 (s), 1367 (vs), 1311 (s), 1162 (m), 1089 (m), 911(s), 863 (br), 663 (s).

Example 6 w[Fe$_4$(μ-O)(μ-OH)(hpdta)$_2$(O$_2$CNHC$_7$H$_{14}$NH$_3$)$_2$].x sol (6)

0.081 g (0.25 mmol) H$_5$hpdta was dissolved in 5 ml of deionised water by addition of heptamethylenediamine. 0.202 g (0.5 mmol) Fe(NO$_3$)$_3$.9H$_2$O was added to the reaction mixture followed by 0.25 ml heptamethylenediamine to adjust the pH to 8.5. Co-evaporation with 2.5 ml dimethylacetamide led to the formation of small green crystals of 6. The crystals formed after 3 days but were unsuitable for single x-ray characterisation. Yield=43 mg. (NH$_2$C$_7$H$_{14}$NH$_3$)[Fe$_4$(μ-O)(μ-OH)(hpdta)$_2$ (O$_2$CNHC$_7$H$_{14}$NH$_3$)$_2$].x sol; FTIR (cm$^{-1}$) ν$_{max}$: 3325 (s, br), 2931 (s), 2919 (s), 1616 (vs), 1537 (s), 1500 (s), 1367 (vs), 1311 (s), 1162 (m), 1089 (m), 911(s), 863 (br), 663 (s).

Example 7 w[Fe$_4$(μ-O)(μ-OH)(hpdta)$_2$ (O$_2$CNHC$_2$H$_4$NC$_4$H$_{14}$NH$_2$)$_2$].x sol (7)

0.081 g (0.25 mmol) H$_5$hpdta was dissolved in 5 ml of deionised water by addition of 1-(2-aminoethyl)piperazine. 0.202 g (0.5 mmol) Fe(NO$_3$)$_3$.9H$_2$O was added to the reaction mixture followed 1-(2-aminoethyl)piperazine to adjust the pH to 8.5. Co-evaporation with 2.5 ml dimethylacetamide led to the formation of small green crystals of 6. The crystals formed after 3 days but were unsuitable for single x-ray characterisation. The compound was dried for 24 hours at 120° C. Yield=44 mg.
(NHC$_2$H$_4$NC$_4$H$_8$NH$_3$)[Fe$_4$(μ-O)(μ-OH)(hpdta)$_2$ (O$_2$CNHC$_2$H$_4$NC$_4$H$_8$NH$_2$)$_2$].xsol; FTIR (cm$^{-1}$) ν$_{max}$: 3376 (s, br), 2931 (s), 2919 (s), 1623 (s), 1504 (s), 1439 (m), 1369 (vs), 1297 (s), 998 (s), 911 (s), 666 (vs).

Example 8 w[Fe$_4$(μ-O)(μ-OH)(hpdta)$_2$(O$_2$CNHC$_3$H$_7$)$_2$].xsol (8)

0.081 g (0.25 mmol) H$_5$hpdta was dissolved in 5 ml of deionised water by addition of propylamine. 0.202 g (0.5 mmol) Fe(NO$_3$)$_3$.9H$_2$O was added to the reaction mixture followed by propylamine to adjust the pH to 8.5.

Example 9 w[Fe$_4$(μ-O)(μ-OH)(hpdta)$_2$ (O$_2$CNHCH$_2$CH$_2$HNCH$_2$CH$_2$NH$_3$)$_2$].xsol (9)

0.081 g (0.25 mmol) H$_5$hpdta was dissolved in 5 ml of deionised water by addition of diethylenetriamine. 0.202 g (0.5 mmol) Fe(NO$_3$)$_3$.9H$_2$O was added to the reaction mixture followed by diethylenetriamine to adjust the pH to 8.5.

Example 10 w[Fe(μ-O)(μ-OH)(hpdta)$_2$(O$_2$CNHCH$_2$CH$_2$OH)$_2$]. xsol (10)

0.081 g (0.25 mmol) H$_5$hpdta was dissolved in 5 ml of deionised water by addition of ethanolamine. 0.202 g (0.5 mmol) Fe(NO$_3$)$_3$.9H$_2$O was added to the reaction mixture followed by ethanolamine to adjust the pH to 8.5.

Example 11 w[Fe$_4$(μ-O)(μ-OH)(hpdta)$_2$(O$_2$CNHCH$_2$CH$_2$NH$_3$)$_2$]. xsol (11)

0.081 g (0.25 mmol) H$_5$hpdta was dissolved in 5 ml of deionised water by addition of ethanolamine. 0.202 g (0.5 mmol) Fe(NO$_3$)$_3$.9H$_2$O was added to the reaction mixture followed by ethylenediamine to adjust the pH to 8.5. The compound II crystallises after addition of DMA within 10 days.

Al Analogues:

Example 11 w[Al$^{III}_4$(μ-O)(μ-OH)(hpdta)$_2$(CO$_3$)$_2$].sol (12)

0.081 g (0.25 mmol) H$_5$hpdta was dissolved in 50 ml of deionised water by addition of 0.5 ml sodium hydroxide solution (2M). 0.187 g (0.5 mmol) Al(NO$_3$)$_3$.9H$_2$O was added to the reaction mixture followed by 0.25 ml sodium hydroxide solution (0.1 M) to adjust the pH to 8.5.

Example 12 w[Al$_4$(μ-O)(μ-OH)(hpdta)$_2$(O$_2$CNHC$_2$H$_4$NH$_3$)$_2$].x sol (13)

0.081 g (0.25 mmol) H$_5$hpdta was dissolved in 50 ml of deionised water by addition of ethylenediamine. 0.187 g (0.5 mmol) Al(NO$_3$)$_3$.9H$_2$O was added to the reaction mixture followed by 0.25 ml ethylenediamine to adjust the pH to 8.5.

Example 13 w[Al$_4$(μ-O)(μ-OH)(hpdta)$_2$(O$_2$CNHNH$_3$)$_2$].x sol (14)

0.081 g (0.25 mmol) H$_5$hpdta was dissolved in 50 ml of deionised water by addition of hydrazine. 0.187 g (0.5 mmol) Al(NO$_3$)$_3$.9H$_2$O was added to the reaction mixture followed by 0.25 ml hydrazine to adjust the pH to 8.5

Example 14 w[Al$_4$(μ-O)(μ-OH)(hpdta)$_2$(O$_2$CNHC$_4$H$_8$NH$_3$)$_2$].x sol (15)

0.081 g (0.25 mmol) H$_5$hpdta was dissolved in 50 ml of deionised water by addition of 1,4-diaminobutane. 0.187 g (0.5 mmol) Al(NO$_3$)$_3$.9H$_2$O was added to the reaction mixture followed by 0.25 ml 4-diaminobutane to adjust the pH to 8.5.

Example 15 w[Al$_4$(μ-O)(μ-OH)(hpdta)$_2$(O$_2$CNHC$_6$H$_{12}$NH$_3$)$_2$].x sol (16)

0.081 g (0.25 mmol) H$_5$hpdta was dissolved in 50 ml of deionised water by addition of hexamethylenediamine. 0.187 g (0.5 mmol) Al(NO$_3$)$_3$.9H$_2$O was added to the reaction mixture followed by 0.25 ml hexamethylenediamine to adjust the pH to 8.5.

Example 16 w[Al$_4$(μ-O)(μ-OH)(hpdta)$_2$(O$_2$CNHC$_7$H$_{14}$NH$_3$)$_2$].x sol (17)

0.081 g (0.25 mmol) H$_5$hpdta was dissolved in 50 ml of deionised water by addition of heptamethylenediamine. 0.187 g (0.5 mmol) Al(NO$_3$)$_3$.9H$_2$O was added to the reaction mixture followed by 0.25 ml heptamethylenediamine to adjust the pH to 8.5.

Example 17 w[Al$_4$(μ-O)(μ-OH)(hpdta)$_2$(O$_2$CNHC$_2$H$_4$NC$_4$H$_8$NH$_2$)$_2$].xsol (18)

0.081 g (0.25 mmol) H$_5$hpdta was dissolved in 50 ml of deionised water by addition of 1-(2-aminoethyl)piperazine. 0.187 g (0.5 mmol) Al(NO$_3$)$_3$.9H$_2$O was added to the reaction mixture followed 1-(2-aminoethyl)piperazine to adjust the pH to 8.5.

Example 18 w[Al$_4$(μ-O)(μ-OH)(hpdta)$_2$(O$_2$CNHC$_3$H$_7$)$_2$].xsol (19)

0.081 g (0.25 mmol) H$_5$hpdta was dissolved in 50 ml of deionised water by addition of propylamine. 0.187 g (0.5 mmol) Al(NO$_3$)$_3$.9H$_2$O was added to the reaction mixture followed by propylamine to adjust the pH to 8.5.

Example 19 w[Al$_4$(μ-O)(μ-OH)(hpdta)$_2$(O$_2$CNHCH$_2$CH$_2$HNCH$_2$CH$_2$NH$_3$)$_2$].xsol (20)

0.081 g (0.25 mmol) H$_5$hpdta was dissolved in 50 ml of deionised water by addition of diethylenetriamine. 0.187 g (0.5 mmol) Al(NO$_3$)$_3$.9H$_2$O was added to the reaction mixture followed by diethylenetriamine to adjust the pH to 8.5.

Example 20 w[Al$_4$(μ-O)(μ-OH)(hpdta)$_2$(O$_2$CNHCH$_2$CH$_2$OH)$_2$].xsol (21)

0.081 g (0.25 mmol) H$_5$hpdta was dissolved in 50 ml of deionised water by addition of ethanolamine. 0.187 g (0.5 mmol) Al(NO$_3$)$_3$.9H$_2$O was added to the reaction mixture followed by ethanolamine to adjust the pH to 8.5.

Cu Analogues:

Example 21 w[Cu$^{III}_4$(μ-O)(μ-OH)(hpdta)$_2$(CO$_3$)$_2$].sol (22)

0.081 g (0.25 mmol) H$_5$hpdta was dissolved in 5 ml of deionised water by addition of 0.5 ml sodium hydroxide solution (2M). 0.085 g (0.5 mmol) CuCl$_2$.2H$_2$O was added to the reaction mixture followed by 0.25 ml sodium hydroxide solution (0.1 M) to adjust the pH to 8.5. The reaction mixture was purged with air for 30 minutes.

Example 22 w[Cu$_4$(μ-O)(μ-OH)(hpdta)$_2$(O$_2$CNHC$_2$H$_4$NH$_3$)$_2$].x sol (23)

0.081 g (0.25 mmol) H$_5$hpdta was dissolved in 5 ml of deionised water by addition of ethylenediamine. 0.085 g (0.5 mmol) CuCl$_2$.2H$_2$O was added to the reaction mixture followed by 0.25 ml ethylenediamine to adjust the pH to 8.5. The reaction mixture was purged with air for 30 minutes.

Example 23 w[Cu$_4$(μ-O)(μ-OH)(hpdta)$_2$(O$_2$CNHC$_2$H$_4$NH$_3$)$_2$].x sol (24)

0.081 g (0.25 mmol) H$_5$hpdta was dissolved in 5 ml of deionised water by addition of propylenediamine. 0.085 g (0.5 mmol) CuCl$_2$.2H$_2$O was added to the reaction mixture followed by 0.25 ml propylenediamine to adjust the pH to 8.5. The reaction mixture was purged with air for 30 minutes.

Example 24 w[Cu$_4$(μ-O)(μ-OH)(hpdta)$_2$(O$_2$CNHNH$_3$)$_2$].x sol (25)

0.081 g (0.25 mmol) H$_5$hpdta was dissolved in 5 ml of deionised water by addition of hydrazine. 0.085 g (0.5 mmol) CuCl$_2$.2H$_2$O was added to the reaction mixture followed by 0.25 ml hydrazine to adjust the pH to 8.5. The reaction mixture was purged with air for 30 minutes.

Example 25 w[Cu$_4$(μ-O)(μ-OH)(hpdta)$_2$(O$_2$CNHC$_4$H$_8$NH$_3$)$_2$].x sol (26)

0.081 g (0.25 mmol) H$_5$hpdta was dissolved in 5 ml of deionised water by addition of 1,4-diaminobutane. 0.085 g (0.5 mmol) CuCl$_2$.2H$_2$O was added to the reaction mixture followed by 0.25 ml 4-diaminobutane to adjust the pH to 8.5. The reaction mixture was purged with air for 30 minutes.

Example 26 w[Cu$_4$(μ-O)(μ-OH)(hpdta)$_2$(O$_2$CNHC$_6$H$_{12}$NH$_3$)$_2$].x sol (27)

0.081 g (0.25 mmol) H$_5$hpdta was dissolved in 5 ml of deionised water by addition of hexamethylenediamine. 0.085 g (0.5 mmol) CuCl$_2$.2H$_2$O was added to the reaction mixture followed by 0.25 ml hexamethylenediamine to adjust the pH to 8.5. The reaction mixture was purged with air for 30 minutes.

Example 27 w[Cu$_4$(μ-O)(μ-OH)(hpdta)$_2$(O$_2$CNHC$_7$H$_{14}$NH$_3$)$_2$].x sol (28)

0.081 g (0.25 mmol) H$_5$hpdta was dissolved in 5 ml of deionised water by addition of heptamethylenediamine 0.085 g (0.5 mmol) CuCl$_2$.2H$_2$O was added to the reaction mixture followed by 0.25 ml heptamethylenediamine to adjust the pH to 8.5. The reaction mixture was purged with air for 30 minutes.

Example 28 w[Cu$_4$(μ-O)(μ-OH)(hpdta)$_2$(O$_2$CNHC$_2$H$_4$NC$_4$H$_8$NH$_2$)$_2$].xsol (29)

0.081 g (0.25 mmol) H$_5$hpdta was dissolved in 5 ml of deionised water by addition of 1-(2-aminoethyl)piperazine. 0.085 g (0.5 mmol) CuCl$_2$.2H$_2$O was added to the reaction mixture followed 1-(2-aminoethyl)piperazine to adjust the pH to 8.5. The reaction mixture was purged with air for 30 minutes.

Example 29 w[Cu$_4$(μ-O)(μ-OH)(hpdta)$_2$(O$_2$CNHC$_3$H$_7$)$_2$].xsol (30)

0.081 g (0.25 mmol) H$_5$hpdta was dissolved in 5 ml of deionised water by addition of propylamine. 0.085 g (0.5 mmol) CuCl$_2$.2H$_2$O was added to the reaction mixture followed by propylamine to adjust the pH to 8.5. The reaction mixture was purged with air for 30 minutes.

Example 30 w[Cu$_4$(μ-O)(μ-OH)(hpdta)$_2$(O$_2$CNHCH$_2$CH$_2$HNCH$_2$CH$_2$NH$_3$)$_2$].xsol (31)

0.081 g (0.25 mmol) H$_5$hpdta was dissolved in 5 ml of deionised water by addition of diethylenetriamine. 0.085 g (0.5 mmol) CuCl$_2$.2H$_2$O was added to the reaction mixture followed by diethylenetriamine to adjust the pH to 8.5. The reaction mixture was purged with air for 30 minutes.

Example 31 w[Cu$_4$(μ-O)(μ-OH)(hpdta)$_2$(O$_2$CNHCH$_2$CH$_2$OH)$_2$].xsol (32)

0.081 g (0.25 mmol) H$_5$hpdta was dissolved in 5 ml of deionised water by addition of ethanolamine. 0.085 g (0.5 mmol) CuCl$_2$.2H$_2$O was added to the reaction mixture followed by ethanolamine to adjust the pH to 8.5. The reaction mixture was purged with air for 30 minutes.

Ga Analogues:

Example 32 w[Ga$^{III}_4$(μ-O)(μ-OH)(hpdta)$_2$(CO$_3$)$_2$].sol (33)

0.0818 g (0.25 mmol) H$_5$hpdta was dissolved in 5 ml of deionised water by addition of 0.5 ml sodium hydroxide solution (2M). 0.128 g (0.5 mmol) Ga(NO$_3$)$_3$.H$_2$O was added to the reaction mixture followed by 0.25 ml sodium hydroxide solution (0.1 M) to adjust the pH to 8.5.

Example 33 w[Ga$_4$(μ-O)(μ-OH)(hpdta)$_2$(O$_2$CNHC$_2$H$_4$NH$_3$)$_2$].x sol (34)

0.081 g (0.25 mmol) H$_5$hpdta was dissolved in 5 ml of deionised water by addition of ethylenediamine. 0.128 g (0.5 mmol) Ga(NO$_3$)$_3$.H$_2$O was added to the reaction mixture followed by 0.25 ml ethylenediamine to adjust the pH to 8.5.

Example 34 w[Ga$_4$(μ-O)(μ-OH)(hpdta)$_2$(O$_2$CNHC$_2$H$_4$NH$_3$)$_2$].x sol (35)

0.081 g (0.25 mmol) H$_5$hpdta was dissolved in 5 ml of deionised water by addition of propylenediamine. 0.128 g (0.5 mmol) Ga(NO$_3$)$_3$.H$_2$O was added to the reaction mixture followed by 0.25 ml propylenediamine to adjust the pH to 8.5.

Example 35 w[Ga$_4$(μ-O)(μ-OH)(hpdta)$_2$(O$_2$CNHNH$_3$)$_2$].x sol (36)

0.081 g (0.25 mmol) H$_5$hpdta was dissolved in 5 ml of deionised water by addition of hydrazine. 0.128 g (0.5 mmol) Ga(NO$_3$)$_3$.H$_2$O was added to the reaction mixture followed by 0.25 ml hydrazine to adjust the pH to 8.5

Example 36 w[Ga$_4$(μ-O)(μ-OH)(hpdta)$_2$(O$_2$CNHC$_4$H$_8$NH$_3$)$_2$].x sol (37)

0.081 g (0.25 mmol) H$_5$hpdta was dissolved in 5 ml of deionised water by addition of 1,4-diaminobutane. 0.128 g (0.5 mmol) Ga(NO$_3$)$_3$.H$_2$O was added to the reaction mixture followed by 0.25 ml 4-diaminobutane to adjust the pH to 8.5.

Example 37 w[Ga$_4$(μ-O)(μ-OH)(hpdta)$_2$(O$_2$CNHC$_6$H$_{12}$NH$_3$)$_2$].x sol (38)

0.081 g (0.25 mmol) H$_5$hpdta was dissolved in 5 ml of deionised water by addition of hexamethylenediamine. 0.128 g (0.5 mmol) Ga(NO$_3$)$_3$.H$_2$O was added to the reaction mixture followed by 0.25 ml hexamethylenediamine to adjust the pH to 8.5.

Example 38 w[Ga$_4$(μ-O)(μ-OH)(hpdta)$_2$(O$_2$CNHC$_7$H$_{14}$NH$_3$)$_2$].x sol (39)

0.081 g (0.25 mmol) H$_5$hpdta was dissolved in 5 ml of deionised water by addition of heptamethylenediamine. 0.128 g (0.5 mmol) Ga(NO$_3$)$_3$.H$_2$O was added to the reaction mixture followed by 0.25 ml heptamethylenediamine to adjust the pH to 8.5.

Example 39 w[Ga$_4$(μ-O)(μ-OH)(hpdta)$_2$(O$_2$CNHC$_2$H$_4$NC$_4$H$_8$NH$_2$)$_2$].xsol (40)

0.081 g (0.25 mmol) H$_5$hpdta was dissolved in 5 ml of deionised water by addition of 1-(2-aminoethyl)piperazine. 0.128 g (0.5 mmol) Ga(NO$_3$)$_3$.H$_2$O was added to the reaction mixture followed 1-(2-aminoethyl)piperazine to adjust the pH to 8.5.

Example 40 w[Ga$_4$(μ-O)(μ-OH)(hpdta)$_2$(O$_2$CNHC$_3$H$_7$)$_2$].xsol (41)

0.081 g (0.25 mmol) H$_5$hpdta was dissolved in 5 ml of deionised water by addition of propylamine. 0.128 g (0.5 mmol) Ga(NO$_3$)$_3$.H$_2$O was added to the reaction mixture followed by propylamine to adjust the pH to 8.5.

Example 41 w[Ga$_4$(μ-O)(μ-OH)(hpdta)$_2$(O$_2$CNHCH$_2$CH$_2$HNCH$_2$CH$_2$NH$_3$)$_2$].xsol (42)

0.081 g (0.25 mmol) H$_5$hpdta was dissolved in 5 ml of deionised water by addition of diethylenetriamine. 0.128 g (0.5 mmol) Ga(NO$_3$)$_3$.H$_2$O was added to the reaction mixture followed by diethylenetriamine to adjust the pH to 8.5.

Example 42 w[Ga$_4$(μ-O)(μ-OH)(hpdta)$_2$(O$_2$CNHCH$_2$CH$_2$OH)$_2$].xsol (43)

0.0818 g (0.25 mmol) H$_5$hpdta was dissolved in 5 ml of deionised water by addition of ethanolamine. 0.128 g (0.5 mmol) Ga(NO$_3$)$_3$.H$_2$O was added to the reaction mixture followed by ethanolamine to adjust the pH to 8.5.

Mn Analogues:

Example 43 w[Mn$_4$(μ-O)(μ-OH)(hpdta)$_2$(CO$_3$)$_2$].sol (44)

0.081 g (0.25 mmol) H$_5$hpdta was dissolved in 5 ml of deionised water by addition of 0.5 ml sodium hydroxide solution (2M). 0.199 g (0.5 mmol) MnCl$_2$.4H$_2$O was added to the reaction mixture followed by 0.25 ml sodium hydroxide solution (0.1M) to adjust the pH to 8.5. The reaction mixture was purged with air for 30 minutes.

Example 44 w[Mn$_4$(μ-O)(μ-OH)(hpdta)$_2$(O$_2$CNHC$_2$H$_4$NH$_3$)$_2$].x sol (45)

0.081 g (0.25 mmol) H$_5$hpdta was dissolved in 5 ml of deionised water by addition of ethylenediamine. 0.199 g (0.5 mmol) MnCl$_2$.4H$_2$O was added to the reaction mixture followed by 0.25 ml ethylenediamine to adjust the pH to 8.5. The reaction mixture was purged with air for 30 minutes.

Example 45 w[Mn$_4$(μ-O)(μ-OH)(hpdta)$_2$(O$_2$CNHC$_2$H$_4$NH$_3$)$_2$].x sol (46)

0.081 g (0.25 mmol) H$_5$hpdta was dissolved in 5 ml of deionised water by addition of propylenediamine. 0.128 g (0.5 mmol) Ga(NO$_3$)$_3$.H$_2$O was added to the reaction mixture followed by 0.25 ml propylenediamine to adjust the pH to 8.5. The reaction mixture was purged with air for 30 minutes.

Example 46 w[Mn$_4$(μ-O)(μ-OH)(hpdta)$_2$(O$_2$CNHNH$_3$)$_2$].x sol (47)

0.081 g (0.25 mmol) H$_5$hpdta was dissolved in 5 ml of deionised water by addition of hydrazine. 0.199 g (0.5 mmol) MnCl$_2$.4H$_2$O was added to the reaction mixture followed by 0.25 ml hydrazine to adjust the pH to 8.5. The reaction mixture was purged with air for 30 minutes.

Example 47 w[Mn$_4$(μ-O)(μ-OH)(hpdta)$_2$(O$_2$CNHC$_4$H$_8$NH$_3$)$_2$].x sol (48)

0.081 g (0.25 mmol) H$_5$hpdta was dissolved in 5 ml of deionised water by addition of 1,4-diaminobutane. 0.199 g (0.5 mmol) MnCl$_2$.4H$_2$O was added to the reaction mixture followed by 0.25 ml 4-diaminobutane to adjust the pH to 8.5. The reaction mixture was purged with air for 30 minutes.

Example 48 w[Mn$_4$(μ-O)(μ-OH)(hpdta)$_2$(O$_2$CNHC$_6$H$_{12}$NH$_3$)$_2$].x sol (49)

0.081 g (0.25 mmol) H$_5$hpdta was dissolved in 5 ml of deionised water by addition of hexamethylenediamine. 0.199 g (0.5 mmol) MnCl$_2$.4H$_2$O was added to the reaction mixture followed by 0.25 ml hexamethylenediamine to adjust the pH to 8.5. The reaction mixture was purged with air for 30 minutes.

Example 49 w[Mn$_4$(μ-O)(μ-OH)(hpdta)$_2$(O$_2$CNHC$_7$H$_{14}$NH$_3$)$_2$].x sol (50)

0.081 g (0.25 mmol) H$_5$hpdta was dissolved in 5 ml of deionised water by addition of heptamethylenediamine.

0.199 g (0.5 mmol) $MnCl_2.4H_2O$ was added to the reaction mixture followed by 0.25 ml heptamethylenediamine to adjust the pH to 8.5. The reaction mixture was purged with air for 30 minutes.

Example 50 w[$Mn_4$(μ-O)(μ-OH)(hpdta)$_2$($O_2CNHC_2H_4NC_4H_8NH_2$)$_2$].xsol (51)

0.081 g (0.25 mmol) $H_5$hpdta was dissolved in 5 ml of deionised water by addition of 1-(2-aminoethyl)piperazine. 0.199 g (0.5 mmol) $MnCl_2.4H_2O$ was added to the reaction mixture followed 1-(2-aminoethyl)piperazine to adjust the pH to 8.5. The reaction mixture was purged with air for 30 minutes.

Example 51 w[$Mn_4$(μ-O)(μ-OH)(hpdta)$_2$($O_2CNHC_3H_7$)$_2$].xsol (52)

0.0818 g (0.25 mmol) $H_5$hpdta was dissolved in 5 ml of deionised water by addition of propylamine. 0.199 g (0.5 mmol) $MnCl_2.4H_2O$ was added to the reaction mixture followed by propylamine to adjust the pH to 8.5. The reaction mixture was purged with air for 30 minutes.

Example 52 w[$Mn_4$(μ-O)(μ-OH)(hpdta)$_2$($O_2CNHCH_2CH_2HNCH_2CH_2NH_3$)$_2$].xsol (53)

0.081 g (0.25 mmol) $H_5$hpdta was dissolved in 5 ml of deionised water by addition of diethylenetriamine. 0.199 g (0.5 mmol) $MnCl_2.4H_2O$ was added to the reaction mixture followed by diethylenetriamine to adjust the pH to 8.5. The reaction mixture was purged with air for 30 minutes.

Example 53 w[$Mn_4$(μ-O)(μ-OH)(hpdta)$_2$($O_2CNHCH_2CH_2OH$)$_2$].xsol (54)

0.081 g (0.25 mmol) $H_5$hpdta was dissolved in 5 ml of deionised water by addition of ethanolamine. 0.199 g (0.5 mmol) $MnCl_2.4H_2O$ was added to the reaction mixture followed by ethanolamine to adjust the pH to 8.5. The reaction mixture was purged with air for 30 minutes.

Cr Compounds:

Example 54 w[$Cr_4$(μ-O)(μ-OH)(hpdta)$_2$($CO_3$)$_2$].sol (55)

0.081 g (0.25 mmol) $H_5$hpdta was dissolved in 5 ml of deionised water by addition of 0.5 ml sodium hydroxide solution (2M). 0.133 g (0.5 mmol) $CrCl_3.6H_2O$ was added to the reaction mixture followed by 0.25 ml sodium hydroxide solution (0.1 M) to adjust the pH to 8.5. The reaction mixture was refluxed at 100° C. for 24 hours and left to cool.

Example 55 w[$Cr_4$(μ-O)(μ-OH)(hpdta)$_2$($O_2CNHC_2H_4NH_3$)$_2$].x sol (56)

0.081 g (0.25 mmol) $H_5$hpdta was dissolved in 5 ml of deionised water by addition of ethylenediamine. 0.133 g (0.5 mmol) $CrCl_3.6H_2O$ was added to the reaction mixture followed by 0.25 ml ethylenediamine to adjust the pH to 8.5. The reaction mixture was refluxed at 100° C. for 24 hours and left to cool.

Example 56 w[$Cr_4$(μ-O)(μ-OH)(hpdta)$_2$($O_2CNHC_2H_4NH_3$)$_2$].x sol (57)

0.081 g (0.25 mmol) $H_5$hpdta was dissolved in 5 ml of deionised water by addition of propylenediamine. 0.133 g (0.5 mmol) $CrCl_3.6H_2O$ was added to the reaction mixture followed by 0.25 ml propylenediamine to adjust the pH to 8.5. The reaction mixture was refluxed at 100° C. for 24 hours and left to cool.

Example 57 w[$Cr_4$(μ-O)(μ-OH)(hpdta)$_2$($O_2CNHNH_3$)$_2$].x sol (58)

0.081 g (0.25 mmol) $H_5$hpdta was dissolved in 5 ml of deionised water by addition of hydrazine. 0.133 g (0.5 mmol) $CrCl_3.6H_2O$ was added to the reaction mixture followed by 0.25 ml hydrazine to adjust the pH to 8.5. The reaction mixture was refluxed at 100° C. for 24 hours and left to cool.

Example 58 w[$Cr_4$(μ-O)(μ-OH)(hpdta)$_2$($O_2CNHC_4H_8NH_3$)$_2$].x sol (59)

0.081 g (0.25 mmol) $H_5$hpdta was dissolved in 5 ml of deionised water by addition of 1,4-diaminobutane. 0.133 g (0.5 mmol) $CrCl_3.6H_2O$ was added to the reaction mixture followed by 0.25 ml 4-diaminobutane to adjust the pH to 8.5. The reaction mixture was refluxed at 100° C. for 24 hours and left to cool.

Example 59 w[$Cr_4$(μ-O)(μ-OH)(hpdta)$_2$($O_2CNHC_6H_{12}NH_3$)$_2$].x sol (60)

0.081 g (0.25 mmol) $H_5$hpdta was dissolved in 5 ml of deionised water by addition of hexamethylenediamine. 0.133 g (0.5 mmol) $CrCl_3.6H_2O$ was added to the reaction mixture followed by 0.25 ml hexamethylenediamine to adjust the pH to 8.5. The reaction mixture was refluxed at 100° C. for 24 hours and left to cool.

Example 60 w[$Cr_4$(μ-O)(μ-OH)(hpdta)$_2$($O_2CNHC_7H_{14}NH_3$)$_2$].x sol (61)

0.081 g (0.25 mmol) $H_5$hpdta was dissolved in 5 ml of deionised water by addition of heptamethylenediamine. 0.133 g (0.5 mmol) $CrCl_3.6H_2O$ was added to the reaction mixture followed by 0.25 ml heptamethylenediamine to adjust the pH to 8.5. The reaction mixture was refluxed at 100° C. for 24 hours and left to cool.

Example 61

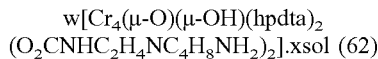
w[Cr$_4$(μ-O)(μ-OH)(hpdta)$_2$
(O$_2$CNHC$_2$H$_4$NC$_4$H$_8$NH$_2$)$_2$].xsol (62)

0.081 g (0.25 mmol) H$_5$hpdta was dissolved in 5 ml of deionised water by addition of 1-(2-aminoethyl)piperazine. 0.133 g (0.5 mmol) CrCl$_3$.6H$_2$O was added to the reaction mixture followed 1-(2-aminoethyl)piperazine to adjust the pH to 8.5. The reaction mixture was refluxed at 100° C. for 24 hours and left to cool.

Example 62

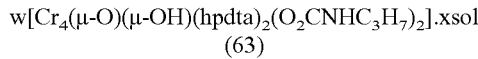
w[Cr$_4$(μ-O)(μ-OH)(hpdta)$_2$(O$_2$CNHC$_3$H$_7$)$_2$].xsol (63)

0.081 g (0.25 mmol) H$_5$hpdta was dissolved in 5 ml of deionised water by addition of propylamine. 0.133 g (0.5 mmol) CrCl$_3$.6H$_2$O was added to the reaction mixture followed by propylamine to adjust the pH to 8.5. The reaction mixture was refluxed at 100° C. for 24 hours and left to cool.

Example 63

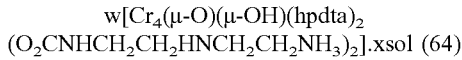
w[Cr$_4$(μ-O)(μ-OH)(hpdta)$_2$
(O$_2$CNHCH$_2$CH$_2$HNCH$_2$CH$_2$NH$_3$)$_2$].xsol (64)

0.081 g (0.25 mmol) H$_5$hpdta was dissolved in 5 ml of deionised water by addition of diethylenetriamine. 0.133 g (0.5 mmol) CrCl$_3$.6H$_2$O was added to the reaction mixture followed by diethylenetriamine to adjust the pH to 8.5. The reaction mixture was refluxed at 100° C. for 24 hours and left to cool.
Co Analogue:

Example 64

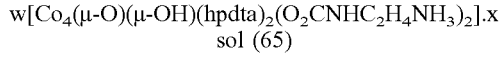
w[Co$_4$(μ-O)(μ-OH)(hpdta)$_2$(O$_2$CNHC$_2$H$_4$NH$_3$)$_2$].xsol (65)

0.081 g (0.25 mmol) H$_5$hpdta was dissolved in 5 ml of deionised water by addition of ethylenediamine. 0.119 g (0.5 mmol) CoCl$_3$.6H$_2$O was added to the reaction mixture followed by 0.25 ml ethylenediamine to adjust the pH to 8.5. The reaction mixture was purged with air for 30 minutes, refluxed at 100° C. for 24 hours and left to cool.

The compounds of entities 1 to 65 also form at different ligand:metal molar ratios.

The compounds of entities 1 to 65 also form in the absence of DMA. (DMA is used as a cosolvent to facilitate the formation of suitably sized single crystals for single crystal x-ray analyses of the compounds. Single crystals are only required for solid state characterisation purposes.)

The compounds of entities 1 to 65 also form in the pH range 7-14.

The compounds of entities 1 to 64 can also be formed by dissolving their corresponding compound 1 analogues (i.e. an analogue of compound 1 which has same core metal ion configuration as the above mentioned compounds) in deionised water and using the above mentioned bases to adjust the pH to any pH unit between pH 7 and 14.

The compounds of entities 1 to 64 also form in other polar solvents

The amount of deionised water does not affect the formation of the compounds of entities 1 to 64.

The compounds are generated in situ using the above-described synthetic procedures. Therefore, the compounds reaction mixtures can also be used to capture and release $CO_2$.

The carbamate and carbonate ligands that are the result of the $CO_2$ capture may be protonated, neutral (e.g. zwitterionic form) or negatively charged.

All of these compounds may be used for capture and release of $CO_2$.

All of these compounds may also be immobilised, for example on a support such as a membrane or a silicate powder.

Materials and Methods:
  *Headspace gas sampled using an Agilent 5 µl gas tight syringe.
  GC mass spectra recorded by injecting the headspace sample into a GC-MS (Gas Chromatography-Mass Spectrometry), LCT Premier.
Operating Settings:
  Carrier gas=Helium flow rate=60 Lh$^{-1}$
  Column Diameters=30 m×0.250 mm×0.25 µm
  Split injection (2:1)
  Injection port temperature=200° C.
  Desolvatation gas rate=500 Lh$^{-1}$.
  Isothermal temperature=26° C.,
  Retention window value=0-60 minutes,
  m/z range=28-600,
  Scan time=0.9 sec and inter-scan delay=0.1 sec.
  $O_2$ signal was monitored at 31.99 m/z and the $CO_2$ signal at 43.99 m/z; the observed relative intensities were compared to the relative intensities of a conventional air sample (see picture 3).

Experiment 1
The acid-induced release of $CO_2$ can be demonstrated by taking 50 mg of the $CO_2$ trapping compound B and dissolving it in a GC-MS vial containing 1 ml of any aqueous acid solution at any pH value between 6 and 2, and sealed with a septum. The $CO_2$ release can be detected by removing a sample of gas from the headspace of the GC-MS vial and analysing it using gas chromatography mass spectrometry (GC-MS). The recorded spectrum shows a dramatic increase in concentration of $CO_2$* (see FIG. 1).

FIG. 1:=Gas chromatography Mass spectra (GC-MS) recorded for headspace of GC-MS vial containing 50 mg of (enH)[Fe$_4$(μ-O)(μ-OH)(hpdta)$_2$(O$_2$CNHC$_4$H$_8$NH$_3$)$_2$] .6.5H$_2$O dissolved in 1 ml of:
  A=1.5×10$^{-4}$ M aqueous ethylenediamine solution (pH=9.4)
  B=deionised water (pH=7)
  C=4.7×10$^{-4}$ M aqueous sulfuric acid (pH=5.44)
  D=3.98×10$^{-4}$ M aqueous sulfuric acid (pH=4)
  E=2.6×10$^{-4}$ M aqueous sulfuric acid (pH=2.2)

A and B show GC-MS spectra recorded for an analogue of compound B that has been dissolved in an aqueous alkaline solution at pH 8.5 and in deionised water respectively. The relative intensities of the $CO_2$ peak (43.99 m/z) and the $O_2$ peak (31.99 m/z) are similar to those observed in the standard sample of air (seen in FIG. 3c). This demonstrates that $CO_2$ is not released from the compounds under these conditions.

The spectra in C-E are GC-MS spectra recorded when compound B is dissolved in a series of aqueous acid solutions with pH values approaching pH 2. The intensities of the $CO_2$ (43.99 m/z) peaks increase, and the relative intensities of $CO_2$ peak (43.99 m/z) and the $O_2$ peak (31.99 m/z) change upon higher acid concentration. These observations demonstrate that the release of $CO_2$ from compound B is an acid induced process.

An example of a $CO_2$ trapping compound which can be used to demonstrate the release of $CO_2$ is (enH)[$Fe_4$(μ-O)(μ-OH)(hpdta)$_2$($O_2CNHC_4H_8NH_3$)$_2$].6.5$H_2O$. Example of an acidic aqueous solution is a $8×10^{-4}$ M aqueous sulphuric acid (pH=4).

Experiment 2

The compounds' ability to reversibly release and capture $CO_2$ can be demonstrated by taking 50 mg of the $CO_2$ trapping compound B and dissolving it in a GC-MS vial containing 1 ml of an aqueous basic solution with any pH value in the range pH 10 to pH 8.5 in a GC-MS vial sealed with a septum. Addition of an acid through the septum to reduce the pH of the system to any pH value between pH 6 and pH 2 will result in the release of $CO_2$. The $CO_2$ release can be detected by taking a sample of gas from the headspace of the GC-MS vial and analysing it using gas chromatography mass spectrometry (GC-MS). The recorded spectrum shows a dramatic increase in concentration of $CO_2$.*

The addition of an aqueous base through the septum to readjust the pH of the system to any value between pH 8.5 and pH 10 will result in the reabsorption of $CO_2$. This can be detected by taking a sample of gas from the headspace of the GC-MS vial and analysing it using gas chromatography mass spectrometry (GC-MS). The recorded spectrum shows a dramatic decrease in the $CO_2$ concentration and the relative intensities of $CO_2$ and $O_2$ return to background levels* (see FIG. 2 and FIG. 3a).

Figure 2A:
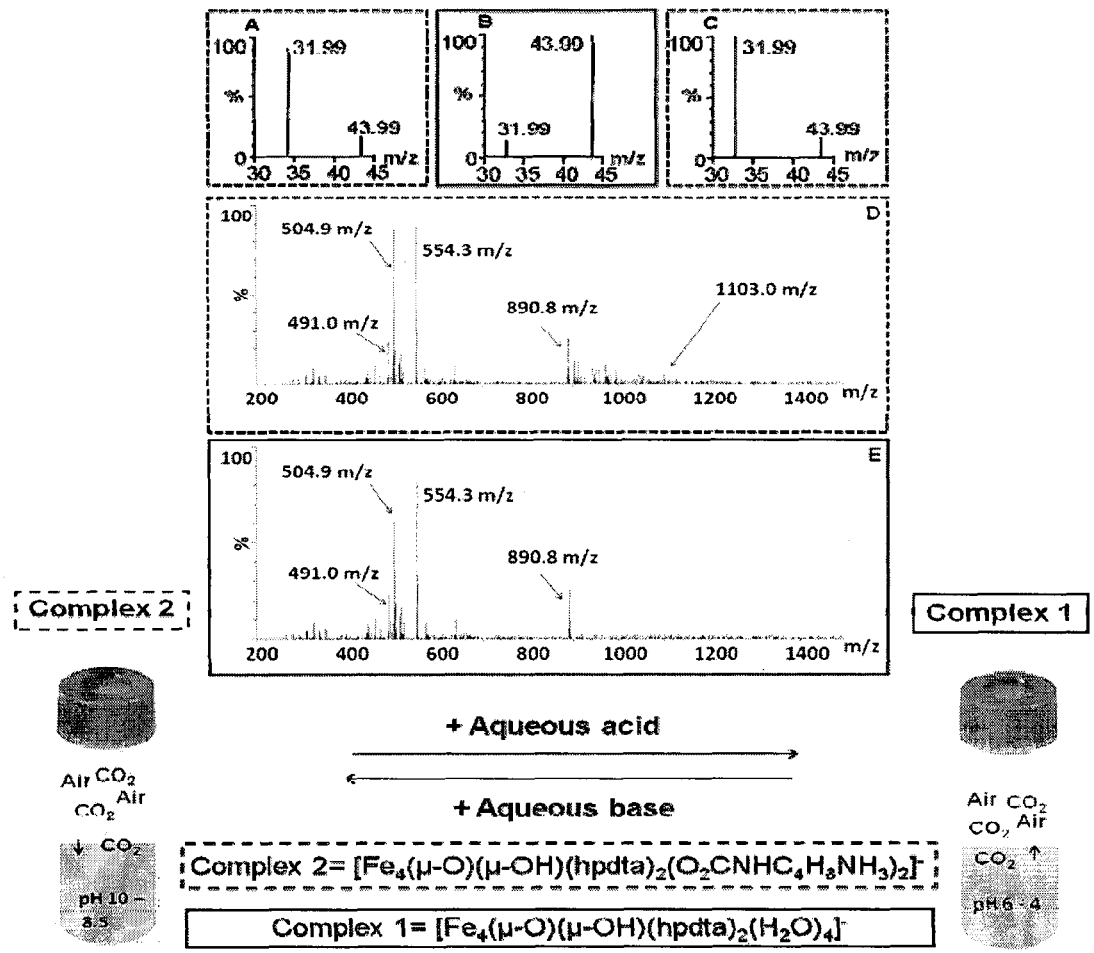
FIG. 2(a) is an overview of the acid induced $CO_2$ release and capture using (enH)[$Fe_4(\mu\text{-}O)(\mu\text{-}OH)(hpdta)_2$ $(O_2CNHC_4H_8NH_3)_2$]$\cdot 6.5H_2O$ as an example of compound B.
Figure 2B:
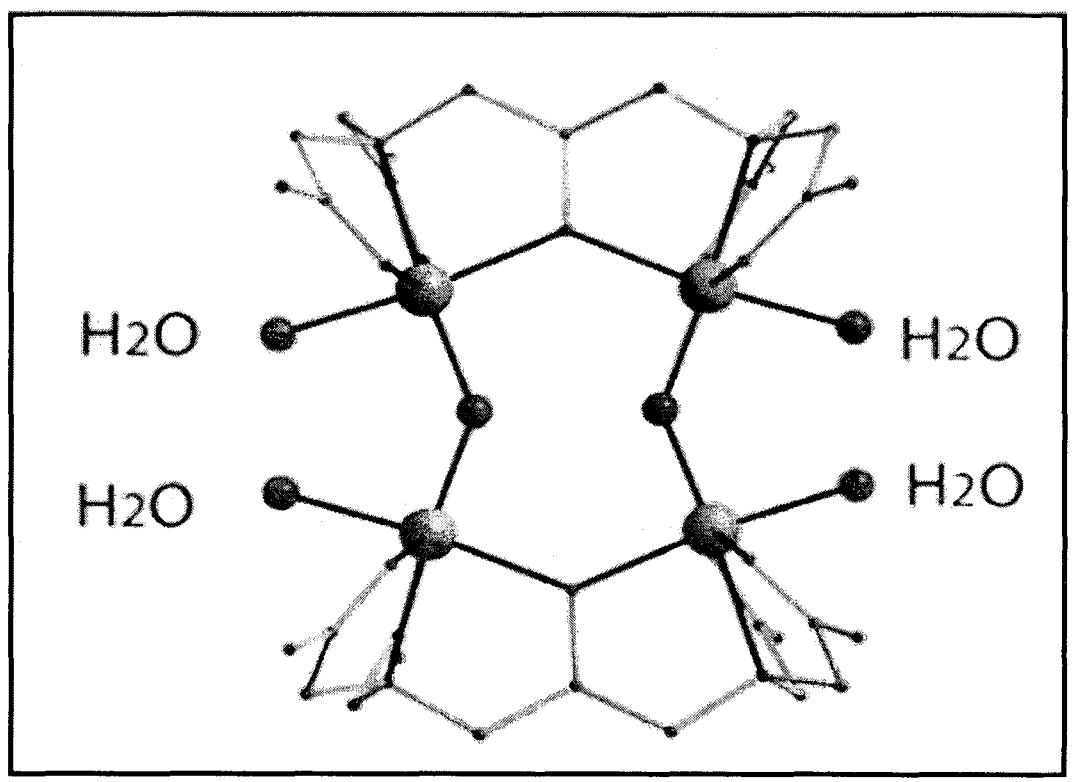
FIG. 2(b) represents the structure of complex 1 of FIG. 2(a); complex in compound A.
Figure 2C:
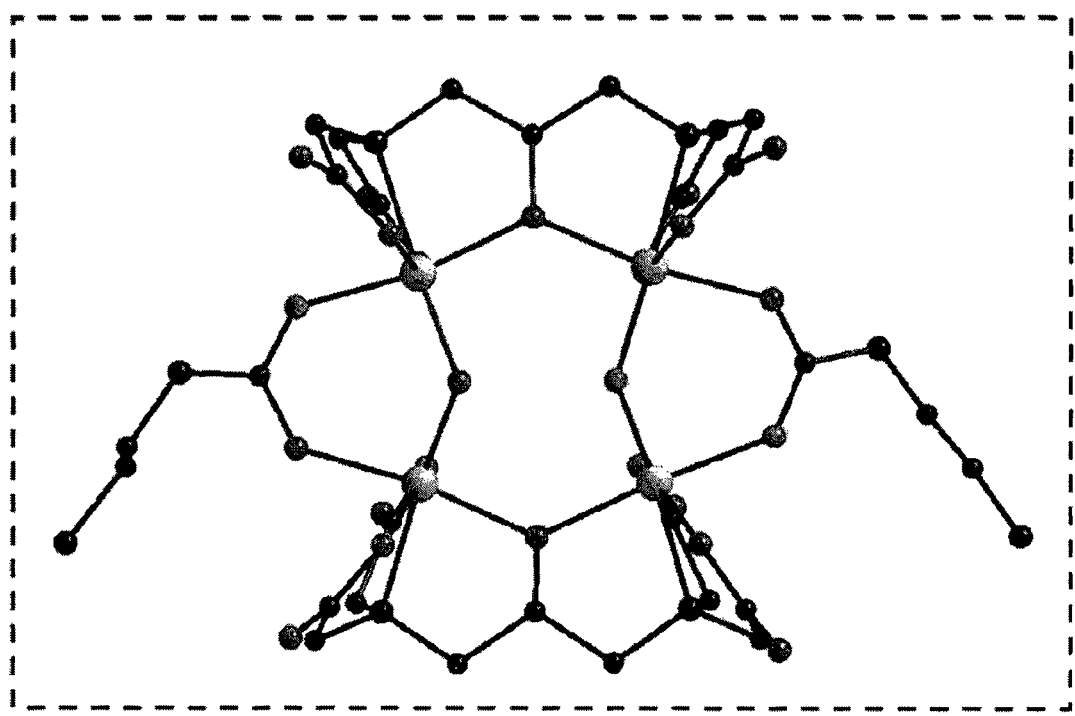
FIG. 2(c) represents the structure of complex 2 of FIG. 2(a); complex in compound B.

FIG. 2: Treating compound B, (seen in the box with hatched line), with acid causes the $CO_2$ to be released and compound A, (seen in the box with solid black line) to form. Readjusting the pH, by addition of a base, results in the uptake of $CO_2$.

In this schematic compound B=[$Fe_4$(μ-O)(μ-OH)(hpdta)$_2$($O_2CNHC_2H_4NH_3$)$_2$]$^-$ and compound A=[$Fe_4$(μ-O)(μ-OH)(hpdta)$_2$($H_2O$)$_4$]$^-$. The hydrogen atoms have been omitted from [$Fe_4$(μ-O)(μ-OH)(hpdta)$_2$($H_2O$)$_4$]$^-$ for clarity.

A, B and C=GC-MS recorded for headspace analysis following A) the dissolution of 2 in 1 ml $1.5×10^{-4}$ M aqueous ethylenediamine solution. B) the addition of 0.06 1 μl of a 33% (V/V) aqueous $H_2SO_4$ solution to adjust the pH of the system to 4. C) the subsequent addition of 0.1 μl of a 75% (V/V) aqueous ethylenediamine solution to adjust the pH of the system to pH 9.1. D and E are electrospray ionization mass spectra recorded for the solutions at pH 9.1 and 4 respectively. The isotopic envelope, seen in D, at 1103.0 m/z characterises the presence of compound 2. The isotopic envelopes at 891.0, 504.9 and 490.1 m/z characterises the presence of a tetranuclear compound. Their presence in E indicates the presence of compound A.

This figure demonstrates how, the illustrated, examples of compound A and compound B can be used to capture and release carbon dioxide through pH adjustment. It is possible to monitor this process using GC-MS headspace analyses to detect the release and subsequent recapture of $CO_2$.(A-C) and ESI-MS$^-$ to identify the species which are in solution (D-E).

When the carbon dioxide trapping compound B is dissolved in aqueous alkaline solutions of pH units between pH 8.5 and pH 10. The ESI-MS$^-$ spectrum, seen in D, shows a peak at 1103.0 m/z. This signal is characteristic of the compound B, which is stable in solution. The relative intensities of the $O_2$ peak (31.99 m/z) and the $CO_2$ peak (43.99 m/z) seen in the GC-MS spectrum in A confirms that $CO_2$ is not released from the compound at pH 8.5. When acid is added to adjust the pH of the system to between a pH value between pH 6 and pH 4, the $CO_2$ is released and compound A is formed. This is characterized by the dramatic increase in the intensity of the $CO_2$ signal (43.99 m/z) in the GC-MS spectrum seen in B. The release of $CO_2$ and the formation of compound A is further confirmed in the ESI-MS$^-$ spectrum seen in D which shows the disappearance of the characteristic peak at 1103.0 m/z, indicating that compound B is no longer present in solution.

This capture and release cycle can be repeated through successive additions of acid and base.

Figure 3:
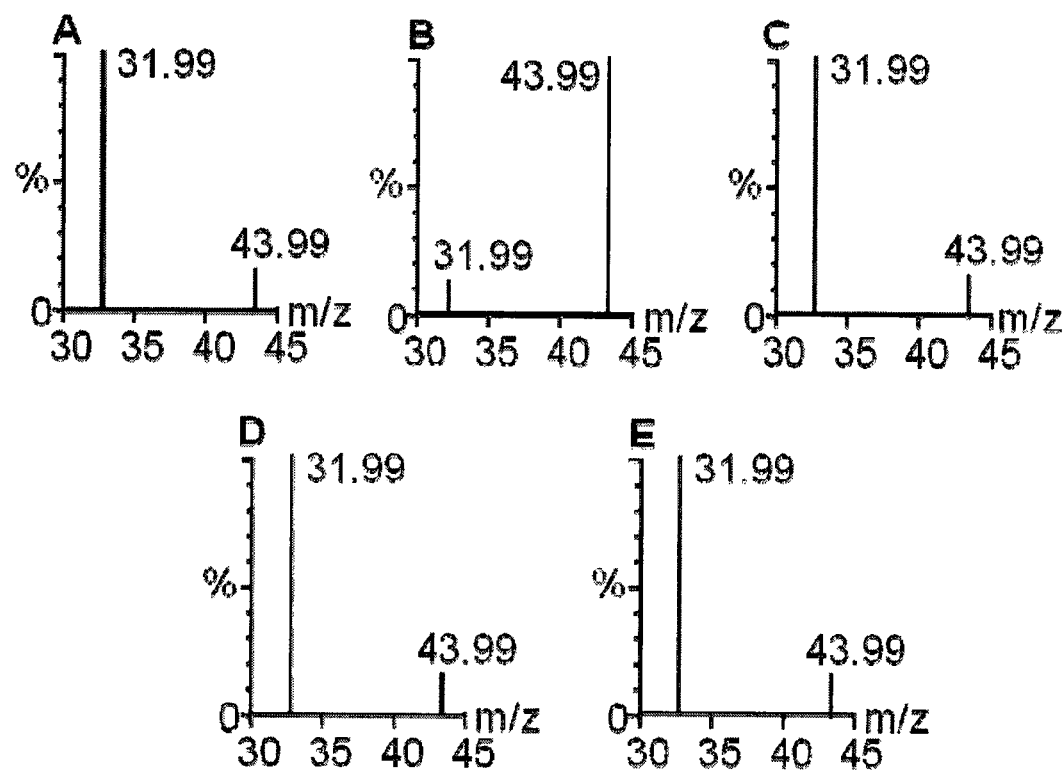
FIG. 3 is the Gas chromatography Mass spectra (GC-MS) recorded for a series of standards which clearly demonstrate the crucial role that compounds A and B play in the pH-induced reversible capture and release of $CO_2$.

FIG. 3: Gas chromatography Mass spectra (GC-MS) recorded for:
A=5 μl of a conventional air sample
B=5 μl of a sample of pure $CO_2$ standard
C=headspace of GC-MS vial following the addition of 0.06 μl of a 33% (v/v) aqueous $H_2SO_4$ solution to a system containing 1 ml $1.5×10^{-4}$ M aqueous ethylenediamine solution
D=headspace of GC-MS vial following the addition of 0.06 μl of a 33% (v/v) aqueous $H_2SO_4$ solution to a system containing 1 ml deionised water
E=headspace of GC-MS vial following the addition of 0.06 μl of a 33% (v/v) aqueous $H_2SO_4$ solution to a system containing the closely related (pipH$_2$)$_{1.5}$ [$Fe_4$(μ-O)(μ-OH)$_3$(hpdta)$_2$].6$H_2O$ compound dissolved in 1 ml $1.5×10^{-4}$ M aqueous ethylenediamine solution.

A is the GC-MS spectra of a conventional air sample this demonstrates the relative intensities of $O_2$ (31.99 m/z) and $CO_2$ (43.99 m/z) that naturally exist in air. B is a GC-MS spectra of a standard of $CO_2$ which demonstrates that the peak at 43.99 m/z can be monitored for increasing $CO_2$ and its intensity can be compared to the relative intensity of the $O_2$ peak at 31.99 m/z. This demonstrates why GC-MS to can be used to characterize the acid induced $CO_2$ release from the aforementioned systems. C and D were recorded when a representative aqueous alkaline solution at pH 8.5 and a sample of deionized water, was acidified to pH 2. This simulates the conditions of the acid induced release of $CO_2$ in the absence of compound B. E was recorded upon acidification of a system which contained a tetranuclear metal compound in place of compound 2. The compound which was used is molecularly similar to compound B except that it has a tetrahedral coordination geometry which prevents it from absorbing $CO_2$. The intensities of the $CO_2$ peaks at 43.99 m/z in these spectra do not increase and their relative intensities, compared with the $O_2$ peaks at 31.99 m/z, are similar to the relative intensities observed in a standard sample of air. This confirms that the metal, carbon dioxide trapping, compound B is required for the acid induced release of $CO_2$.

An example of a $CO_2$ trapping compounds which can be used to demonstrate the release of $CO_2$ is (enH)[$Fe_4$(μ-O)(μ-OH)(hpdta)$_2$($O_2CNHC_4H_8NH_3$)$_2$].6.5$H_2O$. Example of an aqueous basic solution is a $1.5×10^{-4}$ M aqueous ethylenediamine solution (pH=9.4). Example of an acid and the quantity required to reduce the pH of the system=0.061 μl of a 33% (v/v) aqueous $H_2SO_4$ solution which adjusts the pH of the system to 3.8. Example of an aqueous base which can be used to re-adjust the pH: 0.1 μl of a 75% (v/v) aqueous ethylenediamine solution re-adjusts the pH to 9.1.

Experiment 3

The role that the tetranuclear compounds A and B play in this process can be demonstrated by repeating experiment 2:

a) In the absence of compound B.
b) In the absence of compound B and using water in place of aqueous basic solution
c) Using a closely related compound $(pipH_2)_{1.5}[Fe_4(\mu\text{-}O)(\mu\text{-}OH)_3(hpdta)_2]\cdot 6H_2O$. This compound has a tetrahedral arrangement of metal centres instead of a square arrangement and has no $CO_2$ absorption sites.
d) Repeating the experiment using varying amounts of the compound B.

The recorded mass spectra for the control experiments a)-c) show no change in the $CO_2$ concentrations (see FIG. 3). In the recorded spectra for experiment d) the intensity of the $CO_2$ peak increases with increasing concentrations of compound B (see FIG. 4). These experiments clearly demonstrate the underlying role that compounds A and B play in the pH-induced reversible capture and release of $CO_2$.

Figure 4:
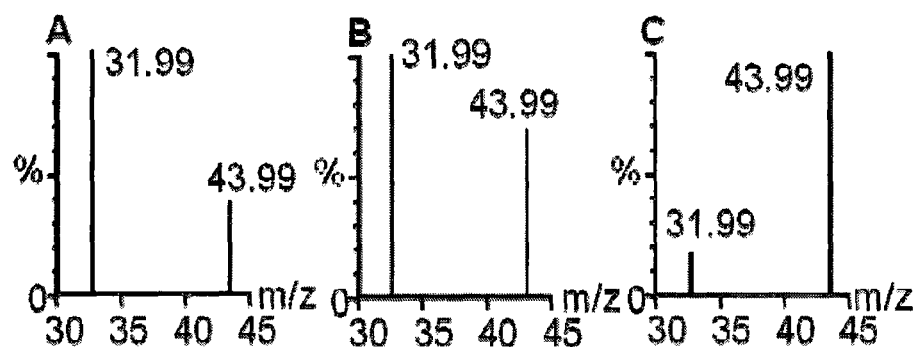
FIG. 4 is the Gas chromatography Mass spectra (GC-MS) recorded for headspace of GC-MS vial following the addition of an aqueous acid solution to a system containing 10, 20 and 50 mg of (enH)[$Fe_4(\mu\text{-}O)(\mu\text{-}OH)(hpdta)_2$ $(O_2CNHC_4H_8NH_3)_2$]$\cdot 6.5H_2O$ dissolved at pH8.5.

FIG. 4:=Gas chromatography Mass spectra (GC-MS) recorded for headspace of GC-MS vial following the addition of 0.061 µl of a 33% (v/v) aqueous $H_2SO_4$ solution to a system containing x mg of $(enH)[Fe_4(\mu\text{-}O)(\mu\text{-}OH)(hpdta)_2(O_2CNHC_4H_8NH_3)_2]\cdot 6.5H_2O$ dissolved in 1 ml of a $1.5\times 10^{-4}$ M aqueous ethylenediamine solution. A=10 mg, B=20 mg, C=50 mg.

Spectra A, B and C were recorded upon acidification of systems which contained 10 mg, 20 mg and 50 mg of the $CO_2$ trapping compound B respectively. The intensities of the $CO_2$ peaks increase and their relative intensities, compared to the $O_2$ peak at 31.99 m/z, change in response to the increasing concentrations of compound B. These observations further demonstrate the role that compound B plays in the acid induced $CO_2$ capture and release.

Figure 5:
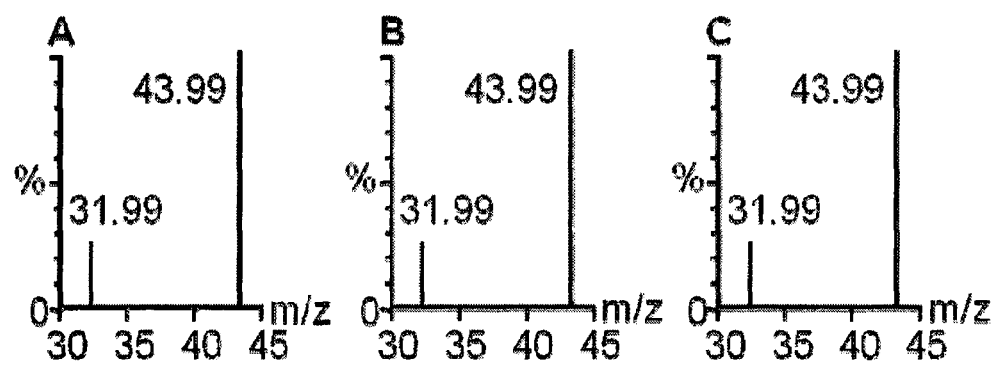
FIG. 5 is the Gas chromatography Mass spectra (GC-MS) recorded for headspace of GC-MS vial following the addition of aqueous acid to a series of systems containing $CO_2$ trapping analogues of compound B.

FIG. 5:=Gas chromatography Mass spectra (GC-MS) recorded for headspace of GC-MS vial following the addition of 0.06 µl of a 33% (v/v) aqueous $H_2SO_4$ solution to a system containing:
A=50 mg $(NH_2C_4H_8NH_3)$ $[Fe_4(\mu\text{-}O)(\mu\text{-}OH)(hpdta)_2(O_2CNHC_4H_8NH_3)_2]\cdot x(solvent)$ dissolved in 1 ml of a $1.4\times 10^{-4}$ M aqueous diaminobutane solution.
B=50 mg $(NH_2C_6H_{12}NH_3)$ $[Fe_4(\mu\text{-}O)(\mu\text{-}OH)(hpdta)_2(O_2CNHC_6H_{12}NH_3)_2]\cdot x(solvent)$ dissolved in 1 ml of a $1.4\times 10^{-4}$ M aqueous diaminobutane solution.
C=50 mg $\{Na(H_2O)_4\}[Fe^{III}_4(\mu\text{-}O)(\mu\text{-}OH)(hpdta)_2(CO_3)_2]\cdot 12H_2O$ dissolved in 1 ml of a $1.4\times 10^{-4}$ aqueous diaminobutane solution.

A, B and C were recorded upon acidification of systems which contained 50 mg of $w[Fe_4(\mu\text{-}O)(\mu\text{-}OH)(hpdta)_2(O_2CNHC_4H_8NH_3)_2]$.sol, $w[Fe_4(\mu\text{-}O)(\mu\text{-}OH)(hpdta)_2(O_2CNHC_6H_{12}NH_3)_2]$.sol and 50 mg $w[Fe^{III}_4(\mu\text{-}O)(\mu\text{-}OH)(hpdta)_2(CO_3)_2]\cdot 12H_2O$, respectively. These compounds are three examples of analogues of compound B. The increase in the intensity of the $CO_2$ peak at 43.99 m/z and its relative intensities compared to the $O_2$ peak at 43.99 m/z demonstrate the acid induced release of $CO_2$ from these systems.

Figure 6:
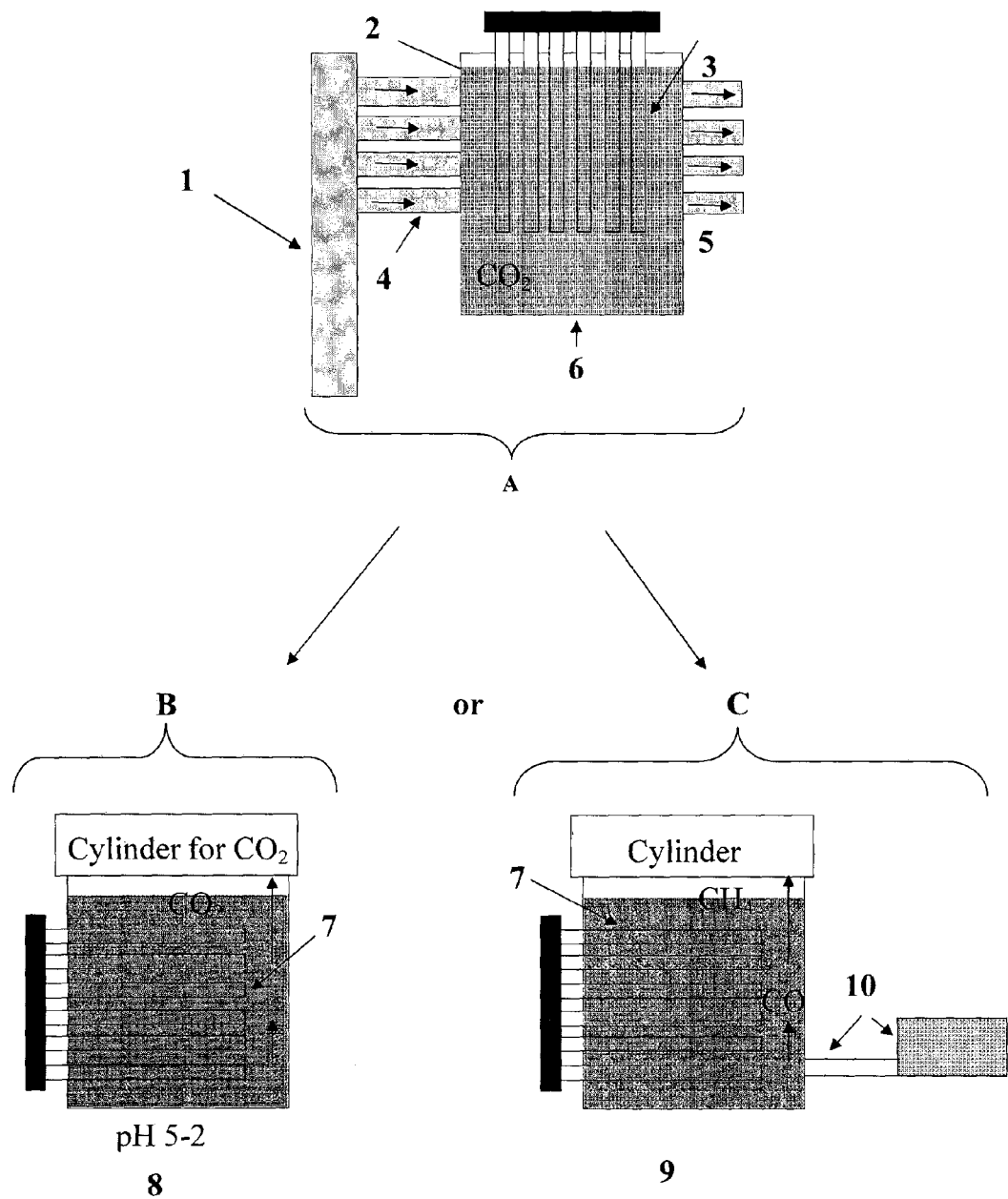
FIG. 6 is an example of a device that could be developed to capture $CO_2$ and either release it for storage or use renewable solar energy to transform it into fuels or useful chemicals.

FIG. 6: An example of a device that could be developed to capture $CO_2$ (A) and either release it for storage (which is the current happens to captured $CO_2$ except the current procedure requires temperatures in excess of 150° C. (B) or use renewable solar energy to transform it into fuels or useful chemicals (C). This process is completely regenerative and the compounds to be used to repeatedly capture ($CO_2$).

In FIG. 6:
1=Source of $CO_2$ emissions in this case is an industrial chimney stack.
2=Handle to facilitate the removal of the silica sheets upon completion of the $CO_2$ trapping process. (Completion time will vary depending on the amount of silica sheets utilised in the process).
3=Series of silica sheets covered with a monolayer of our $CO_2$ trapping compounds.
4=Flue gas rich in $CO_2$
5=Flue gas with $CO_2$ removed
6=Vessel containing aqueous alkaline media at pH 8.
7=Series of silica sheets from A covered with a monolayer of our $CO_2$ trapping compounds (The $CO_2$ selectively removed from the flue gases)
8=Vessel containing aqueous acidic media at pH between 5 and 2—allows for the release of $CO_2$ and regeneration of the $CO_2$ trapping compounds.
9=Vessel containing photosensitizer, sacrificial donor and Triethyanolamine at pH 8—allows for the proton assisted multi electron reduction of $CO_2$ to fuels and useful chemicals. Dipping the silica sheets in an aqueous acid solution (as seen in B) will regenerate the $CO_2$ trapping compounds.
10=Series of filters and storage container for fuels and useful chemicals.

FIG. 6 illustrates an example of a device that could be developed to capture $CO_2$ (A) and either release it for storage (which is the current happens to captured $CO_2$ except the current procedure requires temperatures in excess of 150° C. (B) or use renewable solar energy to transform it into fuels or useful chemicals (C). This process is completely regenerative and the compounds to be used to repeatedly capture ($CO_2$).

Further Experiments

An aspect of this invention involves the immobilisation of compounds A or B onto a support for the purposes of capturing $CO_2$ from any emission source and pH induced release of the $CO_2$ to regenerate the compound.

The compounds can be attached to surfaces that are functionalised with carboxylate moieties. In addition we know from extensive structural studies that the compounds are negatively charged and readily attach to positively charged surfaces via electrostatic forces. This allows the complexes of compound A and B to be immobilised on ion exchange membranes used and produced by industry. We anticipate that the compounds could also be attached through covalent bonds (e.g. co-polymerisation of modified ligand). Other examples of supports include, but are not limited to silicates, alumosilicates, oxides and phosphates, metals and metalloids. zeolitic materials, organic, inorganic and hydrid polymers.

The compounds in our system can be immobilised onto a range of surfaces coupled with their capacity to reversibly capture and release carbon dioxide by simple pH adjustment gives rise to their applications as innovative, economically viable sequestering agents in industry. The system can operate in mixed gas streams, is less energy intensive, operates under ambient conditions in an aqueous based system, captures 2 equivalent of $CO_2$ molecules per compound. The green technologies which could be developed using this approach can be adapted to suit the requirements of individual market places and can be incorporated into existing carbon capture and sequester systems which are already in place in industries across the globe.

The system also has the capability to absorb atmospheric $CO_2$ efficiently, which makes it highly useful for the removal of $CO_2$ from the environment. The technologies described may be readily customised to facilitate the removal of $CO_2$ from the atmosphere. The availability of such revolutionary technologies would initiate remediation measures that could accelerate the stabilisation of $CO_2$ concentrations and would facilitate future compliance with more stringent intergovernmental legislation.

Immobilisation of Tetranuclear Complexes on Solid Supports

Linkage Through Coordination Bonds Using Carboxylate Functionalities or Related Donor Atom Functionalities.

We have demonstrated that organic compounds with carboxylate functionalities strongly bind to metal complexes with the outlined core structure. This is in-line with the fixation of carbonates and carbamates by these complexes.

The affinity between carboxylates and the complexes with the described core structure can be demonstrated by the following experiments where bi-functional organic acids are used to link the tetranuclear complexes. The complexes may form in-situ in the reaction mixture or can be prepared using $w[Fe_4(\mu-O)(\mu-OH)(hpdta)_2(H_2O)_4]$.solv as starting material and reacting it with a organic compound.

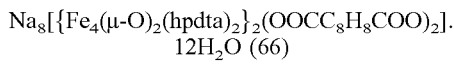

0.081 g (0.25 mmol) $H_5$hpdta was dissolved in 7.4 ml of distilled water by addition of 0.6 ml sodium hydroxide solution (2M). 0.135 g (0.5 mmol) $FeCl_3.6H_2O$ was added to the reaction mixture and the pH was adjusted to 7 by the slow addition of 1 ml (0.1M) sodium hydroxide solution. 0.024 g (0.125 mmol) of 3-(4-carboxy-phenyl)propionic acid was dissolved in 1 ml of 0.1 M sodium hydroxide solution and added to the reaction mixture followed by 5 ml dimethylacetamide. Dark green crystals of 66 formed after 4 days. The compound was dried for 24 hours at 120° C. Yield=54% FTIR (cm$^{-1}$) $v_{max}$: 3366 (s, br), 2970 (m), 1606 (s), 1466 (m), 1382 (s), 1306 (m), 1159 (s), 1128 (s), 913 (s).

Compound 66 can also be prepared by reacting compound A (complex that contains terminal water molecules) with 3-(4-carboxy-phenyl)propionicacid in aqueous solution. The corresponding Al(III) and Ga(III) compounds can also be isolated.

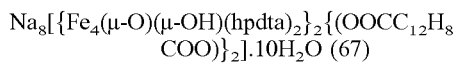

The synthetic procedure for 66 was repeated using 0.030 g (0.125 mmol) 4,4-biphenyl-dicarboxylic acid rather than 3-(4-carboxy-phenyl)propionic acid. Dark green crystals of 67, formed after 4 days. The compound was dried for 24 hours at 120° C. Yield=39%. FTIR (cm$^{-1}$) $v_{max}$: 3347 (s, br), 2958 (s), 2929 (s), 1599 (vs), 1550 (s), 1327 (vs), 1052 (m), 1001 (s), 913(s), 830 (m).

We further demonstrated that 67 can be prepared by reacting compound A (complex that contains terminal water molecules) with 4,4-biphenyl-dicarboxylic acid in aqueous solution. The corresponding Al(III) and Ga(III) compounds can also be isolated.

Figure 7:
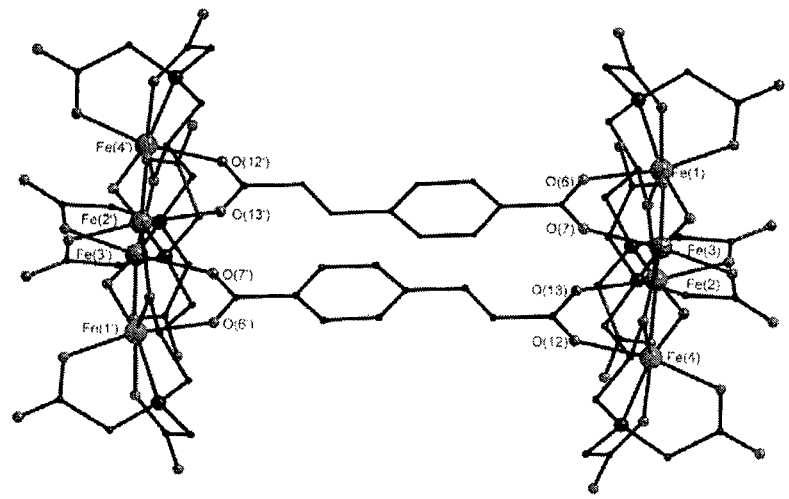
FIG. 7 shows the octanuclear complex [{$Fe_4(\mu\text{-}O)_2$(hpdta)$_2$}$_2$(OOCC$_8$H$_8$COO)$_2$]$^{8-}$ in 1. The hydrogen atoms have been omitted for clarity. The structure demonstrates that the tetranuclear complexes have a high affinity to react with carboxylate functionalities or related donor atom functionalities. Structure determined by X-ray crystallography.

FIG. 7 represents the octanuclear complex $[\{Fe_4(\mu-O)_2(hpdta)_2\}_2(OOCC_8H_8COO)_2]^{8-}$ in 66. The hydrogen atoms have been omitted for clarity. The structure demonstrates that the tetranuclear complexes have a high affinity to react with carboxylate functionalities or related donor atom functionalities. Structure determined by X-ray crystallography.

Figure 8:
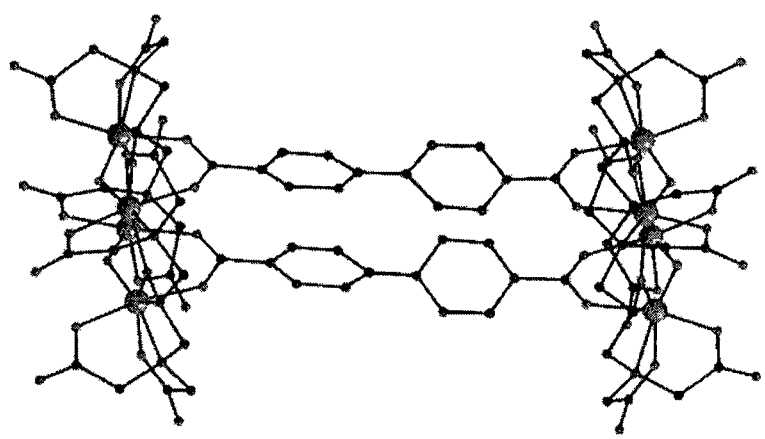
FIG. 8 shows the octanuclear complex [{$Fe_4(\mu\text{-}O)(\mu\text{-}OH)$ (hpdta)$_2$}$_2$\{(OOCC$_{12}$H$_8$COO)\}$_2$]$^{8-}$ in 2. The hydrogen atoms have been omitted for clarity. The structure demonstrates that the tetranuclear complexes have a high affinity to react with carboxylate functionalities or related donor atom functionalities. Structure determined by X-ray crystallography. Structure determined by X-ray crystallography.

FIG. 8 represents the octanuclear complex $[\{Fe_4(\mu-O)(\mu-OH)(hpdta)_2\}_2\{(OOCC_{12}H_8COO)\}_2]^{8-}$ in 67. The hydrogen atoms have been omitted for clarity. The structure demonstrates that the tetranuclear complexes have a high affinity to react with carboxylate functionalities or related donor atom functionalities. Structure determined by X-ray crystallography. Structure determined by X-ray crystallography.

Immobilisation of the Complexes on Solid Supports.
Immobilisation on Silicon Using Coordination Bonds.

The selectivity and the time scale of the substitution of the water ligands in $[Fe_4(\mu-O)(\mu-OH)(hpdta)_2(H_2O)_4]$ by carboxylates allows the complexes to be immobilised lateral boundaries, e.g. at porous Si surfaces. We have applied a synthetic approach (FIG. 9) which involves the following steps: a) deposition of carboxylate anchor groups on a Si surface and fixation of the carboxylate anchor groups on the Si surface by UV irradiation; (b) Dipping of the substrates into solutions containing tetranuclear $[Fe_4(\mu-O)(\mu-OH)(hpdta)_2(H_2O)_4]^-$ complexes. The immobilised complexes still remain the ability to fix and release $CO_2$ (as described in the previous section) depending on the pH of the surrounding media.

Figure 9:
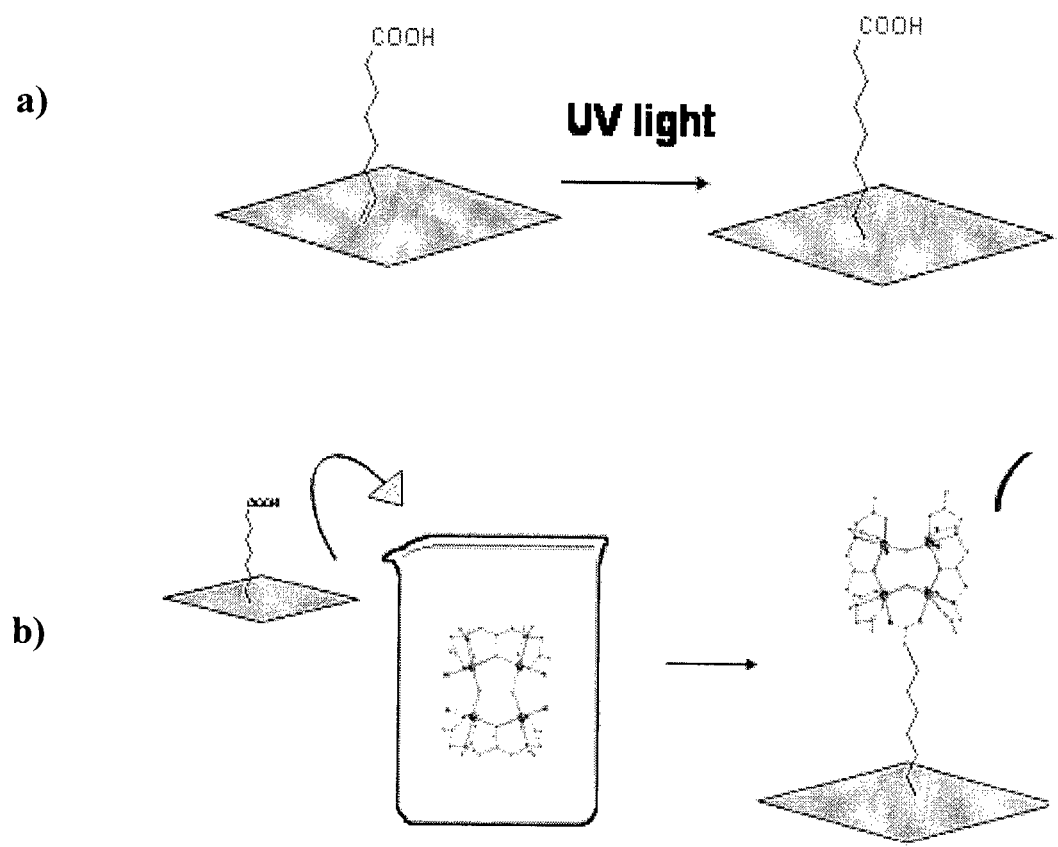
FIG. 9 shows a synthetic approach to immobilise the complexes on silicon-based supports. a) Deposition of carboxylate anchor groups on a Si surface and fixation of the carboxylate anchor groups on the Si surface by UV irradiation; b) Dipping of the substrates into solutions containing tetranuclear $Fe_4(\mu\text{-}O)(\mu\text{-}OH)(hpdta)_2(H_2O)_4]^-$ complexes.

FIG. 9 illustrates a synthetic approach to immobilise the complexes on silicon-based supports. a) Deposition of carboxylate anchor groups on a Si surface and fixation of the carboxylate anchor groups on the Si surface by UV irradiation; b) Immobilisation of tetranuclear complexes: Dipping of the Si substrates into solutions containing tetranuclear $Fe_4(\mu-O)(\mu-OH)(hpdta)_2(H_2O)_4]^-$ complexes.

Experimental Details

The functionalisation of hydrogen-terminated Si surfaces (100, 111 or 110) was achieved using an olefin reaction with UV-generated surface radicals. Si(111) and Si(100) specimen were cleaned for ca. 20 min at ca. 80° C. in a 2:1 $H_2SO_4:H_2O_2$ mixture and immersed for 30 seconds in 2.5% aqueous HF. Neat 4-pentenoic acid was spin-coated onto the Si-specimen. The sample was placed in a vacuum chamber and illuminated for ca. 16 h with UV light (254 nm, 9 mW/cm$^2$). The surfaces were washed with common organic solvents incl. methanol, ethanol and dichloromethane. The functionalisation of the surface was monitored using X-ray photoelectron spectroscopy (XPS) and Infrared or Raman spectroscopy. A similar functionalisation approach has been described by Bunimovichin et al. *Langmuir* 2004, 20, 10630-10638. The immobilization of the tetranuclear Fe(III) complexes was achieved by immersion the functionalised specimen into a solution that contains the dissolved tetranuclear $[Fe_4(\mu-O)(\mu-OH)(hpdta)_2(H_2O)_4]^-$ complexes (saturated solution) or a solution in which the tetranuclear complex is formed in-situ (solution A and B).

Solution A: 0.081 g (0.25 mmol) of $H_5$hpdta was dissolved in 1 mL distilled water and 1.3 mL of aqueous ammonia solution (2 M) were added. This solution of the ligand was then added under stirring to an aqueous solution of $Fe(NO_3)_3$ (1.25 mL of 0.4M). The resulting orange solution was further diluted and 4 mL of distilled water were added.

Solution B: 0.081 g (0.25 mmol) of $H_5$hpdta was dissolved in 5 mL distilled water and 0.5 1 mL of an aqueous NaOH solution (2 M) were added. Then an aqueous solution of $FeCl_3$ (5 mL, 0.1 M) was added dropwise under stirring.

The immobilisation of the complexes were confirmed by atomic force microscopy (AFM) and by Infrared spectroscopy revealing characteristic bands at ca. 2925 cm$^{-1}$, 1635 cm$^{-1}$, 1585 cm$^{-1}$. Mass spectrometry head space analyses confirmed that these immobilised complexes still remain the capability of fixing and releasing $CO_2$ when the pH value of the surrounding media is varied between 5.5 and 8.5.

Immobilisation on Resins, Ion Exchange Media, Membranes Using the Above Described Coordination Chemistry Approach The above describe immobilisation can be a achieved using other solid supports that contain free carboxylic acid moieties or related other O-donor groups including sulfonic acids, phosphate and phosphonate groups. For instance the immobilisation can be achieved using resins, ion exchange media and membranes that contain such moieties. For this purpose commercially available resins or membranes were immersed and stirred in solutions that contain the tetranuclear complexes (e.g. larger quantities of solution A and B). Alternatively, such solutions were passes through columns containing resins or ion exchange media.

Typical Experiments

The following DOW ion exchange resins were purchased: IMAC HP336, AMBERLITE™ IRC86SB, AMBERLITE™ IRC86SB, DOWEX™ MAC-3 and DOWEX™ MARATHON™ 650C(H). The resigns contain carboxylic acid and/or sulphonic acid groups.

5.0 g of each of the exchange resins were placed in a reaction flask and 100 mL of a saturated solution of the tetranuclear $[Fe_4(\mu\text{-}O)(\mu\text{-}OH)(hpdta)_2(H_2O)_4]^-$ complexes or solution A or B (quantities were scaled up) were added. The disperse reaction mixtures were stirred using a magnetic stirrer for 72 h. During this period the resins become slightly orange coloured.

Alternatively the above mentioned ion exchange resins were placed in a glass column and were continuously eluded with a concentrated solution of the tetranuclear $[Fe_4(\mu\text{-}O)(\mu\text{-}OH)(hpdta)_2(H_2O)_4]^-$ complexes or with larger quantities of solutions A or B for 24 h. Elemental analysis of the products confirms the immobilisation of the complexes. Infrared spectroscopy revealing characteristic bands at ca. 2925 $cm^{-1}$, 1635 $cm^-$, 1585 $cm^{-1}$ also strongly suggests that the tetranuclear complexes are immobilised on these solid supports. Mass spectrometry head space analyses confirmed that these immobilised complexes still remain the capability of fixing and releasing $CO_2$ when the pH value of the surrounding media is varied between 5.5 and 8.5.

The above described method can also be adapted to cation exchange membranes (CEM) e.g. Nafion series and Fumasep FKB, FKS and FK-40. Our scientific evidence suggests that many commercially available cation exchange membranes (Table 1) can be used for the immobilisation purposes using the outlined principle.

TABLE 1

Selection of ion exchange membranes suitable for the immobilization of the complexes.

| Membrane | Type |
|---|---|
| Asahi Chemical Industry Co Japan | |
| Aciplex K-192 | CEM |
| Aciplex-501SB | CEM |
| Aciplex A-192 | AEM |
| Aciplex-501SB | AEM |
| Aciplex A201 | AEM |
| Aciplex A221 | AEM |
| Asahi Glass Co., Ltd., Japan | |
| Selemion CMV | CEM |
| Selemion AMV | AEM |
| Selemion ASV | AEM |
| Selemion DSV | AEM |
| Flemion | — |
| DuPont Co., USA | |
| Nafion NF-112 | CEM |
| Nafion NF-1135 | CEM |
| Nafion NF-115 | CEM |
| Nafion N-117 | CEM |
| FuMA-Tech GmbH. Germany | |
| FKS | CEM |
| FKB | CEM |
| FK-40 | CEM |
| FKD | CEM |
| FAS | AEM |
| FAB | AEM |
| FAN | AEM |
| FAA | AEM |
| FAD | AEM |
| Ionics Inc., USA | |
| CR61-CMP | CEM |
| CR67-HMR | CEM |
| CR67-HMP | — |
| AR103QDP | AEM |
| AR204SZRA | AEM |
| AR112-B | AEM |
| MEGA a.s., Czech Republic | |
| Ralex MH-PES | AEM |
| Ralex AMH-5E | AEM |
| Ralex CM-PES | CEM |
| Ralex CMH-5E | CEM |
| PCA Polymerchemie Altmeier GmbH, | |
| PC 100 D | AEM |
| PC 200 D | AEM |
| PC Acid 35 | AEM |
| PC Acid 70 | AEM |
| PC Acid 100 | AEM |
| PC-SK | CEM |
| PC-SA | AEM |
| Solvay S.A., Belgium | |
| Morgane CDS | CEM |
| Morgane CRA | CEM |
| Morgane ADP | AEM |
| Morgane AW | AEM |
| Tokuyama Co., Japan | |
| Neosepta CM-1 | CEM |
| Neosepta CM-2 | CEM |
| Neosepta CMX | CEM |
| Neosepta CMS | CEM |
| Neosepta CMB | CEM |
| Neosepta AM-1 | AEM |
| Neosepta AM-3 | AEM |
| Neosepta AMX | AEM |
| Neosepta AHA | AEM |
| Neosepta ACM | AEM |
| Neosepta ACS | AEM |
| Neosepta AFN | AEM |
| Neosepta AFX | AEM |
| Tianwei Membrane Co., Ltd., China | |
| TWEDG | AEM |
| TWDDG | AEM |
| TWAPB | AEM |
| TWANS | AEM |
| TWAHP | AEM |
| TWAEDI | AEM |
| TWCED | CEM |
| TWCDD | CEM |
| TWCEDI | CEM |

CEM: Cation Exchange Membrane
AEM: Anion Exchange Membrane

Linkage Through Electrostatic Interactions Between the Tetranuclear Complexes and Solid Support.

The tetranuclear complexes can be attached or incorporated into solid supports through electrostatic interactions whereby the resulting materials preserves the ability to fix and release $CO_2$ depending on the pH of the surrounding medium. We demonstrated this principle using the iron(III) complexes. These $CO_2$ fixing $[Fe_4(\mu\text{-}O)(\mu\text{-}OH)(hpdta)_2(H_2O)_4]^-$ complexes are characterised by a negative charge of −1. Upon fixation of $CO_2$ the negative charge increase, e.g. to −5 in $[Fe_4(\mu\text{-}O)(\mu\text{-}OH)(hpdta)_2(CO_3)_2]^{5-}$. The complexes can bind to positively charged supports, including resins, ion exchange media, membranes, metal-organic frameworks, silica (or other solid supports that carry a positive charge).

Typical Experiments

Experiments similar to those described in 3.1.3.1 were carried out using the following DOW anion exchange resigns: DOWEX™ MARATHON™ A, DOWEX™ UPCORE Mono MA-600, DOWEX™ SBR LC NG, DOWEX™ MONOSPHERE™ 550A, DOWEX™ 21K 16/30, AMBERJET™ 45000H, AMBERLITE™ IRA958 CL, AMBERLITE™ FPA42 CI, DUOLITE AP143/1083, DOWEX™ 22, AMBERSEP™ 920U.

5 g of each of the exchange resins were placed in a reaction flask and 100 mL of a saturated solution of the tetranuclear $[Fe_4(\mu\text{-}O)(\mu\text{-}OH)(hpdta)_2(H_2O)_4]^-$ complexes or solutions A or B (quantities were scaled up) were added. The disperse reaction mixtures were stirred using a magnetic stirrer for 72 h. During this period the resigns become slightly orange coloured. Alternatively the above mentioned ion exchange resins were placed in glass columns and were continuously eluded with a concentrated solution of the tetranuclear Fe complexes or with larger quantities of Solution A or B for 24 h. Best results were obtained when the anion exchange resins were treated with saturated solutions that contain the tetranuclear complexes. Elemental analysis of the products confirms the immobilisation of the complexes. Infrared spectroscopy revealing characteristic bands at ca. 2925 $cm^{-1}$, 1635 $cm^{-1}$, 1585 $cm^{-1}$ also strongly suggests that the tetranuclear complexes are immobilised on these solid supports. Mass spectrometry head space analyses confirmed that these immobilised complexes still remain the capability of fixing and releasing $CO_2$ when the pH value of the surrounding media is varied between 5.0 and 8.5.

The above described method that attaches the complexes electrostatically, can also be adapted to anion exchange membranes e.g. Fumasep FAA/FAB, Morgane ADP, Morgane AW and Aciplex K-192. Our scientific evidence suggests that anion exchange membranes listed in Table 1 can be used for immobilisation purposes using the outlined principle. In addition solid supports that combine features described in 3.1 and 3.2 can be used to immobilise the complexes. For instance weak acid-strong base type charge-mosaic membranes for instance described by Isono et al. in *Journal of Membrane Science*, 1989, 43,205 were used in the above described experiments and give excellent results. Zeolites and mesoporous silicates, alumophosphates and gallophosphates and metal organic frameworks may also be utilised to electrostatically immobilise the complexes.

Immobilisation of the Complexes Using Alumosilicates, Silicates and Other Porous Materials Utilising the Principles Described Above The unique properties of mesoporous silica (MPS) materials were utilized to immobilize the complexes. MPS are characterised by huge surface areas, modifiable surfaces, and restricted but accessible pore nanospaces. Appropriate surface silanols can be modified with a variety of organic functionalities for immobilizing the tetranuclear complexes. Surface functionalisation allows the introduction of carboxylate, phosphate, phosphonate, amino or organoammonium groups. It further provides a means to influence the charge of the MPS materials. The approach allows the linkage of the complexes through coordination bonds (see section 3.1) or electrostatic interactions (see section 3.2). We demonstrated this approach using MCM-41 and SBA-15. However the approach is generally applicable and valid for other mesoporous materials, e.g. those listed in Table 2.

TABLE 2

Selection of mesoporous materials suitable for the immobilisation of the tetranuclear complexes.

| Mesoporous materials | Silica source | Mesoporous materials | Silica source |
|---|---|---|---|
| MCM-41 | TEOS, sodium silicate | SBA-16 | TEOS, TMOS |
| | | MCF | TEOS |
| MCM-48 | TEOS, sodium silicate | HMS | TEOS |
| | | MSU-X | TEOS, TMOS |
| FSM-16 | Polysiticate kanemite | IBN-X | TEOS |
| | | PMOs | $(RO)_3Si-R'-Si(OR)_3$ |
| SBA-1 | TEOS | | |
| SBA-15 | TEOS, sodium silicate | | |

Experimental Details

MCM-41 was prepared according to M. Grün et. al. *Adv. Mater.* 1997, 9254 or C.-F. Cheng et al. *J. Chem. Soc., Faraday Trans.*, 1997, 93, 193. The X-ray diffractograms of the obtained materials reveal the three well-resolved signals 2θ<60, corresponding to the (100), (110) and (200) reflections. Calcinations allowed the removal of the templates decomposing them into CO2, some NOx and $H_2O$, SBA-15 samples were synthesised by using a nonionic triblock copolymer as template previously described by Zhao et al. *Science* 1998, 279, 548. 4 g of the Pluronic copolymer 123 was solubilised in 125 mL of deionised $H_2O$ and 20 mL of conc. HCl and heated under stirring to ca. 305 K for 16 h. After this period 8.5 g of tetraethyl orthosilicate (TEOS) was added and the resulting solution was stirred at 305 K for further 24 h. Then, the reaction mixture was transferred into a Teflon-lined autoclave and heated at ca. 373 K for 24 h. After the reaction the product was filtered off and washed. The resulting solid was dried at 313 K and afterwards calcined at 823 K for 5 h. The XRD pattern of calcined SBA-15 showed two peaks at 2θ-1.62 and 1.81°, which correspond to the (110) and (200) reflections. From a nitrogen adsorption experiment, the BET surface area of the calcined SBA-15 was found to be 910 $m^2g^{-1}$.

For Functionalisation of Mesoporous Silicas:

Method A:

4.0 g of mesoporous silica was treated with 2% v/v 3-aminopropyltriethoxysilane solution in dry toluene (40 mL). The mixture was heated in an $N_2$ atmosphere under for 16 h. The product was filtered off, washed with acetone, and at 80° C. under vacuum (Salis et al., *Langmuir*, 2005, 21, 5511.

Method B:

1.0 g of calcined SBA-15 was added to 30 ml of 1,4-dioxane. Then 4 mmol 4-(triethoxysilyl)butyronitrile was added per gram of silica support and the reaction mixture was heated under $N_2$ to reflux for 24 h. The white solid was filtered off, washed with diethyl ether (60 mL) and dried under vacuum. SBA-15 was refluxed in 1M HCl solution for 4 h to convert the nitrile functionality into an acid functionality (*J. Mol. Cat. B: Enzym.*, 2001, 15, 81).

Immobilisation of Tetranuclear Complexes (Experimental Procedure as Above)

5.0 g of each MCM-41 or SBA-15 were placed in a reaction flask and 100 mL of a saturated solution of the tetranuclear [Fe$_4$($\mu$-O)($\mu$-OH)(hpdta)$_2$(H$_2$O)$_4$]$^-$ complexes or solution A or B (quantities were scaled up) were added. The disperse reaction mixtures were stirred using a magnetic stirrer for 72 h. During this period the silicas become orange coloured. Alternatively MCM-41 or SBA-15 were placed in a glass column and were continuously eluded with a concentrated solution of the tetranuclear [Fe$_4$($\mu$-O)($\mu$-OH)(hpdta)$_2$(H$_2$O)$_4$]$^-$ complexes or with larger quantities of solutions A or B for 24 h. Elemental analysis of the products confirms the immobilisation of the complexes. Infrared spectroscopy revealing characteristic bands at ca. 2925 cm$^{-1}$, 1635 cm$^{-1}$, 1585 cm$^{-1}$ also strongly suggests that the tetranuclear complexes are immobilised on these solid supports. Mass spectrometry head space analyses confirmed that these immobilised complexes still remain the capability of fixing and releasing CO$_2$ when the pH value of the surrounding media is varied between 5.5 and 8.5.

FIG. 9 Functionalisation approach for silica materials.

Adsorption of the Complexes on Solid Supports.

Physical adsorption methods provide a simple approach to immobilize the above complexes on solid supports. This approach has no effect on the active sites of the complexes and they maintain their ability to fix and release CO$_2$. The complexes attach through wreaker electrostatic interactions, H-bonds, van der Waals forces and etc. to the solids. The above complexes are applicable for this immobilisation approach. We tested this methodology using the mesoporous silicas MCM-41 and SBA-15 and a range of commercially available solids and gels including silica gel, SiO$_2$ powder, starch, cellulose, poly glucose, and the zelolites ZSM-5, faujasite NaY, NaX, sodalite and dodecasil 1H (further suitable zeolite materials are listed below). In addition we used MOF-177 (H. Furukawa et. al. *J. Mater. Chem.* 2007, 17, 3197; MOF-180, MOF-200. MOF-205 and MOF-210 (Furukawa et. al. *Science*, 2010, 329, 424) for these adsorption experiments.

In a typical procedure ca. 5 g of the soils were immersed in saturated solutions of the tetranuclear complexes. IR analysis suggests that all tested solids adsorb to certain degree the complexes which maintain their functionality as demonstrated by CO$_2$ absorption and release studies. In some cases, however, after some CO$_2$ absorption and release cycles, the complexes leach out of the solids resulting in a reduction of the activity of the products.

TABLE 3

Selection of zeolytic materials suitable for the immobilisation of the complexes.

| Low silica Si/Al ≤ 2 | Intermediate silica 2 < Si/Al ≤ 5 | High silica 5 < Si/Al |
|---|---|---|
| ABW, Li-A(BW) | BHP, line Q | ASV, ASU-7 |
| AFG, afghanite[a] | BOG, boggsite[a] | BEA, zeolite β |
| ANA, analcime[a] | BRE, brewsterite[a] | CFI, CIT-5 |
| BIK, bikitaite[a] | CAS, Cs-aluminosilicate | CON, CIT-1 |
| CAN, cancrinite[a] | CHA, chabazite[a] | DDR, decadodelcasil 3R |
| EDI, edingtonite[a] | CHI, chiavennite[b] | DOH, dodecasil 1H |
| FAU, NaX | DAC, dachiardite[a] | DON, UTD-1F |
| FRA, franzinite | EAB, EAB | ESV, ERS-7 |
| GIS, gismondine[a] | EMT, hexagonal faujasite | EUO, EU-1 |

TABLE 3-continued

Selection of zeolytic materials suitable for the immobilisation of the complexes.

| Low silica Si/Al ≤ 2 | Intermediate silica 2 < Si/Al ≤ 5 | High silica 5 < Si/Al |
|---|---|---|
| GME, gmelinite[a] | EPI, epistilbite[a] | FER, ferrierite[a] |
| JBW, NaJ | ERI, erionitea | GON, GUS-1 |
| LAU, laumonite[a] | FAU, faujasite[a], NaY | IFR, ITQ-4 |
| LEV, levyne[a] | FER, ferrierite[a] | ISV, ITQ-7 |
| LIO, liottite[a] | GOO, goosecreekite[a] | ITE, ITQ-3 |
| LOS, losod | HEU, heulandite[a] | LEV, NU-3 |
| LTA, linde Type A | KFI, ZK-5 | MEL, ZSM-11 |
| LTN, NaZ-21 | LOV, lovdarite[b] | MEP, melanopholgite[a] |
| NAT, natrolite[a] | LTA, ZK-4 | MFI, ZSM-5 |
| PAR, partheite[a] | LTL, linde L | MFS, ZSM-57 |
| PHI, phillipsite[a] | MAZ, mazzite[a] | MSO, MCM-61 |
| ROG, roggianite[a] | MEI, ZSM-18 | MTF, MCM-35 |
| SOD, sodalite | MER, merlinoite[a] | MTN, dodecasil 3C |
| WEN, wenkite[a] | MON, montasommaite[a] | MTT, ZSM-23 |
| THO, thomsonite[a] | MOR, mordenite[a] | MTW, ZSM-12 |
| TSC, tschortnerite | OFF, offretite[a] | MWW, MCM-22 |
| | PAU, paulingite[a] | NON, nonasil |
| | RHO, rho | NES, NU-87 |
| | SOD, sodalite | RSN, RUB-17 |
| | STI, stilbite[a] | RTE, RUB-3 |
| | YUG, yugawaralite[a] | RTH, RUB-13 |
| | | RUT, RUB-10 |
| | | SFE, SSZ-48 |
| | | SFF, SSZ-44 |
| | | SGT, sigma-2 |
| | | SOD, sodalite |
| | | STF, SSZ-35 |
| | | STT, SSZ-23 |
| | | TER, terranovaite |
| | | TON, theta-1 |
| | | ZSM-48 |
| | | VET, VPI-8 |
| | | VNI, VPI-9 |
| | | VSV, VPI-7 |

[a]Natural materials;
[b]Beryllosilicates (natural).

Encapsulation of the Tetranuclear Complexes In-Situ During the Synthesis of the Solid Support Materials Many of the above complexes show good stabilities at different pH values and at higher temperatures. These feature allow their in-situ encapsulation and immobilisation during the synthesis of solid supports. To validate this approach we performed the following experiments:

4.0 g of fumed silica, 3.2 g of NaOH, 0.30 g of the appropriate tetranuclear complex and 8.0 ml of H$_2$O were stirred for 30 min. To this solution, sodium aluminate (prepared from 9 g of Al(iOPr)$_3$, 3.2 g of NaOH and 36 ml H$_2$O) was added. The resulting gel was then transferred to a polypropylene container and aged 24 h at room temperature under stirring. The mixture was then heated to 85° C. for 24 h. The mixture was then allowed to cool to room temperature and diluted with copious amounts of deionized water. The solid was collected, dried at 80° C. for 24 h in air and washed with acetonitrile. It was finally dried at 80° C. under vacuum (1×10$^{-3}$ Torr) for 15 h. (Method modified from: *J. Mol. Cat. A: Chem.* 1998, 135, 295-306). Infrared and CHN analyses confirmed the immobilisation of the tetranuclear complexes.

The tetranuclear complexes were also added to the synthesis mixtures of MCM-41 and SBA-15 (see experimental details above) allowing the incorporation of the complexes in solid materials as demonstrated by infrared spectroscopy and elemental analyses. To improve the surface area of the materials and remove the templates, extraction methods similar to those described in *Chem Rev.* 2002, 102, 3589 were applied.

Application of 'Flexible Ligand' and 'Ship in the Bottle' Methods to Immobilise the Complexes in Solids 'Flexible ligand' and 'ship in the bottle' synthetic methodologies take advantage of the assembly of the tetranuclear metal complexes within the pores, channels and void spaces of porous materials. The size, geometry and chemical nature of the resulting complexes entraps the complexes in the pores of the porous materials restricting leaching through small pore openings of the porous materials.

We demonstrated that this approach can be utilised to immobilise the tetranuclear complexes using a range of materials including IM-12 (Paillaud et al., Science, 2004, 304, 990), VPI-5 (Breck, D. W. Zeolite Molecular SieVes; Krieger: Malabar, Fla., 1984; p 65), ECR-34 (Strohmaier et al., J. Am. Chem. Soc. 2003, 125, 16035), ITQ-15 (Corma et. al. Chem. Commun., 2004, 1356), MCM-41, SBA-15, MOF-177 (H. Furukawa et. al. J. Mater. Chem. 2007, 17, 3197; MOF-180, MOF-200, MOF-205, MOF-210 (Furukawa et. al. Science, 2010, 329, 424); UMCM-2 (K. Koh et. al. J. Am. Chem. Soc. 2009, 131, 4184) and MIL-101c (G. Férey et al., Science 2005, 309, 2040; Llewellyn et al., Langmuir 2008, 24, 7245).

Prior to the experiment, the above mentioned solids were heat treated to remove constitutional solvent molecules or solvent molecules were removed through activation processes using organic solvents (Furukawa et. al. Science, 2010, 329, 424). Materials were stored under vacuum. In a typical experiment, 3.0 g of the above named solids were first immersed in 200 mL of saturated aqueous M(III) solutions (M-Fe(III), Al(III) and Ga(III)). The solids were then heat-treated and transferred into a sinter funnel and saturated solutions of the sodium salts of the $H_5$hpdta ligand were continuous passed over the solids under suction. Alternatively M(III)-impregnated solids were stirred in solutions of the sodium salts of the $H_5$hpdta ligand for several hours. IR analyses suggest that tested solids contain the respective tetranuclear complexes which maintain their functionality as demonstrated by $CO_2$ absorption and release studies.

Immobilisation of the Complexes Through Covalent Binding and Chelating Resins

The tetranuclear metal complexes can also be attached to solid supports through covalent bonds. Diaminetetraacetic acids with similar structure to the here described hpdta ligand can be functionalised at the methylene groups of the acetic acid moieties or at the methylene groups of the diamine backbone. Functionalisation approaches e.g. described in Synthesis, 1989, 11, 825, J. Chem. Soc., Perkin Trans. 1989, 1, 1781, Chemistry Letters 2005, 34, 1098 or Synthetic Communications, 2005, 35, 2415 can be applied to hpdta-type ligands. The ligands and the complexes can be co-polymerised in polyethylene, polypropylene, polystyrene, polyacrylonitrile, PVC and etc. Based on our experiments as outlined above, we can expect that the complexes maintain their $CO_2$ capture and release capability.

Figure 10:
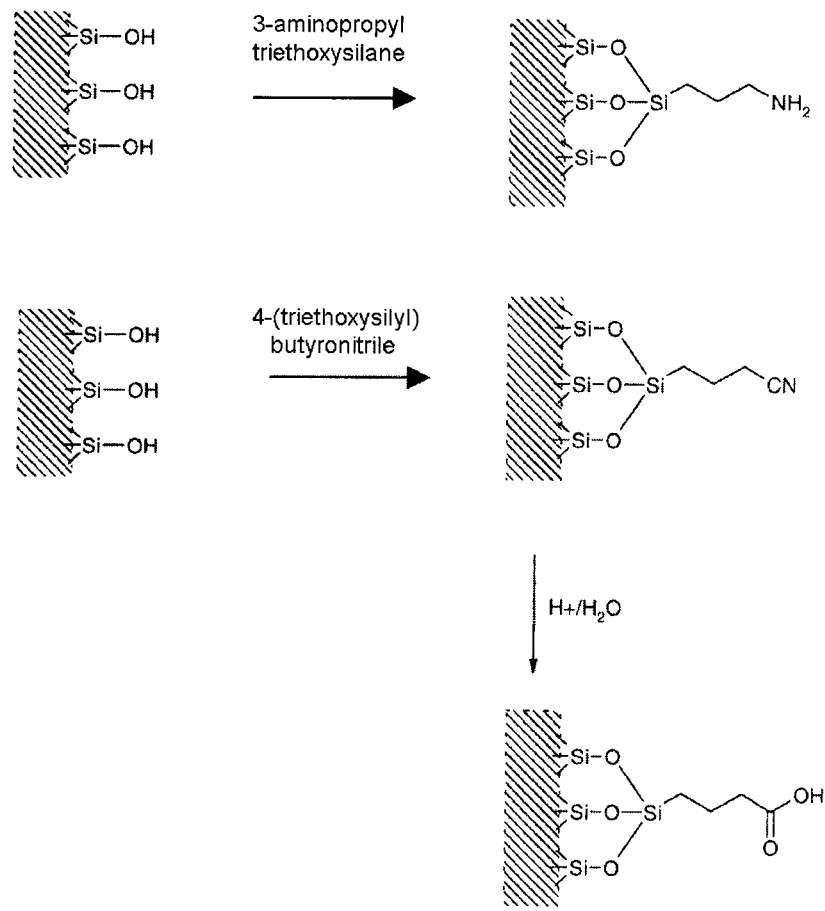
FIG. 10 illustrates functionalisation approaches for silica materials.

The introduced functional groups further allow covalent attachment of the ligands and their tetranuclear complexes to mesoporous materials through covalent bonds. Mesoporous materials like MCM-41 and SBA-15 (FIG. 10) can be modified by a series of organosilanes including amine, thiol, chloride, cyano, ester, epoxy, aldehyde, anhydride, isocyanato, phospho, imidazole, ammonium, acryl, alkyl, and phenyl groups (Yiu et. al. J. Mol. Catal. B: Enzym, 2001, 15, 81). These functional groups can covalently attached to structurally modified $H_5$hpdta ligands that contain complementary functional groups.

The invention offers an environmentally sustainable and economically viable green technology that could be used to:

A) Capture $CO_2$ from flue gas emissions in pre, post and oxy-combustion carbon capture technologies.
B) Minimise the $CO_2$ content in gas mixtures required for many industrial processes (e.g. processes that use catalysts, $NH_3$ synthesis, the large scale commercial production of hydrogen, oil refining etc.)
C) Separate carbon dioxide from biogases to increase the methane ($CH_4$) content. (Using $CO_2$ capturing green technologies offers a less energy intensive option to remove $CO_2$ from the biogas which upgrades the quality of the biogases to a quality similar to natural gas.)
D) Develop innovative remediation technologies to facilitate the removal of $CO_2$ from the atmosphere
E) Develop smaller devices which have the ability to capture $CO_2$ from a variety of emission sources e.g. aviation, vehicle exhausts', home heating systems etc.
F) A range of industrially important membranes and porous materials whose composition and properties can be tailored to several industrial application and specific plant requirements.

Each reference which is mentioned in this specification is incorporated herein in its entirety.

Various aspects described with reference to one embodiment may be utilised, as appropriate, with any other embodiment(s).

The invention is not limited to the embodiments hereinbefore described which may be varied in detail.

The invention claimed is:

1. A method for reversible capture and release of carbon dioxide comprising the steps of:
providing a solution comprising a tetranuclear complex or mixture thereof, in which adsorption sites are provided by coordinated solvent molecules;
exposing the solution to a gas comprising carbon dioxide to sequester carbon dioxide by forming a reaction mixture; and
adjusting the pH of the reaction mixture to facilitate a release of carbon dioxide,
wherein the solution which is used to sequester carbon dioxide comprises a tetranuclear metal compound of formula:

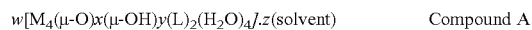

wherein the reaction mixture comprises a tetranuclear metal compound of formula:

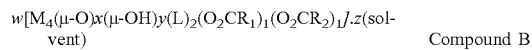

and wherein adjusting the pH of the reaction mixture produces Compound A, resulting in the release of carbon dioxide;
wherein
w is an ion or a mixture of ions in a stoichiometry such that Compound A and Compound B are electronically neutral,
M is selected from one or more of Fe, Al, and Ga; or one or more of Mn, Ru, Zn, Cr, Co, Ni, In, Cu, and V,
x and y are numerical values the sum of which equals to 2,
L is an aminocarboxylic acid ligand that stabilises the tetranuclear complex,
$R_1$ and $R_2$ are groups independently selected from:
an oxygen atom, an OH group, a hydrazine moiety, a hydrazinium moiety, an ammonia moiety, an ammonium moiety, a primary, secondary, or tertiary aliphatic amine, or derivative thereof; a primary, secondary, or tertiary aromatic amine, or derivative thereof; a diamine, a triamine, an alcohol amine or corresponding ammonium moiety; or wherein $O_2CR_1$ or $O_2CR_2$ is a carbamate group or a carbamic acid moiety, z is 0 or a positive number, and solvent is a solvent.

2. A method as claimed in claim 1 wherein the pH of the reaction mixture comprising the tetranuclear complex of Compound A is adjusted from a pH of between 14 and 7.9 to a pH of less than 7.8 by addition of one or more aliquots of acidic media.

3. A method as claimed in claim 1 wherein the release of carbon dioxide occurs when Compound B is dissolved in aqueous media at a pH of less than 7.8.

4. A method as claimed in claim 3 wherein the pH of the reaction mixture comprising the tetranuclear complex of Compound A is adjusted from a pH of about 8.5 to a pH of about 4.

5. A method as claimed in claim 1 wherein M is selected from one or more of Fe, Al, Cu, Ga, Mn, and Cr.

6. A method as claimed in claim 1 wherein L is

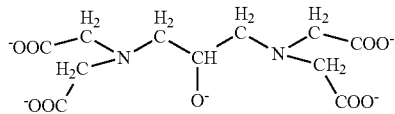

(hpdta) or a derivative thereof.

7. A method as claimed in claim 1 wherein the solvent comprises a polar solvent selected from $H_2O$, methanol, ethanol, propanol, isopropanol, DMF (dimethylformamide), DMA (dimethyl acetamide), DEF (diethylformamide), DEA (diethylacetamide), DMSO (dimethyl sulfoxide), acetonitrile, and mixtures thereof.

8. A method as claimed in claim 6 wherein Compound B is selected from:

$w[Fe^{III}_4(\mu-O)(\mu-OH)(hpdta)_2(CO_3)_2].z(solvent)$ (1), $w[Fe_4(\mu-O)(\mu-OH)(hpdta)_2(O_2CNHC_3H_6NH_3)_2].z(solvent)$ (2), $w[Fe_4(\mu-O)(\mu-OH)(hpdta)_2(O_2CNHNH_3)_2].z(solvent)$ (3), $w[Fe_4(\mu-O)(\mu-OH)(hpdta)_2(O_2CNHC_4H_8NH_3)_2].z(solvent)$ (4), $w[Fe_4(\mu-O)(\mu-OH)(hpdta)_2(O_2CNHC_6H_{12}NH_3)_2].z(solvent)$ (5), $w[Fe_4(\mu-O)(\mu-OH)(hpdta)_2(O_2CNHC_7H_{14}NH_3)_2].z(solvent)$ (6), $w[Fe_4(\mu-O)(\mu-OH)(hpdta)_2(O_2CNHC_2H_4NC_4H_8NH_2)_2].z(solvent)$ (7), $w[Fe_4(\mu-O)(\mu-OH)(hpdta)_2(O_2CNHC_3H_7)_2].z(solvent)$ (8), $w[Fe_4(\mu-O)(\mu-OH)(hpdta)_2(O_2CNHCH_2CH_2HNCH_2CH_2NH_3)_2].z(solvent)$ (9), $w[Fe_4(\mu-O)(\mu-OH)(hpdta)_2(O_2CNHCH_2CH_2OH)_2].z(solvent)$ (10), $w[Fe_4(\mu-O)(\mu-OH)(hpdta)_2(O_2CNHC_2H_4NH_3)_2].z(solvent)$ (11), $w[Al^{III}_4(\mu-O)(\mu-OH)(hpdta)_2(CO_3)_2].sol$  $w[Al^{III}_4(\mu-O)(\mu-OH)(hpdta)_2(CO_3)_2].(solvent)$ (12), $w[Al_4(\mu-O)(\mu-OH)(hpdta)_2(O_2CNHC_2H_4NH_3)_2].z(solvent)$ (13), $w[Al_4(\mu-O)(\mu-OH)(hpdta)_2(O_2CNHNH_3)_2].z(solvent)$ (14), $w[Al_4(\mu-O)(\mu-OH)(hpdta)_2(O_2CNHC_4H_8NH_3)_2].z(solvent)$ (15), $w[Al_4(\mu-O)(\mu-OH)(hpdta)_2(O_2CNHC_6H_{12}NH_3)_2].z(solvent)$ (16), $w[Al_4(\mu-O)(\mu-OH)(hpdta)_2(O_2CNHC_7H_{14}NH_3)_2].z(solvent)$ (17), $w[Al_4(\mu-O)(\mu-OH)(hpdta)_2(O_2CNHC_2H_4NC_4H_8NH_2)_2].z(solvent)$ (18), $w[Al_4(\mu-O)(\mu-OH)(hpdta)_2(O_2CNHC_3H_7)_2].z(solvent)$ (19), $w[Al_4(\mu-O)(\mu-OH)(hpdta)_2(O_2CNHCH_2CH_2HNCH_2CH_2NH_3)_2].z(solvent)$ (20), $w[Al_4(\mu-O)(\mu-OH)(hpdta)_2(O_2CNHCH_2CH_2OH)_2].z(solvent)$ (21), $w[Cu^{III}_4(\mu-O)(\mu-OH)(hpdta)_2(CO_3)_2].(solvent)$ (22), $w[Cu_4(\mu-O)(\mu-OH)(hpdta)_2(O_2CNHC_2H_4NH_3)_2].z(solvent)$ (23), $w[Cu_4(\mu-O)(\mu-OH)(hpdta)_2(O_2CNHC_2H_4NH_3)_2].z(solvent)$ (24), $w[Cu_4(\mu-O)(\mu-OH)(hpdta)_2(O_2CNHNH_3)_2].z(solvent)$ (25), $w[Cu_4(\mu-O)(\mu-OH)(hpdta)_2(O_2CNHC_4H_8NH_3)_2].z(solvent)$ (26), $w[Cu_4(\mu-O)(\mu-OH)(hpdta)_2(O_2CNHC_6H_{12}NH_3)_2].z(solvent)$ (27), $w[Cu_4(\mu-O)(\mu-OH)(hpdta)_2(O_2CNHC_7H_{14}NH_3)_2].z(solvent)$ (28), $w[Cu_4(\mu-O)(\mu-OH)(hpdta)_2(O_2CNHC_2H_4NC_4H_8NH_2)_2].z(solvent)$ (29), $w[Cu_4(\mu-O)(\mu-OH)(hpdta)_2(O_2CNHC_3H_7)_2].z(solvent)$ (30), $w[Cu_4(\mu-O)(\mu-OH)(hpdta)_2(O_2CNHCH_2CH_2HNCH_2CH_2NH_3)_2].z(solvent)$ (31), $w[Cu_4(\mu-O)(\mu-OH)(hpdta)_2(O_2CNHCH_2CH_2OH)_2].z(solvent)$ (32), $w[Ga^{III}_4(\mu-O)(\mu-OH)(hpdta)_2(CO_3)_2].z(solvent)$ (33), $w[Ga_4(\mu-O)(\mu-OH)(hpdta)_2(O_2CNHC_2H_4NH_3)_2].z(solvent)$ (34), $w[Ga_4(\mu-O)(\mu-OH)(hpdta)_2(O_2CNHC_2H_4NH_3)_2].z(solvent)$ (35), $w[Ga_4(\mu-O)(\mu-OH)(hpdta)_2(O_2CNHNH_3)_2].z(solvent)$ (36), $w[Ga_4(\mu-O)(\mu-OH)(hpdta)_2(O_2CNHC_4H_8NH_3)_2].z(solvent)$ (37), $w[Ga_4(\mu-O)(\mu-OH)(hpdta)_2(O_2CNHC_6H_{12}NH_3)_2].z(solvent)$ (38), $w[Ga_4(\mu-O)(\mu-OH)(hpdta)_2(O_2CNHC_7H_{14}NH_3)_2].z(solvent)$ (39), $w[Ga_4(\mu-O)(\mu-OH)(hpdta)_2(O_2CNHC_2H_4NC_4H_8NH_2)_2].z(solvent)$ (40), $w[Ga_4(\mu-O)(\mu-OH)(hpdta)_2(O_2CNHC_3H_7)_2].z(solvent)$ (41), $w[Ga_4(\mu-O)(\mu-OH)(hpdta)_2(O_2CNHCH_2CH_2HNCH_2CH_2NH_3)_2].z(solvent)$ (42), and $w[Ga_4(\mu-O)(\mu-OH)(hpdta)_2(O_2CNHCH_2CH_2OH)_2].z(solvent)$ (43), $w[Mn_4(\mu-O)(\mu-OH)(hpdta)_2(CO_3)_2].(solvent)$ (44), $w[Mn_4(\mu-O)(\mu-OH)(hpdta)_2(O_2CNHC_2H_4NH_3)_2].z(solvent)$ (45), $w[Mn_4(\mu-O)(\mu-OH)(hpdta)_2(O_2CNHC_2H_4NH_3)_2].z(solvent)$ (46), $w[Mn_4(\mu-O)(\mu-OH)(hpdta)_2(O_2CNHNH_3)_2].z(solvent)$ (47), $w[Mn_4(\mu-O)(\mu-OH)(hpdta)_2(O_2CNHC_4H_8NH_3)_2].z(solvent)$ (48), $w[Mn_4(\mu-O)(\mu-OH)(hpdta)_2(O_2CNHC_6H_{12}NH_3)_2].z(solvent)$ (49), w[Mn$_4$(μ-O)(μ-OH)(hpdta)$_2$(O$_2$CNHC$_7$H$_{14}$NH$_3$)$_2$].z(solvent) (50),
w[Mn$_4$(μ-O)(μ-OH)(hpdta)$_2$(O$_2$CNHC$_2$H$_4$NC$_4$H$_8$NH$_2$)$_2$].z(solvent) (51),
w[Mn$_4$(μ-O)(μ-OH)(hpdta)$_2$(O$_2$CNHC$_3$H$_7$)$_2$].z(solvent) (52),
w[Mn$_4$(μ-O)(μ-OH)(hpdta)$_2$(O$_2$CNHCH$_2$CH$_2$HNCH$_2$CH$_2$NH$_3$)$_2$].z(solvent) (53),
w[Mn$_4$(μ-O)(μ-OH)(hpdta)$_2$(O$_2$CNHCH$_2$CH$_2$OH)$_2$].z(solvent) (54),
w[Cr$_4$(μ-O)(μ-OH)(hpdta)$_2$(CO$_3$)$_2$].(solvent) (55),
w[Cr$_4$(μ-O)(μ-OH)(hpdta)$_2$(O$_2$CNHC$_2$H$_4$NH$_3$)$_2$].z(solvent) (56),
w[Cr$_4$(μ-O)(μ-OH)(hpdta)$_2$(O$_2$CNHC$_2$H$_4$NH$_3$)$_2$].z(solvent) (57),
w[Cr$_4$(μ-O)(μ-OH)(hpdta)$_2$(O$_2$CNHNH$_3$)$_2$].z(solvent) (58),
w[Cr$_4$(μ-O)(μ-OH)(hpdta)$_2$(O$_2$CNHC$_4$H$_8$NH$_3$)$_2$].z(solvent) (59),
w[Cr$_4$(μ-O)(μ-OH)(hpdta)$_2$(O$_2$CNHC$_6$H$_{12}$NH$_3$)$_2$].z(solvent) (60),
w[Cr$_4$(μ-O)(μ-OH)(hpdta)$_2$(O$_2$CNHC$_7$H$_{14}$NH$_3$)$_2$].z(solvent) (61),
w[Cr$_4$(μ-O)(μ-OH)(hpdta)$_2$(O$_2$CNHC$_2$H$_4$NC$_4$H$_8$NH$_2$)$_2$].z(solvent) (62),
w[Cr$_4$(μ-O)(μ-OH)(hpdta)$_2$(O$_2$CNHC$_3$H$_7$)$_2$].z(solvent) (63),
w[Cr$_4$(μ-O)(μ-OH)(hpdta)$_2$(O$_2$CNHCH$_2$CH$_2$HNCH$_2$CH$_2$NH$_3$)$_2$].z(solvent) (64).

9. A method as claimed in claim 1 wherein the tetranuclear complex is isolated as Compound A or Compound B, or wherein the tetranuclear complex assembles in solution from one or more metal salts and one or more aminocarboxylic acid ligands of Compound A or Compound B.

10. A method as claimed in claim 1 wherein the tetranuclear complex or mixture thereof is generated in situ from assembly of one or more corresponding aminocarboxylic ligands and one or more corresponding metal salts in solution, or isolated as a solid that is dissolved in a polar solvent.

11. A method as claimed in claim 1 wherein Compound A, the coordination complex of Compound A, Compound B the coordination complex of Compound B, or a mixture thereof, is immobilised.

12. A method as claimed in claim 1 wherein one or more molecules of Compound A, the coordination complex of Compound A, Compound B, the coordination complex of Compound B, or a mixture thereof, is immobilised onto a solid support and the solid support is alternated between two or more pH environments for reversible sequestration and release of carbon dioxide.

13. A method as claimed in claim 12 wherein the solid support is introduced to an environment with a pH value between pH 7.9 and pH 14 and is exposed to carbon dioxide for sequestration of carbon dioxide.

14. A method as claimed in claim 13 wherein the solid support is introduced to an environment having a pH of less than pH 7.8 which results in the release of carbon dioxide and regeneration of Compound A.

15. A method as claimed in claim 14 wherein the solid support is re-introduced into an environment having a pH of between pH 7.9 and pH 14 and exposed to carbon dioxide for sequestration of carbon dioxide.

16. A method as claimed in claim 11 wherein hpdta ligands or derivatives thereof are used for immobilisation of the tetranuclear complex.

17. A method as claimed in claim 16 wherein the hpdta derivatives are of the formula:

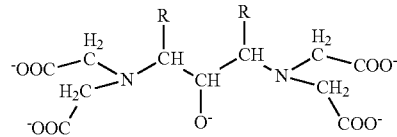

wherein one of the R groups is a H atom and the second R group comprises a 1-alkene chain, a 1-alkene chain, or an akyl chain comprising a terminal functional group selected from a carboxylic acid group, a nitrile group, an aldehyde group, an amine group, or a nitro group.

18. A method as claimed in claim 11 wherein the immobilisation comprises a fixation or crafting of the tetranuclear complex on a solid support.

19. A method as claimed in claim 18 wherein the support is selected from a membrane, a silicate, an alumosilicate, a metal-organic framework, a metal, a metalloid, and carbon, and wherein the fixation is achieved through covalent bonding, coordination bonds, electrostatic interactions between the solid support and the tetranuclear complex, or a combination thereof.

20. A method as claimed in claim 18 wherein the solid support comprises a solid form of Compound A, Compound B, a mixture thereof, a polymerized derivative thereof, or a structural derivative thereof.

21. A compound selected from:
w[Cu$^{III}_4$(μ-O)(μ-OH)(hpdta)$_2$(CO$_3$)$_2$].(solvent) (22),
w[Cu$_4$(μ-O)(μ-OH)(hpdta)$_2$(O$_2$CNHC$_2$H$_4$NH$_3$)$_2$].z(solvent) (23),
w[Cu$_4$(μ-O)(μ-OH)(hpdta)$_2$(O$_2$CNHC$_2$H$_4$NH$_3$)$_2$].z(solvent) (24),
w[Cu$_4$(μ-O)(μ-OH)(hpdta)$_2$(O$_2$CNHNH$_3$)$_2$].z(solvent) (25),
w[Cu$_4$(μ-O)(μ-OH)(hpdta)$_2$(O$_2$CNHC$_4$H$_8$NH$_3$)$_2$].z(solvent) (26),
w[Cu$_4$(μ-O)(μ-OH)(hpdta)$_2$(O$_2$CNHC$_6$H$_{12}$NH$_3$)$_2$].z(solvent) (27),
w[Cu$_4$(μ-O)(μ-OH)(hpdta)$_2$(O$_2$CNHC$_7$H$_{14}$NH$_3$)$_2$].z(solvent) (28),
w[Cu$_4$(μ-O)(μ-OH)(hpdta)$_2$(O$_2$CNHC$_2$H$_4$NC$_4$H$_8$NH$_2$)$_2$].z(solvent) (29),
w[Cu$_4$(μ-O)(μ-OH)(hpdta)$_2$(O$_2$CNHC$_3$H$_7$)$_2$].z(solvent) (30),
w[Cu$_4$(μ-O)(μ-OH)(hpdta)$_2$(O$_2$CNHCH$_2$CH$_2$HNCH$_2$CH$_2$NH$_3$)$_2$].z(solvent) (31),
w[Cu$_4$(μ-O)(μ-OH)(hpdta)$_2$(O$_2$CNHCH$_2$CH$_2$OH)$_2$].z(solvent) (32),
w[Mn$_4$(μ-O)(μ-OH)(hpdta)$_2$(CO$_3$)$_2$].(solvent) (44),
w[Mn$_4$(μ-O)(μ-OH)(hpdta)$_2$(O$_2$CNHC$_2$H$_4$NH$_3$)$_2$].z(solvent) (45),
w[Mn$_4$(μ-O)(μ-OH)(hpdta)$_2$(O$_2$CNHC$_2$H$_4$NH$_3$)$_2$].z(solvent) (46),
w[Mn$_4$(μ-O)(μ-OH)(hpdta)$_2$(O$_2$CNHNH$_3$)$_2$].z(solvent) (47),
w[Mn$_4$(μ-O)(μ-OH)(hpdta)$_2$(O$_2$CNHC$_4$H$_8$NH$_3$)$_2$].z(solvent) (48),
w[Mn$_4$(μ-O)(μ-OH)(hpdta)$_2$(O$_2$CNHC$_6$H$_{12}$NH$_3$)$_2$].z(solvent) (49),
w[Mn$_4$(μ-O)(μ-OH)(hpdta)$_2$(O$_2$CNHC$_7$H$_{14}$NH$_3$)$_2$].z(solvent) (50),
w[Mn$_4$(μ-O)(μ-OH)(hpdta)$_2$(O$_2$CNHC$_2$H$_4$NC$_4$H$_8$NH$_2$)$_2$].z(solvent) (51),
w[Mn$_4$(μ-O)(μ-OH)(hpdta)$_2$(O$_2$CNHC$_3$H$_7$)$_2$].z(solvent) (52), w[Mn$_4$(μ-O)(μ-OH)(hpdta)$_2$(O$_2$CNHCH$_2$CH$_2$HNCH$_2$CH$_2$NH$_3$)$_2$].z(solvent) (53),
w[Mn$_4$(μ-O)(μ-OH)(hpdta)$_2$(O$_2$CNHCH$_2$CH$_2$OH)$_2$].z(solvent) (54),
w[Cr$_4$(μ-O)(μ-OH)(hpdta)$_2$(CO$_3$)$_2$].(solvent) (55),
w[Cr$_4$(μ-O)(μ-OH)(hpdta)$_2$(O$_2$CNHC$_2$H$_4$NH$_3$)$_2$].z(solvent) (56),
w[Cr$_4$(μ-O)(μ-OH)(hpdta)$_2$(O$_2$CNHC$_2$H$_4$NH$_3$)$_2$].z(solvent) (57),
w[Cr$_4$(μ-O)(μ-OH)(hpdta)$_2$(O$_2$CNHNH$_3$)$_2$].z(solvent) (58),
w[Cr$_4$(μ-O)(μ-OH)(hpdta)$_2$(O$_2$CNHC$_4$H$_8$NH$_3$)$_2$].z(solvent) (59),
w[Cr$_4$(μ-O)(μ-OH)(hpdta)$_2$(O$_2$CNHC$_6$H$_{12}$NH$_3$)$_2$].z(solvent) (60),
w[Cr$_4$(μ-O)(μ-OH)(hpdta)$_2$(O$_2$CNHC$_7$H$_{14}$NH$_3$)$_2$]. z(solvent) (61),
w[Cr$_4$(μ-O)(μ-OH)(hpdta)$_2$(O$_2$CNHC$_2$H$_4$NC$_4$H$_8$NH$_2$)$_2$].z(solvent) (62),
w[Cr$_4$(μ-O)(μ-OH)(hpdta)$_2$(O$_2$CNHC$_3$H$_7$)$_2$].z(solvent) (63), and
w[Cr$_4$(μ-O)(μ-OH)(hpdta)$_2$(O$_2$CNHCH$_2$CH$_2$HNCH$_2$CH$_2$NH$_3$)$_2$].z(solvent) (64);
wherein
w is an ion or a mixture of ions in a stoichiometry such that the compound is electronically neutral;
z is 0 or a positive number;
solvent is a solvent; and
hpdta is

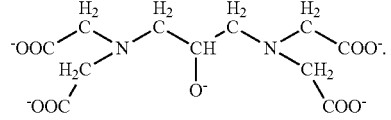

22. A method as claimed in claim 1, wherein the tetranuclear complex serves as a catalyst in at least one of an electrochemical activation of CO$_2$ or a photochemical activation of CO$_2$.

23. A method as claimed in claim 22, further comprising transformation of the CO$_2$ into a fuel or another chemical.

24. A solid support comprising Compound A or Compound B as defined in claim 1.

25. A solid support comprising a compound as defined in claim 21.

26. The method as claimed in claim 1, wherein the method sequesters carbon dioxide from the atmosphere.

* * * * *